(12) United States Patent
Schulte et al.

(10) Patent No.: US 10,688,157 B2
(45) Date of Patent: Jun. 23, 2020

(54) TRUNCATED VON WILLEBRAND FACTOR POLYPEPTIDES FOR TREATING HEMOPHILIA

(71) Applicant: CSL BEHRING LENGNAU AG, Lengnau (CH)

(72) Inventors: Stefan Schulte, Marburg (DE); Hubert Metzner, Marburg (DE); Sabine Pestel, Marburg (DE); Thomas Weimer, Gladenbach (DE)

(73) Assignee: CSL BEHRING LENGNAU AG, Lengnau (CH)

( * ) Notice: Subject to any disclaimer, the term of this patent is extended or adjusted under 35 U.S.C. 154(b) by 0 days.

(21) Appl. No.: 15/576,055

(22) PCT Filed: May 20, 2016

(86) PCT No.: PCT/EP2016/061443
§ 371 (c)(1),
(2) Date: Nov. 21, 2017

(87) PCT Pub. No.: WO2016/188907
PCT Pub. Date: Dec. 1, 2016

(65) Prior Publication Data
US 2018/0161402 A1 Jun. 14, 2018

(30) Foreign Application Priority Data

May 22, 2015 (EP) .................................... 15168930
Mar. 31, 2016 (EP) .................................... 16163239

(51) Int. Cl.
| | | |
|---|---|---|
| A61K 38/00 | (2006.01) |
| A61K 38/37 | (2006.01) |
| A61P 7/04 | (2006.01) |
| A61K 9/00 | (2006.01) |

(52) U.S. Cl.
CPC ............ A61K 38/37 (2013.01); A61K 9/0019 (2013.01); A61P 7/04 (2018.01); A61K 2300/00 (2013.01)

(58) Field of Classification Search
None
See application file for complete search history.

(56) References Cited

U.S. PATENT DOCUMENTS

| 4,399,216 A | 8/1983 | Axel et al. |
| 4,970,300 A | 11/1990 | Fulton et al. |
| 6,403,077 B1 | 6/2002 | Strom et al. |
| 7,256,253 B2 | 8/2007 | Bridon et al. |
| 2004/0087778 A1 | 5/2004 | Feige et al. |

FOREIGN PATENT DOCUMENTS

| EP | 0 117 058 | 8/1984 |
| EP | 0 117 060 | 8/1984 |
| WO | WO 94/15625 | 7/1994 |
| WO | WO 97/03193 | 1/1997 |
| WO | WO 97/11957 | 4/1997 |
| WO | WO 97/40145 | 10/1997 |
| WO | WO 99/55306 | 11/1999 |
| WO | WO 02/060951 A2 | 8/2002 |
| WO | WO 02/103024 A2 | 12/2002 |
| WO | WO 03/076567 A2 | 9/2003 |
| WO | WO 03/087355 A1 | 10/2003 |
| WO | WO 03/093313 A2 | 11/2003 |
| WO | WO 2004/067566 A1 | 8/2004 |
| WO | WO 2004/075923 A2 | 9/2004 |
| WO | WO 2004/101740 A2 | 11/2004 |
| WO | WO 2005/000892 A2 | 1/2005 |
| WO | WO 2005/001025 A2 | 6/2005 |
| WO | WO 2005/063808 A1 | 7/2005 |
| WO | WO 2006/000448 A2 | 1/2006 |
| WO | WO 2006/053299 A2 | 5/2006 |
| WO | WO 2006/078801 A2 | 7/2006 |
| WO | WO 2006/108590 A1 | 10/2006 |
| WO | WO 2007/090584 A1 | 8/2007 |
| WO | WO 2007/126808 A1 | 11/2007 |
| WO | WO 2007/144173 A1 | 12/2007 |
| WO | WO 2008/077616 A1 | 7/2008 |
| WO | WO 2008/151817 A1 | 12/2008 |
| WO | WO 2009/156137 A1 | 12/2009 |
| WO | WO 2011/060242 A2 | 5/2011 |
| WO | WO 2012/173873 A2 | 12/2012 |
| WO | WO 2013/083858 A1 | 6/2013 |
| WO | WO 2013/093760 A2 | 6/2013 |
| WO | WO 2013/106787 A1 | 7/2013 |
| WO | WO 2013/120939 A1 | 8/2013 |
| WO | WO2013/167303 | * 11/2013 |
| WO | WO 2014/011819 A2 | 1/2014 |
| WO | WO2014/198699 | * 12/2014 |

(Continued)

OTHER PUBLICATIONS

International Search Report and the Written Opinion of the International Searching Authority, issued in International Application No. PCT/EP2016/061443, dated Dec. 7, 2017, 13 pages.
European Search Report and Written Opinion, issued in EP Patent Application No. 15168930.4, dated Feb. 17, 2016, 11 pages.
Graham, F. L., et al., "Characteristics of a Human Cell Line Transformed by DNA from Human Adenovirus Type 5," J. Gen. Virol., vol. 36, pp. 59-74 (1977).
Mantei, N., et al., "Rabbit β-globin mRNA production in mouse L cells transformed with cloned rabbit β-globin chromosomal DNA," Nature, vol. 281, pp. 40-46 (1979).
Mather, J. P., "Establishment and Characterization of Two Distinct Mouse Testicular Epithelial Cell Lines," Biology of Reproduction, vol. 23, pp. 243-252 (1980).
Osol, A., "Remington's Pharmaceutical Science," Mack Publishing Company, 16th Ed. (1980), 1 page on general information.

(Continued)

*Primary Examiner* — Jeanette M Lieb
(74) *Attorney, Agent, or Firm* — Finnegan, Henderson, Farabow, Garrett & Dunner, LLP

(57) ABSTRACT

The invention relates to a polypeptide comprising a truncated von Willebrand Factor (VWF) for use in the treatment of a blood coagulation disorder, wherein the polypeptide carries a half-life extending moiety and is administered in molar excess over Factor VIII and/or endogenous VWF.

23 Claims, 26 Drawing Sheets

Specification includes a Sequence Listing.

(56) References Cited

FOREIGN PATENT DOCUMENTS

| WO | WO 2014/198699 A2 | 12/2014 |
|----|-------------------|---------|
| WO | WO 2015/106052 A1 | 7/2015  |

OTHER PUBLICATIONS

Urlaub, G., et al., "Isolation of Chinese hamster cell mutants deficient in dihdrofolate reductase activity," Proc. Natl. Acad. Sci., vol. 77, No. 7, pp. 4216-4220 (1980).

Gething, M. J., et al., "Cell-surface expression of influenza haemagglutinin from a cloned DNA copy of the RNA gene," Nature, vol. 293, No. 293, pp. 620-625 (1981).

Mather, J. P., "Culture of Testicular Cells in Hormone-Supplemented Serum-Free Medium," Annals NY Acad. Sci., vol. 383, No. 1, pp. 44-68 (1982).

Lee, M. L., et al., "An Effect of Predilution on Potency Assays of Factor VIII Concentrates," Thrombosis Research, vol. 30, pp. 511-519 (1983).

Collins, C. J., et al., "Molecular cloning of the human gene4 for von Willebrand factor and identification of the transcription initiation site," Proc. Natl. Acad. Sci., vol. 84, pp. 4393-4397 (1987).

Mansour, S. L., et al., "Disruption of the proto-oncogene int-2 in mouse embryo-derived stem cells: a general strategy for targeting mutations to non-selectable genes," Nature, vol. 336, No. 24, pp. 348-352 (1988).

Kaufman, R. J., et al., "Effect of von Willebrand Factor Coexpression on the Synthesis and Secretion of Factor VIII in Chinese Hamster Ovary Cells," Molecular and Cellular Biology, vol. 9, No. 3, pp. 1233-1242 (1989).

Keown, W. A., et al., "Methods for Introducing DNA into Mammalian Cells," Methods in Enzymology, vol. 185, pp. 527-537 (1993).

Hawley-Nelson, P., et al., "LipofectAMINE™ Reagent: A New, Higher Efficiency Polycationic Liposome Transfection Reagent," Focus, vol. 15, No. 3, pp. 73-79 (1993).

Fischer, B., et al., "Structural analysis of recombinant von Willebrand factor: identification of hetero- and homo-dimers," FEBS Letters, vol. 351, pp. 345-348 (1994).

Dumont, J. A., et al., "Monomeric Fc Fusions—Impact on Pharmacokinetic and Biological Activity of Protein Therapeutics," Biodrugs, Vo. 20(3), pp. 151-160 (2006).

Schellenberger, V., et al., "A recombinant polypeptide extens the in vivo half-life of peptides and proteins in a tunable manner," Nature Biotechnology, vol. 27, No. 12, pp. 1186-1190 (2009).

Zhou, Y. F., et al., "Sequence and structure relationships within von Willebrand Factor," Blood, vol. 120, No. 2, pp. 449-458 (2012).

Marder, V. J., et al., "Hemostasis and Thrombosis—Basic Principles and Clinical Practice," 6$^{th}$ Edition, Chapter 13, pp. 197-207 (2013).

Yee, A., et al., "A von Willebrand factor fragment containing the D'D3 domains is sufficient to stabilize coagulation factor VIII in mice," Blood, vol. 124, No. 3, pp. 445-452 (2014).

\* cited by examiner

SEQUENCE LISTING

```
<160> NUMBER OF SEQ ID NOS: 8

<210> SEQ ID NO 1
<211> LENGTH: 5616
<212> TYPE: DNA
<213> ORGANISM: Artificial Sequence
<220> FEATURE:
<223> OTHER INFORMATION: DNA encoding construct VWF fragment - G/S
      linker - albumin
<220> FEATURE:
<221> NAME/KEY: misc_feature
<222> LOCATION: (1)..(6)
<223> OTHER INFORMATION: EcoRI restriction enzyme cleavage site
<220> FEATURE:
<221> NAME/KEY: misc_feature
<222> LOCATION: (32)..(3757)
<223> OTHER INFORMATION: coding sequence for VWF amino acids 1 to 1242
<220> FEATURE:
<221> NAME/KEY: misc_feature
<222> LOCATION: (3758)..(3850)
<223> OTHER INFORMATION: coding sequence for glycine/serine linker
<220> FEATURE:
<221> NAME/KEY: misc_feature
<222> LOCATION: (3851)..(5608)
<223> OTHER INFORMATION: coding sequence for human albumin
<220> FEATURE:
<221> NAME/KEY: misc_feature
<222> LOCATION: (5609)..(5616)
<223> OTHER INFORMATION: NotI restriction enzyme cleavage site

<400> SEQUENCE: 1
gaattcccgc agccctcatt tgcagggaa gatgattcct gccagatttg ccggggtgct      60
gcttgctctg gccctcattt tgccagggac cctttgtgca gaaggaactc gcggcaggtc     120
atccacggcc cgatgcagcc ttttcggaag tgacttcgtc aacacctttg atgggagcat     180
gtacagcttt gcgggatact gcagttacct cctggcaggg ggctgccaga aacgctcctt     240
ctcgattatt ggggacttcc agaatggcaa gagagtgagc ctctccgtgt atcttgggga     300
attttttgac atccatttgt ttgtcaatgg taccgtgaca caggggggacc aaagagtctc     360 catgccctat gcctccaaag ggctgtatct agaaactgag gctgggtact acaagctgtc     420
cggtgaggcc tatggctttg tggccaggat cgatggcagc ggcaactttc aagtcctgct     480
gtcagacaga tacttcaaca agacctgcgg gctgtgtggc aactttaaca tctttgctga     540
agatgacttt atgacccaag aagggaccct tgacctcggac ccttatgact tgccaactc     600 atgggctctg agcagtggag aacagtggtg tgaacgggca tctcctccca gcagctcatg     660
caacatctcc tctggggaaa tgcagaaggg cctgtgggag cagtgccagc ttctgaagag     720
cacctcggtg tttgcccgct gccaccctct ggtgaccccc gagcctttg tggccctgtg     780 tgagaagact tgtgtgagt gtgctggggg gctggagtgc gcctgccctg ccctcctgga     840
gtacgcccgg acctgtgccc aggagggaat ggtgctgtac ggctggaccg accacagcgc     900
gtgcagccca gtgtgccctg ctggtatgga gtataggcag tgtgtgtccc cttgcgccag     960
gacctgccag agcctgcaca tcaatgaaat gtgtcaggag cgatgcgtgg atggctgcag    1020
```

```
ctgccctgag ggacagctcc tggatgaagg cctctgcgtg gagagcaccg agtgtccctg      1080
cgtgcattcc ggaaagcgct accctcccgg cacctccctc tctcgagact gcaacacctg      1140
catttgccga aacagccagt ggatctgcag caatgaagaa tgtccagggg agtgccttgt      1200
cacaggtcaa tcacacttca agagctttga caacagatac ttcaccttca gtgggatctg      1260
ccagtacctg ctggcccggg attgccagga ccactccttc tccattgtca ttgagactgt      1320
ccagtgtgct gatgaccgcg acgctgtgtg cacccgctcc gtcaccgtcc ggctgcctgg      1380
cctgcacaac agccttgtga aactgaagca tggggcagga gttgccatgg atggccagga      1440
cgtccagctc cccctcctga aggtgacct ccgcatccag catacagtga cggcctccgt       1500
gcgcctcagc tacggggagg acctgcagat ggactgggat ggccgcggga ggctgctggt      1560
gaagctgtcc cccgtctatg ccgggaagac ctgcggcctg tgtgggaatt acaatggcaa      1620
ccagggcgac gacttcctta ccccctctgg gctggcggag cccgggtgg aggacttcgg       1680 gaacgcctgg aagctgcacg gggactgcca ggacctgcag aagcagcaca gcgatccctg      1740
cgccctcaac ccgcgcatga ccaggttctc cgaggaggcg tgcgcggtcc tgacgtcccc      1800
cacattcgag gcctgccatc gtgccgtcag cccgctgccc tacctgcgga actgccgcta      1860
cgacgtgtgc tcctgctcgg acggccgcga gtgcctgtgc ggcgccctgg ccagctatgc      1920
cgcggcctgc gcggggagag gcgtgcgcgt cgcgtggcgc gagccaggcc gctgtgagct      1980
gaactgcccg aaaggccagg tgtacctgca gtgcgggacc ccctgcaacc tgacctgccg      2040
ctctctctct acccggatg aggaatgcaa tgaggcctgc ctggagggct gcttctgccc       2100
cccagggctc tacatggatg agaggggga ctgcgtgccc aaggcccagt gccctgtta       2160 ctatgacggt gagatcttcc agccagaaga catcttctca gaccatcaca ccatgtgcta      2220
ctgtgaggat ggcttcatgc actgtaccat gagtggagtc cccggaagct gctgcctga      2280 cgctgtcctc agcagtcccc tgtctcatcg cagcaaaagg agcctatcct gtcggccccc      2340
catggtcaag ctggtgtgtc ccgctgacaa cctgcgggct gaagggctcg agtgtaccaa      2400
aacgtgccag aactatgacc tggagtgcat gagcatgggc tgtgtctctg gctgcctctg      2460
ccccccgggc atggtccggc atgagaacag atgtgtggcc ctggaaaggt gtccctgctt      2520
ccatcagggc aaggagtatg cccctggaga aacagtgaag attggctgca acacttgtgt      2580
ctgtcgggac cggaagtgga actgcacaga ccatgtgtgt gatgccacgt gctccacgat      2640
cggcatggcc cactacctca ccttcgacgg gctcaaatac ctgttccccg gggagtgcca      2700
gtacgttctg gtgcaggatt actgcggcag taaccctggg acctttcgga tcctagtggg      2760
gaataaggga tgcagccacc cctcagtgaa atgcaagaaa cgggtcacca tcctggtgga      2820
gggaggagag attgagctgt ttgacgggga ggtgaatgtg aagaggccca tgaaggatga      2880
gactcacttt gaggtggtgg agtctggccg gtacatcatt ctgctgctgg gcaaagccct      2940
ctccgtggtc tgggaccgcc acctgagcat tccgtggtc ctgaagcaga cataccagga     3000
gaaagtgtgt ggcctgtgtg ggaatttga tggcatccag aacaatgacc tcaccagcag      3060
caacctccaa gtggaggaag accctgtgga ctttgggaac tcctggaaag tgagctcgca      3120
gtgtgctgac accagaaaag tgcctctgga ctcatcccct gccacctgcc ataacaacat      3180
catgaagcag acgatggtgg attcctcctg tagaatcctt accagtgacg tcttccagga      3240
ctgcaacaag ctggtggacc ccgagccata tctggatgtc tgcatttacg acacctgctc      3300
ctgtgagtcc attggggact gcgcctgctt ctgcgacacc attgctgcct atgcccacgt      3360
```

| | |
|---|---|
| gtgtgcccag catggcaagg tggtgacctg gaggacggcc acattgtgcc cccagagctg | 3420 |
| cgaggagagg aatctccggg agaacgggta tgagtgtgag tggcgctata acagctgtgc | 3480 |
| acctgcctgt caagtcacgt gtcagcaccc tgagccactg gcctgccctg tgcagtgtgt | 3540 |
| ggagggctgc catgcccact gccctccagg gaaaatcctg gatgagcttt tgcagacctg | 3600 |
| cgttgaccct gaagactgtc cagtgtgtga ggtggctggc cggcgttttg cctcaggaaa | 3660 |
| gaaagtcacc ttgaatccca gtgaccctga gcactgccag atttgccact gtgatgttgt | 3720 |
| caacctcacc tgtgaagcct gccaggagcc gggaggctcg agcggggat ctggcgggtc | 3780 |
| tggaggctct ggagggtcgg gaggctctgg aggctctggg ggatctggcg ggtctggagg | 3840 |
| gtcgggatcc gatgcacaca agagtgaggt tgctcatcgg tttaaagatt tgggagaaga | 3900 |
| aaatttcaaa gccttggtgt tgattgcctt tgctcagtat cttcagcagt gtccatttga | 3960 |
| agatcatgta aaattagtga atgaagtaac tgaatttgca aaacatgtg ttgctgatga | 4020 |
| gtcagctgaa aattgtgaca atcacttca tacccttttt ggagacaaat tatgcacagt | 4080 |
| tgcaactctt cgtgaaacct atggtgaaat ggctgactgc tgtgcaaaac aagaacctga | 4140 |
| gagaaatgaa tgcttcttgc aacacaaaga tgacaaccca aacctccccc gattggtgag | 4200 |
| accagaggtt gatgtgatgt gcactgcttt tcatgacaat aagagacat tttgaaaaa | 4260 |
| atacttatat gaaattgcca gaagacatcc ttacttttat gccccggaac tccttttctt | 4320 |
| tgctaaaagg tataaagctg cttttacaga atgttgccaa gctgctgata agctgcctg | 4380 |
| cctgttgcca agctcgatg aacttcggga tgaagggaag gcttcgtctg ccaaacagag | 4440 |
| actcaagtgt gccagtctcc aaaaatttgg agaaagagct ttcaaagcat gggcagtagc | 4500 |
| tcgcctgagc cagagatttc ccaaagctga gtttgcagaa gtttccaagt tagtgacaga | 4560 |
| tcttaccaaa gtccacacgg aatgctgcca tggagatctg cttgaatgtg ctgatgacag | 4620 |
| ggcggacctt gccaagtata tctgtgaaaa tcaagattcg atctccagta aactgaagga | 4680 |
| atgctgtgaa aaacctctgt tggaaaaatc ccactgcatt gccgaagtgg aaaatgatga | 4740 |
| gatgcctgct gacttgcctt cattagctgc tgattttgtt gaaagtaagg atgtttgcaa | 4800 |
| aaactatgct gaggcaaagg atgtcttcct gggcatgttt ttgtatgaat atgcaagaag | 4860 |
| gcatcctgat tactctgtcg tgctgctgct gagacttgcc aagacatatg aaaccactct | 4920 |
| agagaagtgc tgtgccgctg cagatcctca tgaatgctat gccaaagtgt tcgatgaatt | 4980 |
| taaacctctt gtggaagagc tcagaattt aatcaaacaa aattgtgagc tttttgagca | 5040 |
| gcttggagag tacaaattcc agaatgcgct attagttcgt tacaccaaga agtaccccca | 5100 |
| agtgtcaact ccaactcttg tagaggtctc aagaaaccta ggaaaagtgg gcagcaaatg | 5160 |
| ttgtaaacat cctgaagcaa aaagaatgcc ctgtgcagaa gactatctat ccgtggtcct | 5220 |
| gaaccagtta tgtgtgttgc atgagaaaac gccagtaagt gacagagtca ccaaatgctg | 5280 |
| cacagaatcc ttggtgaaca ggcgaccatg ctttttcagct ctggaagtcg atgaaacata | 5340 |
| cgttcccaaa gagtttaatg ctgaaacatt caccttccat gcagatatat gcacactttc | 5400 |
| tgagaaggag agacaaatca agaaacaaac tgcacttgtt gagctcgtga acacaagcc | 5460 |
| caaggcaaca aaagagcaac tgaaagctgt tatggatgat ttcgcagctt ttgtagagaa | 5520 |
| gtgctgcaag gctgacgata aggagacctg ctttgccgag gagggtaaaa aacttgttgc | 5580 |
| tgcaagtcaa gctgccttag gcttataggc ggccgc | 5616 |

```
<210> SEQ ID NO 2
<211> LENGTH: 1095
```

<212> TYPE: PRT
<213> ORGANISM: Artificial Sequence
<220> FEATURE:
<223> OTHER INFORMATION: polypeptide encoded by SEQ ID NO:1
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(510)
<223> OTHER INFORMATION: glycine/serine linker
<220> FEATURE:
<221> NAME/KEY: MISC_FEATURE
<222> LOCATION: (511)..(1195)
<223> OTHER INFORMATION: human albumin

<400> SEQUENCE: 2

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320
```

```
Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Ser Gly Gly Ser Gly Gly Ser Gly Gly Ser Gly Gly Ser Gly Gly Ser
                485                 490                 495

Gly Gly Ser Gly Gly Ser Gly Gly Ser Gly Gly Ser Gly Ser Asp Ala
            500                 505                 510

His Lys Ser Glu Val Ala His Arg Phe Lys Asp Leu Gly Glu Glu Asn
        515                 520                 525

Phe Lys Ala Leu Val Leu Ile Ala Phe Ala Gln Tyr Leu Gln Gln Cys
    530                 535                 540

Pro Phe Glu Asp His Val Lys Leu Val Asn Glu Val Thr Glu Phe Ala
545                 550                 555                 560

Lys Thr Cys Val Ala Asp Glu Ser Ala Glu Asn Cys Asp Lys Ser Leu
                565                 570                 575

His Thr Leu Phe Gly Asp Lys Leu Cys Thr Val Ala Thr Leu Arg Glu
            580                 585                 590

Thr Tyr Gly Glu Met Ala Asp Cys Cys Ala Lys Gln Glu Pro Glu Arg
        595                 600                 605

Asn Glu Cys Phe Leu Gln His Lys Asp Asp Asn Pro Asn Leu Pro Arg
    610                 615                 620

Leu Val Arg Pro Glu Val Asp Val Met Cys Thr Ala Phe His Asp Asn
625                 630                 635                 640

Glu Glu Thr Phe Leu Lys Lys Tyr Leu Tyr Glu Ile Ala Arg Arg His
                645                 650                 655

Pro Tyr Phe Tyr Ala Pro Glu Leu Leu Phe Phe Ala Lys Arg Tyr Lys
            660                 665                 670

Ala Ala Phe Thr Glu Cys Cys Gln Ala Ala Asp Lys Ala Ala Cys Leu
        675                 680                 685

Leu Pro Lys Leu Asp Glu Leu Arg Asp Glu Gly Lys Ala Ser Ser Ala
    690                 695                 700

Lys Gln Arg Leu Lys Cys Ala Ser Leu Gln Lys Phe Gly Glu Arg Ala
705                 710                 715                 720

Phe Lys Ala Trp Ala Val Ala Arg Leu Ser Gln Arg Phe Pro Lys Ala
                725                 730                 735

Glu Phe Ala Glu Val Ser Lys Leu Val Thr Asp Leu Thr Lys Val His
```

```
                    740              745              750
    Thr Glu Cys Cys His Gly Asp Leu Leu Glu Cys Ala Asp Asp Arg Ala
                755              760              765
    Asp Leu Ala Lys Tyr Ile Cys Glu Asn Gln Asp Ser Ile Ser Ser Lys
                770              775              780
    Leu Lys Glu Cys Cys Glu Lys Pro Leu Leu Glu Lys Ser His Cys Ile
    785              790              795              800
    Ala Glu Val Glu Asn Asp Glu Met Pro Ala Asp Leu Pro Ser Leu Ala
                805              810              815
    Ala Asp Phe Val Glu Ser Lys Asp Val Cys Lys Asn Tyr Ala Glu Ala
                820              825              830
    Lys Asp Val Phe Leu Gly Met Phe Leu Tyr Glu Tyr Ala Arg Arg His
                835              840              845
    Pro Asp Tyr Ser Val Val Leu Leu Leu Arg Leu Ala Lys Thr Tyr Glu
                850              855              860
    Thr Thr Leu Glu Lys Cys Cys Ala Ala Ala Asp Pro His Glu Cys Tyr
    865              870              875              880
    Ala Lys Val Phe Asp Glu Phe Lys Pro Leu Val Glu Glu Pro Gln Asn
                885              890              895
    Leu Ile Lys Gln Asn Cys Glu Leu Phe Glu Gln Leu Gly Glu Tyr Lys
                900              905              910
    Phe Gln Asn Ala Leu Leu Val Arg Tyr Thr Lys Lys Val Pro Gln Val
                915              920              925
    Ser Thr Pro Thr Leu Val Glu Val Ser Arg Asn Leu Gly Lys Val Gly
                930              935              940
    Ser Lys Cys Cys Lys His Pro Glu Ala Lys Arg Met Pro Cys Ala Glu
    945              950              955              960
    Asp Tyr Leu Ser Val Val Leu Asn Gln Leu Cys Val Leu His Glu Lys
                965              970              975
    Thr Pro Val Ser Asp Arg Val Thr Lys Cys Cys Thr Glu Ser Leu Val
                980              985              990
    Asn Arg Arg Pro Cys Phe Ser Ala Leu Glu Val Asp Glu Thr Tyr Val
                995              1000             1005
    Pro Lys Glu Phe Asn Ala Glu Thr Phe Thr Phe His Ala Asp Ile
        1010             1015             1020
    Cys Thr Leu Ser Glu Lys Glu Arg Gln Ile Lys Lys Gln Thr Ala
        1025             1030             1035
    Leu Val Glu Leu Val Lys His Lys Pro Lys Ala Thr Lys Glu Gln
        1040             1045             1050
    Leu Lys Ala Val Met Asp Asp Phe Ala Ala Phe Val Glu Lys Cys
        1055             1060             1065
    Cys Lys Ala Asp Asp Lys Glu Thr Cys Phe Ala Glu Glu Gly Lys
        1070             1075             1080
    Lys Leu Val Ala Ala Ser Gln Ala Ala Leu Gly Leu
        1085             1090             1095

<210> SEQ ID NO 3
<211> LENGTH: 8442
<212> TYPE: DNA
<213> ORGANISM: Homo Sapiens

<400> SEQUENCE: 3
atgattcctg ccagatttgc cggggtgctg cttgctctgg ccctcatttt gccagggacc      60
ctttgtgcag aaggaactcg cggcaggtca tccacggccc gatgcagcct tttcggaagt     120
```

```
gacttcgtca acacctttga tgggagcatg tacagctttg cgggatactg cagttacctc    180
ctggcagggg gctgccagaa acgctccttc tcgattattg ggacttcca gaatggcaag    240
agagtgagcc tctccgtgta tcttggggaa tttttttgaca tccatttgtt tgtcaatggt   300
accgtgacac agggggacca aagagtctcc atgcccatg cctccaaagg ctgtatcta    360
gaaactgagg ctgggtacta caagctgtcc ggtgaggcct atggctttgt ggccaggatc    420
gatggcagcg gcaactttca gtcctgctg tcagacagat acttcaacaa gacctgcggg    480
ctgtgtggca actttaacat ctttgctgaa gatgacttta tgacccaaga agggaccttg    540
acctcggacc cttatgactt tgccaactca tgggctctga gcagtggaga acagtggtgt    600
gaacgggcat ctcctcccag cagctcatgc aacatctcct ctggggaaat gcagaagggc    660
ctgtgggagc agtgccagct tctgaagagc acctcggtgt ttgcccgctg ccaccctctg    720
gtggaccccg agccttttgt ggccctgtgt gagaagactt tgtgtgagtg tgctggggg    780
ctggagtgcg cctgccctgc cctcctggag tacgcccgga cctgtgccca ggagggaatg    840
gtgctgtacg gctggaccga ccacagcgcg tgcagcccag tgtgccctgc tggtatggag    900
tataggcagt gtgtgtcccc ttgcgccagg acctgccaga gcctgcacat caatgaaatg    960
tgtcaggagc gatgcgtgga tggctgcagc tgccctgagg acagctcct ggatgaaggc   1020
ctctgcgtgg agagcaccga gtgtccctgc gtgcattccg gaaagcgcta ccctcccggc   1080
acctccctct ctcgagactg caacacctgc atttgccgaa acagccagtg gatctgcagc   1140
aatgaagaat gtccagggga gtgccttgtc acaggtcaat cacacttcaa gagctttgac   1200
aacagatact tcaccttcag tgggatctgc cagtacctgc tggcccggga ttgccaggac   1260
cactccttct ccattgtcat tgagactgtc cagtgtgctg atgaccgcga cgctgtgtgc   1320
acccgctccg tcaccgtccg gctgcctggc ctgcacaaca gccttgtgaa actgaagcat   1380
ggggcaggag ttgccatgga tggccaggac gtccagctcc ccctcctgaa aggtgacctc   1440
cgcatccagc atacagtgac ggcctccgtg cgcctcagct acggggagga cctgcagatg   1500
gactgggatg ccgcgggag gctgctggtg aagctgtccc ccgtctatgc cgggaagacc   1560
tgcggcctgt gtgggaatta caatggcaac cagggcgacg acttccttac ccctctgggg   1620
ctggcggagc cccgggtgga ggacttcggg aacgcctgga agctgcacgg ggactgccag   1680
gacctgcaga agcagcacag cgatccctgc gccctcaacc cgcgcatgac caggttctcc   1740
gaggaggcgt gcgcggtcct gacgtccccc acattcgagg cctgccatcg tgccgtcagc   1800
ccgctgccct acctgcggaa ctgccgctac gacgtgtgct cctgctcgga cggccgcgag   1860
tgcctgtgcg gcgccctggc cagctatgcc gcggcctgcg cggggagagg cgtgcgcgtc   1920
gcgtggcgcg agccaggccg ctgtgagctg aactgcccga aggccaggt gtacctgcag   1980
tgcgggaccc cctgcaacct gacctgccgc tctctctctt acccggatga ggaatgcaat   2040
gaggcctgcc tggagggctg cttctgcccc ccagggctct acatggatga gaggggggac   2100
tgcgtgccca aggcccagtg cccctgttac tatgacggtg agatcttcca gccagaagac   2160
atcttctcag accatcacac catgtgctac tgtgaggatg gcttcatgca ctgtaccatg   2220
agtggagtcc ccggaagctt gctgcctgac gctgtcctca gcagtcccct gtctcatcgc   2280
agcaaaagga gcctatcctg tcggcccccc atggtcaagc tggtgtgtcc cgctgacaac   2340
ctgcgggctg aagggctcga gtgtaccaaa acgtgccaga actatgacct ggagtgcatg   2400
agcatgggct gtgtctctgg ctgcctctgc cccccgggca tggtccggca tgagaacaga   2460
```

```
tgtgtggccc tggaaaggtg tccctgcttc catcagggca aggagtatgc cctggagaa      2520 acagtgaaga ttggctgcaa cacttgtgtc tgtcgggacc ggaagtggaa ctgcacagac      2580
catgtgtgtg atgccacgtg ctccacgatc ggcatggccc actacctcac cttcgacggg      2640
ctcaaatacc tgttccccgg ggagtgccag tacgttctgg tgcaggatta ctgcggcagt      2700
aaccctggga cctttcggat cctagtgggg aataagggat gcagccaccc ctcagtgaaa      2760
tgcaagaaac gggtcaccat cctggtggag ggaggagaga ttgagctgtt tgacggggag      2820
gtgaatgtga agaggcccat gaaggatgag actcactttg aggtggtgga gtctggccgg      2880
tacatcattc tgctgctggg caaagccctc tccgtggtct gggaccgcca cctgagcatc      2940
tccgtggtcc tgaagcagac ataccaggag aaagtgtgtg gcctgtgtgg aatttttgat      3000
ggcatccaga acaatgacct caccagcagc aacctccaag tggaggaaga ccctgtggac      3060
tttgggaact cctggaaagt gagctcgcag tgtgctgaca ccagaaaagt gcctctggac      3120
tcatcccctg ccacctgcca taacaacatc atgaagcaga cgatggtgga ttcctcctgt      3180
agaatcctta ccagtgacgt cttccaggac tgcaacaagc tggtggaccc cgagccatat      3240
ctggatgtct gcatttacga cacctgctcc tgtgagtcca ttggggactg cgcctgcttc      3300
tgcgacacca ttgctgccta tgcccacgtg tgtgcccagc atggcaaggt ggtgacctgg      3360
aggacggcca cattgtgccc ccagagctgc gaggagagga tctccgggga acgggtat      3420 gagtgtgagt ggcgctataa cagctgtgca cctgcctgtc aagtcacgtg tcagcaccct      3480
gagccactgg cctgccctgt gcagtgtgtg gagggctgcc atgcccactg ccctccaggg      3540
aaaatcctgg atgagctttt gcagacctgc gttgaccctg aagactgtcc agtgtgtgag      3600
gtggctggcc ggcgttttgc ctcaggaaag aaagtcacct gaatcccag tgaccctgag      3660 cactgccaga tttgccactg tgatgttgtc aacctcacct gtgaagcctg ccaggagccg      3720
ggaggcctgg tggtgcctcc cacagatgcc ccggtgagcc ccaccactct gtatgtggag      3780
gacatctcgg aaccgccgtt gcacgatttc tactgcagca ggctactgga cctggtcttc      3840
ctgctggatg gctcctccag gctgtccgag gctgagtttg aagtgctgaa ggcctttgtg      3900
gtggacatga tggagcggct gcgcatctcc cagaagtggg tccgcgtggc cgtggtggag      3960
taccacgacg gctcccacgc ctacatcggg ctcaaggacc ggaagcgacc gtcagagctg      4020
cggcgcattg ccagccaggt gaagtatgcg ggcagccagg tggcctccac cagcgaggtc      4080
ttgaaataca cactgttcca aatcttcagc aagatcgacc gccctgaagc ctcccgcatc      4140
gccctgctcc tgatggccag ccaggagccc caacggatgt cccggaactt tgtccgctac      4200
gtccagggcc tgaagaagaa gaaggtcatt gtgatcccgg tgggcattgg ccccatgcc      4260 aacctcaagc agatccgcct catcgagaag caggcccctg agaacaaggc cttcgtgctg      4320
agcagtgtgg atgagctgga gcagcaaagg gacgagatcg ttagctacct ctgtgacctt      4380
gcccctgaag cccctcctcc tactctgccc ccccacatgg cacaagtcac tgtgggcccg      4440
gggctcttgg gggtttcgac cctggggccc aagaggaact ccatggttct ggatgtggcg      4500
ttcgtcctgg aaggatcgga caaaattggt gaagccgact tcaacaggag caaggagttc      4560
atggaggagg tgattcagcg gatggatgtg gccaggaca gcatccacgt cacggtgctg      4620
cagtactcct acatggtgac cgtggagtac cccttcagcg aggcacagtc caaaggggac      4680
atcctgcagc gggtgcgaga gatccgctac cagggcggca acaggaccaa cactgggctg      4740
gccctgcggt acctctctga ccacagcttc ttggtcagcc agggtgaccg ggagcaggcg      4800
cccaacctgg tctacatggt caccggaaat cctgcctctg atgagatcaa gaggctgcct      4860
```

```
ggagacatcc aggtggtgcc cattggagtg ggccctaatg ccaacgtgca ggagctggag    4920
aggattggct ggcccaatgc ccctatcctc atccaggact ttgagacgct cccccgagag    4980
gctcctgacc tggtgctgca gaggtgctgc tccggagagg ggctgcagat ccccaccctc    5040 tccccctgcac ctgactgcag ccagcccctg acgtgatcc ttctcctgga tggctcctcc    5100
agtttcccag cttcttattt tgatgaaatg aagagtttcg ccaaggcttt catttcaaaa    5160
gccaatatag ggcctcgtct cactcaggtg tcagtgctgc agtatggaag catcaccacc    5220
attgacgtgc catggaacgt ggtcccggag aaagcccatt tgctgagcct tgtggacgtc    5280
atgcagcggg agggaggccc cagccaaatc ggggatgcct ggggctttgc tgtgcgatac    5340
ttgacttcag aaatgcatgg ggcgcgcccg ggagcctcaa aggcggtggt catcctggtc    5400
acggacgtct ctgtggattc agtggatgca gcagctgatg ccgccaggtc aacagagtg    5460 acagtgttcc ctattggaat tggagatcgc tacgatgcag cccagctacg atcttggca    5520 ggcccagcag gcgactccaa cgtggtgaag ctccagcgaa tcgaagacct ccctaccatg    5580
gtcaccttgg gcaattcctt cctccacaaa ctgtgctctg gatttgttag gatttgcatg    5640
gatgaggatg ggaatgagaa gaggcccggg gacgtctgga ccttgccaga ccagtgccac    5700
accgtgactt gccagccaga tggccagacc ttgctgaaga gtcatcgggt caactgtgac    5760 cggggggctga ggccttcgtg ccctaacagc cagtcccctg ttaaagtgga agagacctgt    5820
ggctgccgct ggacctgccc ctgcgtgtgc acaggcagct ccactcggca catcgtgacc    5880
tttgatgggc agaatttcaa gctgactggc agctgttctt atgtcctatt tcaaaacaag    5940
gagcaggacc tggaggtgat tctccataat ggtgcctgca gccctggagc aaggcagggc    6000
tgcatgaaat ccatcgaggt gaagcacagt gccctctccg tcgagctgca cagtgacatg    6060
gaggtgacgg tgaatgggag actggtctct gttccttacg tgggtgggaa catggaagtc    6120
aacgtttatg gtgccatcat gcatgaggtc agattcaatc accttggtca catcttcaca    6180
ttcactccac aaaacaatga gttccaactg cagctcagcc caagactttt tgcttcaaag    6240
acgtatggtc tgtgtgggat ctgtgatgag aacggagcca atgacttcat gctgagggat    6300
ggcacagtca cccacagactg gaaaacactt gttcaggaat ggactgtgca gcggccaggg    6360
cagacgtgcc agcccatcct ggaggagcag tgtcttgtcc ccgacagctc ccactgccag    6420
gtcctcctct taccactgtt tgctgaatgc acaaggtcc tggctccagc cacattctat    6480
gccatctgcc agcaggacag ttgccaccag gagcaagtgt gtgaggtgat cgcctcttat    6540
gcccaccccc gtcggaccaa cggggtctgc gttgactgga ggacacctga tttctgtgct    6600
atgtcatgcc caccatctct ggtttataac cactgtgagc atggctgtcc ccggcactgt    6660
gatggcaacg tgagctcctg tggggaccat ccctccgaag gctgtttctg ccctccagat    6720
aaagtcatgt ggaaggcag ctgtgtccct gaagaggcct gcactcagtg cattggtgag    6780
gatggagtcc agcaccagtt cctggaagcc tgggtcccgg accaccagcc tgtcagatc    6840 tgcacatgcc tcagcgggcg gaaggtcaac tgcacaacgc agccctgccc cacggccaaa    6900
gctcccacgt gtggcctgtg tgaagtagcc cgcctccgcc agaatgcaga ccagtgctgc    6960
cccgagtatg agtgtgtgtg tgaccccagtg agctgtgacc tgcccccagt gcctcactgt    7020
gaacgtggcc tccagcccac actgaccaac cctggcgagt gcagacccaa cttcacctgc    7080
gcctgcagga aggaggagtg caaaagagtg tccccaccct cctgccccc gcaccgtttg    7140 cccaccccttc ggaagaccca gtgctgtgat gagtatgagt gtgcctgcaa ctgtgtcaac    7200
```

-continued

| | |
|---|---|
| tccacagtga gctgtcccct tgggtacttg gcctcaaccg ccaccaatga ctgtggctgt | 7260 |
| accacaacca cctgccttcc cgacaaggtg tgtgtccacc gaagcaccat ctaccctgtg | 7320 |
| ggccagttct ggggaggaggg ctgcgatgtg tgcacctgca ccgacatgga ggatgccgtg | 7380 |
| atgggcctcc gcgtggccca gtgctcccag aagccctgtg aggacagctg tcggtcgggc | 7440 |
| ttcacttacg ttctgcatga aggcgagtgc tgtggaaggt gcctgccatc tgcctgtgag | 7500 |
| gtggtgactg gctcaccgcg gggggactcc cagtcttcct ggaagagtgt cggctcccag | 7560 |
| tgggcctccc cggagaaccc ctgcctcatc aatgagtgtg tccgagtgaa ggaggaggtc | 7620 |
| tttatacaac aaaggaacgt ctcctgcccc cagctggagg tccctgtctg ccctcgggc | 7680 |
| tttcagctga gctgtaagac ctcagcgtgc tgcccaagct gtcgctgtga gcgcatggag | 7740 |
| gcctgcatgc tcaatggcac tgtcattggg cccgggaaga ctgtgatgat cgatgtgtgc | 7800 |
| acgacctgcc gctgcatggt gcaggtgggg gtcatctctg gattcaagct ggagtgcagg | 7860 |
| aagaccacct gcaaccsctg ccccctgggt tacaaggaag aaaataacac aggtgaatgt | 7920 |
| tgtgggagat gtttgcctac ggcttgcacc attcagctaa aggaggacaa gatcatgaca | 7980 |
| ctgaagcgtg atgagacgct ccaggatggc tgtgatactc acttctgcaa ggtcaatgag | 8040 |
| agaggagagt acttctggga aagagggtc acaggctgcc cacctttga tgaacacaag | 8100 |
| tgtctggctg agggaggtaa aattatgaaa attccaggca cctgctgtga cacatgtgag | 8160 |
| gagcctgagt gcaacgacat cactgccagg ctgcagtatg tcaaggtggg aagctgtaag | 8220 |
| tctgaagtag aggtggatat ccactactgc cagggcaaat gtgccagcaa agccatgtac | 8280 |
| tccattgaca tcaacgatgt gcaggaccag tgctcctgct gctctccgac acggacggaa | 8340 |
| cccatgcagg tggccctgca ctgcaccaat ggctctgttg tgtaccatga ggttctcaat | 8400 |
| gccatggagt gcaaatgctc ccccaggaag tgcagcaagt ga | 8442 |

<210> SEQ ID NO 4
<211> LENGTH: 2813
<212> TYPE: PRT
<213> ORGANISM: Homo sapiens

<400> SEQUENCE: 4

Met Ile Pro Ala Arg Phe Ala Gly Val Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

```
Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575
```

-continued

```
Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
            595                 600                 605

Arg Tyr Asp Val Cys Ser Cys Ser Asp Gly Arg Glu Cys Leu Cys Gly
        610                 615                 620

Ala Leu Ala Ser Tyr Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
    850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
        915                 920                 925

Val Glu Gly Gly Glu Ile Glu Leu Phe Asp Gly Glu Val Asn Val Lys
    930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
```

|   |   |   |   |   |   |   |   |   |   |
|---|---|---|---|---|---|---|---|---|---|
| Ser | Ser 1010 | Asn | Leu | Gln 1015 | Val | Glu | Glu | Asp 1020 | Pro | Val | Asp | Phe | Gly | Asn |

Ser Ser Asn Leu Gln Val Glu Glu Asp Pro Val Asp Phe Gly Asn
    1010            1015            1020

Ser Trp Lys Val Ser Ser Gln Cys Ala Asp Thr Arg Lys Val Pro
    1025            1030            1035

Leu Asp Ser Ser Pro Ala Thr Cys His Asn Asn Ile Met Lys Gln
    1040            1045            1050

Thr Met Val Asp Ser Ser Cys Arg Ile Leu Thr Ser Asp Val Phe
    1055            1060            1065

Gln Asp Cys Asn Lys Leu Val Asp Pro Glu Pro Tyr Leu Asp Val
    1070            1075            1080

Cys Ile Tyr Asp Thr Cys Ser Cys Glu Ser Ile Gly Asp Cys Ala
    1085            1090            1095

Cys Phe Cys Asp Thr Ile Ala Ala Tyr Ala His Val Cys Ala Gln
    1100            1105            1110

His Gly Lys Val Val Thr Trp Arg Thr Ala Thr Leu Cys Pro Gln
    1115            1120            1125

Ser Cys Glu Glu Arg Asn Leu Arg Glu Asn Gly Tyr Glu Cys Glu
    1130            1135            1140

Trp Arg Tyr Asn Ser Cys Ala Pro Ala Cys Gln Val Thr Cys Gln
    1145            1150            1155

His Pro Glu Pro Leu Ala Cys Pro Val Gln Cys Val Glu Gly Cys
    1160            1165            1170

His Ala His Cys Pro Pro Gly Lys Ile Leu Asp Glu Leu Leu Gln
    1175            1180            1185

Thr Cys Val Asp Pro Glu Asp Cys Pro Val Cys Glu Val Ala Gly
    1190            1195            1200

Arg Arg Phe Ala Ser Gly Lys Lys Val Thr Leu Asn Pro Ser Asp
    1205            1210            1215

Pro Glu His Cys Gln Ile Cys His Cys Asp Val Val Asn Leu Thr
    1220            1225            1230

Cys Glu Ala Cys Gln Glu Pro Gly Gly Leu Val Val Pro Pro Thr
    1235            1240            1245

Asp Ala Pro Val Ser Pro Thr Thr Leu Tyr Val Glu Asp Ile Ser
    1250            1255            1260

Glu Pro Pro Leu His Asp Phe Tyr Cys Ser Arg Leu Leu Asp Leu
    1265            1270            1275

Val Phe Leu Leu Asp Gly Ser Ser Arg Leu Ser Glu Ala Glu Phe
    1280            1285            1290

Glu Val Leu Lys Ala Phe Val Val Asp Met Met Glu Arg Leu Arg
    1295            1300            1305

Ile Ser Gln Lys Trp Val Arg Val Ala Val Val Glu Tyr His Asp
    1310            1315            1320

Gly Ser His Ala Tyr Ile Gly Leu Lys Asp Arg Lys Arg Pro Ser
    1325            1330            1335

Glu Leu Arg Arg Ile Ala Ser Gln Val Lys Tyr Ala Gly Ser Gln
    1340            1345            1350

Val Ala Ser Thr Ser Glu Val Leu Lys Tyr Thr Leu Phe Gln Ile
    1355            1360            1365

Phe Ser Lys Ile Asp Arg Pro Glu Ala Ser Arg Ile Thr Leu Leu
    1370            1375            1380

Leu Met Ala Ser Gln Glu Pro Gln Arg Met Ser Arg Asn Phe Val
    1385            1390            1395

-continued

Arg Tyr Val Gln Gly Leu Lys Lys Lys Val Ile Val Ile Pro
1400                 1405                1410

Val Gly Ile Gly Pro His Ala Asn Leu Lys Gln Ile Arg Leu Ile
1415                 1420                1425

Glu Lys Gln Ala Pro Glu Asn Lys Ala Phe Val Leu Ser Ser Val
1430                 1435                1440

Asp Glu Leu Glu Gln Gln Arg Asp Glu Ile Val Ser Tyr Leu Cys
1445                 1450                1455

Asp Leu Ala Pro Glu Ala Pro Pro Pro Thr Leu Pro Pro Asp Met
1460                 1465                1470

Ala Gln Val Thr Val Gly Pro Gly Leu Leu Gly Val Ser Thr Leu
1475                 1480                1485

Gly Pro Lys Arg Asn Ser Met Val Leu Asp Val Ala Phe Val Leu
1490                 1495                1500

Glu Gly Ser Asp Lys Ile Gly Glu Ala Asp Phe Asn Arg Ser Lys
1505                 1510                1515

Glu Phe Met Glu Glu Val Ile Gln Arg Met Asp Val Gly Gln Asp
1520                 1525                1530

Ser Ile His Val Thr Val Leu Gln Tyr Ser Tyr Met Val Thr Val
1535                 1540                1545

Glu Tyr Pro Phe Ser Glu Ala Gln Ser Lys Gly Asp Ile Leu Gln
1550                 1555                1560

Arg Val Arg Glu Ile Arg Tyr Gln Gly Gly Asn Arg Thr Asn Thr
1565                 1570                1575

Gly Leu Ala Leu Arg Tyr Leu Ser Asp His Ser Phe Leu Val Ser
1580                 1585                1590

Gln Gly Asp Arg Glu Gln Ala Pro Asn Leu Val Tyr Met Val Thr
1595                 1600                1605

Gly Asn Pro Ala Ser Asp Glu Ile Lys Arg Leu Pro Gly Asp Ile
1610                 1615                1620

Gln Val Val Pro Ile Gly Val Gly Pro Asn Ala Asn Val Gln Glu
1625                 1630                1635

Leu Glu Arg Ile Gly Trp Pro Asn Ala Pro Ile Leu Ile Gln Asp
1640                 1645                1650

Phe Glu Thr Leu Pro Arg Glu Ala Pro Asp Leu Val Leu Gln Arg
1655                 1660                1665

Cys Cys Ser Gly Glu Gly Leu Gln Ile Pro Thr Leu Ser Pro Ala
1670                 1675                1680

Pro Asp Cys Ser Gln Pro Leu Asp Val Ile Leu Leu Leu Asp Gly
1685                 1690                1695

Ser Ser Ser Phe Pro Ala Ser Tyr Phe Asp Glu Met Lys Ser Phe
1700                 1705                1710

Ala Lys Ala Phe Ile Ser Lys Ala Asn Ile Gly Pro Arg Leu Thr
1715                 1720                1725

Gln Val Ser Val Leu Gln Tyr Gly Ser Ile Thr Thr Ile Asp Val
1730                 1735                1740

Pro Trp Asn Val Val Pro Glu Lys Ala His Leu Leu Ser Leu Val
1745                 1750                1755

Asp Val Met Gln Arg Glu Gly Gly Pro Ser Gln Ile Gly Asp Ala
1760                 1765                1770

Leu Gly Phe Ala Val Arg Tyr Leu Thr Ser Glu Met His Gly Ala
1775                 1780                1785

-continued

```
Arg Pro Gly Ala Ser Lys Ala Val Val Ile Leu Val  Thr Asp Val
1790              1795                 1800

Ser Val Asp Ser Val Asp Ala Ala Ala Asp Ala Ala  Arg Ser Asn
1805              1810                 1815

Arg Val Thr Val Phe Pro Ile Gly Ile Gly Asp Arg  Tyr Asp Ala
1820              1825                 1830

Ala Gln Leu Arg Ile Leu Ala Gly Pro Ala Gly Asp  Ser Asn Val
1835              1840                 1845

Val Lys Leu Gln Arg Ile Glu Asp Leu Pro Thr Met  Val Thr Leu
1850              1855                 1860

Gly Asn Ser Phe Leu His Lys Leu Cys Ser Gly Phe  Val Arg Ile
1865              1870                 1875

Cys Met Asp Glu Asp Gly Asn Glu Lys Arg Pro Gly  Asp Val Trp
1880              1885                 1890

Thr Leu Pro Asp Gln Cys His Thr Val Thr Cys Gln  Pro Asp Gly
1895              1900                 1905

Gln Thr Leu Leu Lys Ser His Arg Val Asn Cys Asp  Arg Gly Leu
1910              1915                 1920

Arg Pro Ser Cys Pro Asn Ser Gln Ser Pro Val Lys  Val Glu Glu
1925              1930                 1935

Thr Cys Gly Cys Arg Trp Thr Cys Pro Cys Val Cys  Thr Gly Ser
1940              1945                 1950

Ser Thr Arg His Ile Val Thr Phe Asp Gly Gln Asn  Phe Lys Leu
1955              1960                 1965

Thr Gly Ser Cys Ser Tyr Val Leu Phe Gln Asn Lys  Glu Gln Asp
1970              1975                 1980

Leu Glu Val Ile Leu His Asn Gly Ala Cys Ser Pro  Gly Ala Arg
1985              1990                 1995

Gln Gly Cys Met Lys Ser Ile Glu Val Lys His Ser  Ala Leu Ser
2000              2005                 2010

Val Glu Leu His Ser Asp Met Glu Val Thr Val Asn  Gly Arg Leu
2015              2020                 2025

Val Ser Val Pro Tyr Val Gly Gly Asn Met Glu Val  Asn Val Tyr
2030              2035                 2040

Gly Ala Ile Met His Glu Val Arg Phe Asn His Leu  Gly His Ile
2045              2050                 2055

Phe Thr Phe Thr Pro Gln Asn Asn Glu Phe Gln Leu  Gln Leu Ser
2060              2065                 2070

Pro Lys Thr Phe Ala Ser Lys Thr Tyr Gly Leu Cys  Gly Ile Cys
2075              2080                 2085

Asp Glu Asn Gly Ala Asn Asp Phe Met Leu Arg Asp  Gly Thr Val
2090              2095                 2100

Thr Thr Asp Trp Lys Thr Leu Val Gln Glu Trp Thr  Val Gln Arg
2105              2110                 2115

Pro Gly Gln Thr Cys Gln Pro Ile Leu Glu Glu Gln  Cys Leu Val
2120              2125                 2130

Pro Asp Ser Ser His Cys Gln Val Leu Leu Pro Leu  Phe Ala
2135              2140                 2145

Glu Cys His Lys Val Leu Ala Pro Ala Thr Phe Tyr  Ala Ile Cys
2150              2155                 2160

Gln Gln Asp Ser Cys His Gln Glu Gln Val Cys Glu  Val Ile Ala
2165              2170                 2175

Ser Tyr Ala His Leu Cys Arg Thr Asn Gly Val Cys  Val Asp Trp
```

-continued

```
            2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580
```

```
Leu Asn Gly Thr Val Ile Gly Pro Gly Lys Thr Val Met Ile Asp
        2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
    2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 5
<211> LENGTH: 1444
<212> TYPE: PRT
<213> ORGANISM: Artificial Sequence
<220> FEATURE:
<223> OTHER INFORMATION: Single Chain Factor VIII

<400> SEQUENCE: 5

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110
```

-continued

Glu Tyr Asp Asp Gln Thr Ser Gln Arg Glu Lys Glu Asp Lys Val
         115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
                180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
                340                 345                 350

Ser Glu Met Asp Val Val Arg Phe Asp Asp Asp Asn Ser Pro Ser Phe
        355                 360                 365

Ile Gln Ile Arg Ser Val Ala Lys Lys His Pro Lys Thr Trp Val His
        370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

```
Leu Thr Arg Tyr Tyr Ser Ser Phe Val Asn Met Glu Arg Asp Leu Ala
530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Thr Thr Leu Gln
        755                 760                 765

Ser Asp Gln Glu Glu Ile Asp Tyr Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
                805                 810                 815

Arg Leu Trp Asp Tyr Gly Met Ser Ser Ser Pro His Val Leu Arg Asn
            820                 825                 830

Arg Ala Gln Ser Gly Ser Val Pro Gln Phe Lys Lys Val Val Phe Gln
        835                 840                 845

Glu Phe Thr Asp Gly Ser Phe Thr Gln Pro Leu Tyr Arg Gly Glu Leu
850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
        915                 920                 925

Trp Lys Val Gln His His Met Ala Pro Thr Lys Asp Glu Phe Asp Cys
930                 935                 940

Lys Ala Trp Ala Tyr Phe Ser Asp Val Asp Leu Glu Lys Asp Val His
```

-continued

```
945                 950                 955                 960
Ser Gly Leu Ile Gly Pro Leu Val Cys His Thr Asn Thr Leu Asn
                965                 970                 975
Pro Ala His Gly Arg Gln Val Thr Val Gln Glu Phe Ala Leu Phe Phe
                980                 985                 990
Thr Ile Phe Asp Glu Thr Lys Ser Trp Tyr Phe Thr Glu Asn Met Glu
                995                1000                1005
Arg Asn Cys Arg Ala Pro Cys Asn Ile Gln Met Glu Asp Pro Thr
       1010                1015                1020
Phe Lys Glu Asn Tyr Arg Phe His Ala Ile Asn Gly Tyr Ile Met
       1025                1030                1035
Asp Thr Leu Pro Gly Leu Val Met Ala Gln Asp Gln Arg Ile Arg
       1040                1045                1050
Trp Tyr Leu Leu Ser Met Gly Ser Asn Glu Asn Ile His Ser Ile
       1055                1060                1065
His Phe Ser Gly His Val Phe Thr Val Arg Lys Lys Glu Glu Tyr
       1070                1075                1080
Lys Met Ala Leu Tyr Asn Leu Tyr Pro Gly Val Phe Glu Thr Val
       1085                1090                1095
Glu Met Leu Pro Ser Lys Ala Gly Ile Trp Arg Val Glu Cys Leu
       1100                1105                1110
Ile Gly Glu His Leu His Ala Gly Met Ser Thr Leu Phe Leu Val
       1115                1120                1125
Tyr Ser Asn Lys Cys Gln Thr Pro Leu Gly Met Ala Ser Gly His
       1130                1135                1140
Ile Arg Asp Phe Gln Ile Thr Ala Ser Gly Gln Tyr Gly Gln Trp
       1145                1150                1155
Ala Pro Lys Leu Ala Arg Leu His Tyr Ser Gly Ser Ile Asn Ala
       1160                1165                1170
Trp Ser Thr Lys Glu Pro Phe Ser Trp Ile Lys Val Asp Leu Leu
       1175                1180                1185
Ala Pro Met Ile Ile His Gly Ile Lys Thr Gln Gly Ala Arg Gln
       1190                1195                1200
Lys Phe Ser Ser Leu Tyr Ile Ser Gln Phe Ile Ile Met Tyr Ser
       1205                1210                1215
Leu Asp Gly Lys Lys Trp Gln Thr Tyr Arg Gly Asn Ser Thr Gly
       1220                1225                1230
Thr Leu Met Val Phe Phe Gly Asn Val Asp Ser Ser Gly Ile Lys
       1235                1240                1245
His Asn Ile Phe Asn Pro Pro Ile Ile Ala Arg Tyr Ile Arg Leu
       1250                1255                1260
His Pro Thr His Tyr Ser Ile Arg Ser Thr Leu Arg Met Glu Leu
       1265                1270                1275
Met Gly Cys Asp Leu Asn Ser Cys Ser Met Pro Leu Gly Met Glu
       1280                1285                1290
Ser Lys Ala Ile Ser Asp Ala Gln Ile Thr Ala Ser Ser Tyr Phe
       1295                1300                1305
Thr Asn Met Phe Ala Thr Trp Ser Pro Ser Lys Ala Arg Leu His
       1310                1315                1320
Leu Gln Gly Arg Ser Asn Ala Trp Arg Pro Gln Val Asn Asn Pro
       1325                1330                1335
Lys Glu Trp Leu Gln Val Asp Phe Gln Lys Thr Met Lys Val Thr
       1340                1345                1350
```

```
Gly Val Thr Thr Gln Gly Val Lys Ser Leu Leu Thr Ser Met Tyr
    1355            1360                1365

Val Lys Glu Phe Leu Ile Ser Ser Ser Gln Asp Gly His Gln Trp
1370            1375                1380

Thr Leu Phe Phe Gln Asn Gly Lys Val Lys Val Phe Gln Gly Asn
    1385            1390                1395

Gln Asp Ser Phe Thr Pro Val Val Asn Ser Leu Asp Pro Pro Leu
    1400            1405                1410

Leu Thr Arg Tyr Leu Arg Ile His Pro Gln Ser Trp Val His Gln
    1415            1420                1425

Ile Ala Leu Arg Met Glu Val Leu Gly Cys Glu Ala Gln Asp Leu
    1430            1435                1440

Tyr

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
        580                 585

<210> SEQ ID NO 7
<211> LENGTH: 519
<212> TYPE: PRT
<213> ORGANISM: Artificial sequence
<220> FEATURE:
<223> OTHER INFORMATION: His-tagged D'D3
<220> FEATURE:
<221> NAME/KEY: MISC_FEATURE
<222> LOCATION: (1)..(479)
<223> OTHER INFORMATION: Amino acid sequence of D'D3 - His8
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(511)
```

<223> OTHER INFORMATION: glycine / serine linker
<220> FEATURE:
<221> NAME/KEY: MISC_FEATURE
<222> LOCATION: (512)..(519)
<223> OTHER INFORMATION: polyhistidine tag

<400> SEQUENCE: 7

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
370                 375                 380
```

```
Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Ser
465                 470                 475                 480

Ser Gly Gly Ser Gly Gly Ser Gly Gly Ser Gly Gly Ser Gly Gly Ser
                485                 490                 495

Gly Gly Ser Gly Gly Ser Gly Gly Ser Gly Gly Ser Gly Gly Ser His
            500                 505                 510

His His His His His His
        515
```

<210> SEQ ID NO 8
<211> LENGTH: 584
<212> TYPE: PRT
<213> ORGANISM: Artificial sequence
<220> FEATURE:
<223> OTHER INFORMATION: His-tagged CTP fusion protein
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(511)
<223> OTHER INFORMATION: glycine / serine linker
<220> FEATURE:
<221> NAME/KEY: MISC_FEATURE
<222> LOCATION: (512)..(576)
<223> OTHER INFORMATION: C-terminal peptide of human chorionic
      gonadotropin beta subunit
<220> FEATURE:
<221> NAME/KEY: MISC_FEATURE
<222> LOCATION: (577)..(584)
<223> OTHER INFORMATION: Polyhistidin tag

<400> SEQUENCE: 8

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125
```

```
Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
                180                 185                 190

Val Glu Ser Gly Arg Tyr Ile Ile Leu Leu Gly Lys Ala Leu Ser
                195                 200                 205

Val Val Trp Asp Arg His Leu Ser Ile Ser Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
                260                 265                 270

Lys Val Pro Leu Asp Ser Ser Pro Ala Thr Cys His Asn Asn Ile Met
            275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
                340                 345                 350

Lys Val Val Thr Trp Arg Thr Ala Thr Leu Cys Pro Gln Ser Cys Glu
                355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
            435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Gly Gly Ser Gly Gly Ser Gly Gly Ser Gly Gly Ser Gly Gly Ser Gly
                485                 490                 495

Gly Ser Gly Gly Ser Gly Gly Ser Gly Gly Ser Gly Ser Ser Ala
                500                 505                 510

Ser Ser Ser Ser Lys Ala Pro Pro Pro Ser Leu Pro Ser Pro Ser Arg
                515                 520                 525

Leu Pro Gly Pro Ser Asp Thr Pro Ile Leu Pro Gln Ala Ser Ser Ser
    530                 535                 540

Ser Lys Ala Pro Pro Pro Ser Leu Pro Ser Pro Ser Arg Leu Pro Gly
```

```
545                 550                 555                 560
Pro Ser Asp Thr Pro Ile Leu Pro Gln Ala Gly Gly Ser Gly Gly Ser
                565                 570                 575
His His His His His His His His
            580
```

US 10,688,157 B2

TRUNCATED VON WILLEBRAND FACTOR POLYPEPTIDES FOR TREATING HEMOPHILIA

This application is the United States national stage entry under 35 U.S.C. § 371 of International Application No. PCT/EP2016/061443, filed on May 20, 2016 and published as WO 2016/188907 A1, which claims priority to European Patent Application Nos. 15168930.4, filed on May 22, 2015, and 16163239.3, filed on Mar. 31, 2016. The contents of these applications are each incorporated herein by reference in their entirety.

FIELD OF THE INVENTION

The present invention relates to products and methods for improving treatment of blood coagulation disorders.

BACKGROUND OF THE INVENTION

There are various bleeding disorders caused by deficiencies of blood coagulation factors.

The most common disorders are hemophilia A and B, resulting from deficiencies of blood coagulation Factor VIII (FVIII) and IX, respectively. Another known bleeding disorder is von Willebrand's disease (VWD).

In plasma FVIII exists mostly as a noncovalent complex with von Willebrand Factor (VWF), and its coagulant function is to accelerate Factor IXa dependent conversion of Factor X to Xa.

Classic hemophilia or hemophilia A is an inherited bleeding disorder. It results from a chromosome X-linked deficiency of blood coagulation FVIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children having been diagnosed for hemophilia A.

It would thus be highly desirable to increase the half-life of FVIII so that pharmaceutical compositions containing such FVIII would have to be administered less frequently.

Several attempts have been made to prolong the half-life of non-activated FVIII either by reducing its interaction with cellular receptors (WO 03/093313 A2, WO 02/060951 A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801) The increased half-life of pegylated VWF would indirectly also enhance the half-life of FVIII present in plasma. Also fusion proteins of FVIII have been described (WO 2004/101740, WO2008/077616 and WO 2009/156137).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc. Natl. Acad. Sci. USA 84:4393-4397. The precursor polypeptide, pre-pro-VWF, consists of an N-terminal 22-residue signal peptide, followed by a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus.

Once secreted into plasma the protease ADAMTS13 can cleave high-molecular weight VWF multimers within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

In plasma FVIII binds with high affinity to VWF, which protects it from premature elimination and thus, plays in addition to its role in primary hemostasis a crucial role to stabilize FVIII, regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 2 to 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol 9:1233-1242).

VWF-derived polypeptides, in particular VWF fragments, have been described to stabilize FVIII in vitro and in vivo. WO 2013/106787 A1 is directed at chimeric proteins comprising certain VWF fragments and a FVIII protein. Those chimeric hetero-dimers of FVIII and VWF-fragment do have a fixed molar ratio of VWF to FVIII of 1:1. WO 2014/198699 A2 and WO 2013/083858 A2 describe VWF fragments and their use in the treatment of hemophilia. It was found that bioavailability of FVIIIs may be significantly improved upon extravascular co-administration with similar molar amounts of VWF fragments. High molar excess of VWF over FVIII was said to be not desirable, and in experiments with VWF fragments co-administered s.c. with FVIII it was found that the VWF dose was not critical for FVIII bioavailability. Thus molar ratios of VWF fragments over FVIII were limited to maximally 50:1 and preferred ranges to maximally 1.5:1. WO 2011/060242 A2 discloses fusion polypeptides comprising certain VWF fragments and an antibody Fc region proposing specific molar ratios of VWF fragment over FVIII of up to 10:1. WO2013/093760 A2 describes a method for preparing a protein, comprising co-expressing FVIII or VWF polypeptides, including truncated forms of VWF, with a recombinant α-2,3-sialyltransferase. Yee et al. (2014) Blood 124(3):445-452 found that a VWF fragment containing the D'D3 domains is sufficient to stabilize Factor VIII in VWF-deficient mice. However, although a VWF D'D3-Fc fusion protein exhibited markedly prolonged survival when transfused into FVIII-deficient mice, the VWF D'D3-Fc fusion protein did not prolong the survival of co-transfused FVIII. The prior art is silent as to the benefit of exceeding certain ratios of administered VWF fragments over endogenous VWF for the purpose of prolonging the in vivo half-life of co-administered FVIII.

There is an ongoing need for methods increasing the half-life of FVIII and FVIII products with reduced administration frequency.

SUMMARY OF THE INVENTION

It has been found by the inventors that the in vivo half-life of Factor VIII can be prolonged by co-administration of a high molar excess of a truncated VWF polypeptide (polypeptide of the invention). The truncated VWF preferably comprises a half-life extending moiety. The high molar excess may be relative to the concentration of co-administered Factor VIII or relative to the concentration of endogenous VWF present in the treated subject. Without wishing to be bound to any theory, it is believed that it is important to achieve a high surplus of the administered truncated VWF and preferably the half-life-extended truncated VWF to minimize the binding of the co-administered FVIII to the endogenous VWF which has a larger molecular structure probably leading to an increased catabolism as compared to the truncated VWF. This technical effect is even more pronounced if the truncated VWF is not only administered in a ratio above 50 over a co-administered Factor VIII but also comprises a half-life extending moiety.

The present invention therefore relates to the following embodiments [1] to [73]:

[1] A polypeptide comprising a truncated von Willebrand Factor (VWF) for use in the treatment of a blood coagulation disorder, said treatment comprising administering to a subject having endogenous VWF the polypeptide and a Factor VIII (FVIII), wherein the polypeptide is capable of binding to said FVIII, and wherein the molar ratio of the polypeptide to be administered to the FVIII to be administered is greater than 50.

[2] The polypeptide for use according to item [1], wherein the molar ratio of the polypeptide to be administered to the FVIII to be administered is greater than 100.

[3] The polypeptide for use according to item [1], wherein the molar ratio of the polypeptide to be administered to the FVIII to be administered is at least 200.

[4] The polypeptide for use according to item [1], wherein the molar ratio of the polypeptide to be administered to the FVIII to be administered is at least 300.

[5] The polypeptide for use according to item [1], wherein the molar ratio of the polypeptide to be administered to the FVIII to be administered is at least 400.

[6] The polypeptide for use according to item [1], wherein the molar ratio of the polypeptide to be administered to the FVIII to be administered is at least 500.

[7] The polypeptide for use according to any one of items [1] to [6], wherein the molar ratio of the polypeptide administered to the endogenous VWF is greater than 0.5.

[8] The polypeptide for use according to any one of items [1] to [6], wherein the molar ratio of the polypeptide administered to the endogenous VWF is greater than 1.

[9] The polypeptide for use according to any one of items [1] to [6], wherein the molar ratio of the polypeptide administered to the endogenous VWF is greater than 2.

[10] The polypeptide for use according to any one of items [1] to [6], wherein the molar ratio of the polypeptide administered to the endogenous VWF is greater than 4.

[11] The polypeptide for use according to any one of items [1] to [6], wherein the molar ratio of the polypeptide administered to the endogenous VWF is greater than 5.

[12] The polypeptide for use according to any one of items [1] to [6], wherein the molar ratio of the polypeptide administered to the endogenous VWF is greater than 7.

[13] The polypeptide for use according to any one of items [1] to [6], wherein the molar ratio of the polypeptide administered to the endogenous VWF is greater than 10.

[14] The polypeptide for use according to any one of items [1] to [6], wherein the molar ratio of the polypeptide administered to the endogenous VWF is greater than 25.

[15] The polypeptide for use according to any one of items [1] to [6], wherein the molar ratio of the polypeptide administered to the endogenous VWF is greater than 50.

[16] A polypeptide comprising a truncated von Willebrand Factor (VWF) for use in the treatment of a blood coagulation disorder, said treatment comprising administering to a subject having endogenous VWF the polypeptide and a Factor VIII (FVIII), wherein the polypeptide is capable of binding to said FVIII, and wherein the molar ratio of the polypeptide administered to the endogenous VWF is greater than 0.5.

[17] The polypeptide for use according to item [16], wherein the molar ratio of the polypeptide to be administered to the FVIII to be administered is greater than 10.

[18] The polypeptide for use according to item [16], wherein the molar ratio of the polypeptide to be administered to the FVIII to be administered is greater than 20.

[19] The polypeptide for use according to item [16], wherein the molar ratio of the polypeptide to be administered to the FVIII to be administered is greater than 40.

[20] The polypeptide for use according to item [16], wherein the molar ratio of the polypeptide to be administered to the FVIII to be administered is greater than 50.

[21] The polypeptide for use according to item [16], wherein the molar ratio of the polypeptide to be administered to the FVIII to be administered is greater than 100.

[22] The polypeptide for use according to any one of the preceding items, which binds to the FVIII with an affinity characterized by a dissociation constant $K_D$ of less than 1 nM.

[23] The polypeptide for use according to item [22], wherein the $K_D$ ranges from 1 pM to 500 pM.

[24] The polypeptide for use according to item [22], wherein the $K_D$ ranges from 10 pM to 200 pM.

[25] The polypeptide for use according to item [22], wherein the $K_D$ ranges from 60 pM to 100 pM.

[26] The polypeptide for use according to any one of the preceding items, wherein the polypeptide is administered intravenously.

[27] The polypeptide for use according to any one of items [1] to [25], wherein the polypeptide is administered subcutaneously.

[28] The polypeptide for use according to any one of items [1] to [25], wherein the polypeptide is administered intramuscularly.

[29] The polypeptide for use according to any one of the preceding items, wherein the truncated VWF comprises (a) amino acids 776 to 805 of SEQ ID NO:4 or (b) an amino acid sequence having a sequence identity of at least 90% to amino acids 776 to 805 of SEQ ID NO:4.

[30] The polypeptide for use according to any one of the preceding items, wherein the truncated VWF comprises (a) amino acids 766 to 864 of SEQ ID NO:4 or (b) an amino acid sequence having a sequence identity of at least 90% to amino acids 766 to 864 of SEQ ID NO:4.

[31] The polypeptide for use according to any one of the preceding items, wherein the truncated VWF comprises amino acids 764 to 1242 of SEQ ID NO:4.

[32] The polypeptide for use according to any one of the preceding items, wherein the truncated VWF consists of (a) amino acids 764 to 1242 of SEQ ID NO:4, (b) an amino acid sequence having a sequence identity of at least 90% to amino acids 764 to 1242 of SEQ ID NO:4, or (c) a fragment of (a) or (b).

[33] The polypeptide for use according to any one of the preceding items, wherein the truncated VWF lacks amino acids 1243 to 2813 of SEQ ID NO:4.

[34] The polypeptide for use according to any of the proceeding claims, wherein the polypeptide comprises a half-life extending moiety.

[35] The polypeptide for use according to item [34], wherein said half-life extending moiety is a heterologous amino acid sequence fused to the truncated VWF.

[36] The polypeptide for use according to item [35], wherein said heterologous amino acid sequence comprises or consists of a polypeptide selected from the group consisting of immunoglobulin constant regions and portions thereof, e.g. the Fc fragment, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, and combinations thereof.

[37] The polypeptide for use according to any one of items [34], wherein said half-life-extending moiety is conjugated to the polypeptide.

[38] The polypeptide for use according to item [37], wherein said half-life-extending moiety is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains, and combinations thereof.

[39] The polypeptide for use according to any one of the preceding items, wherein the polypeptide is a glycoprotein comprising N-glycans, and wherein at least 75% of said N-glycans comprise, on average, at least one sialic acid moiety.

[40] The polypeptide for use according to item [39], wherein at least 85% of said N-glycans comprise, on average, at least one sialic acid moiety.

[41] The polypeptide for use according to items [39], wherein at least 95% of said N-glycans comprise, on average, at least one sialic acid moiety.

[42] The polypeptide for use according to any one of preceding items wherein the polypeptide comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

[43] The polypeptide for use according to any one of the preceding items wherein the polypeptide comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

[44] The polypeptide for use according to any one of the preceding items, wherein the polypeptide is a dimer.

[45] The polypeptide for use according to item [44], wherein the two monomers forming the dimer are covalently linked to each other via one or more disulfide bridges formed by cysteine residues within the truncated VWF.

[46] The polypeptide for use according to item [45], wherein the cysteine residues forming the one or more disulfide bridges is/are selected from the group consisting of Cys-1099, Cys-1142, Cys-1222, Cys-1225, Cys-1227 and combinations thereof, wherein the amino acid numbering refers to SEQ ID NO:4.

[47] The polypeptide for use according to any one of items [44] to [46], wherein the affinity of said dimer to the FVIII is greater than the affinity of a monomeric polypeptide to said FVIII, said monomeric polypeptide having the same amino acid sequence as a monomeric subunit of the dimeric polypeptide.

[48] The polypeptide for use according to any one of the preceding items, wherein the mean residence time (MRT) and/or the terminal half-life of the FVIII is increased by the co-administration of the polypeptide as compared to a reference treatment, wherein said reference treatment is identical to said treatment, except that the polypeptide and the FVIII are administered in equimolar amounts in said reference treatment.

[49] The polypeptide for use according to item [48], wherein said increase in MRT and/or terminal half-life is at least 50%.

[50] The polypeptide for use according to any one of the preceding items, wherein the mean residence time (MRT) and/or terminal half-life of the FVIII is increased by the co-administration of the polypeptide as compared to a reference treatment with the FVIII alone.

[51] The polypeptide for use according to item [50], wherein said increase in MRT and/or terminal half-life is at least 50%.

[52] The polypeptide for use according to item [50], wherein said increase in MRT and/or terminal half-life is at least 100%.

[53] The polypeptide for use according to any one of the preceding items, wherein the clearance of the FVIII is decreased by the co-administration of the polypeptide as compared to a reference treatment with the FVIII alone.

[54] The polypeptide for use according to any one of the preceding items, wherein the clearance of the FVIII is decreased by the co-administration of the polypeptide as compared to a reference treatment, wherein said reference treatment is identical to said treatment, except that the polypeptide and the FVIII are administered in equimolar amounts in said reference treatment.

[55] The polypeptide for use according to item [53] or [54], wherein said decrease is at least 25%.

[56] The polypeptide for use according to item [53] or [54], wherein said decrease is at least 50%.

[57] The polypeptide for use according to item [53] or [54], wherein said decrease is at least 100%.

[58] The polypeptide for use according to any one of the preceding items, wherein the in vivo recovery of the FVIII is increased by the co-administration of the polypeptide as compared to a reference treatment with the FVIII alone.

[59] The polypeptide for use according to any one of the preceding items, wherein the frequency of administration of the FVIII is reduced as compared to a treatment with the FVIII alone.

[60] The polypeptide for use according to any one of the preceding items, wherein the MRT and/or plasma half-life of the polypeptide is greater than that of a reference polypeptide, wherein said reference polypeptide is endogenous VWF.

[61] The polypeptide for use according to any one of the preceding items, wherein the MRT and/or plasma half-life of the polypeptide is greater than that of a reference polypeptide that is identical to said polypeptide except that it lacks the half-life extending moiety.

[62] The polypeptide for use according to item [60] or [61], wherein the MRT and/or plasma half-life of the polypeptide is at least 25% greater than that of the reference polypeptide.

[63] The polypeptide for use according to item [60] or [61], wherein the MRT and/or plasma half-life of the polypeptide is at least 50% greater than that of the reference polypeptide.

[64] The polypeptide for use according to item [60] or [61], wherein the MRT and/or plasma half-life of the polypeptide is at least 75% greater than that of the reference polypeptide.

[65] The polypeptide for use according to item [60] or [61], wherein the MRT and/or plasma half-life of the polypeptide is at least 100% greater than that of the reference polypeptide.

[66] The polypeptide for use according to any one of the preceding items, wherein the subject is a human.

[67] A pharmaceutical composition comprising (i) a FVIII and (ii) a polypeptide as defined in any one of items [1] to [66], wherein the molar ratio of the polypeptide to the FVIII in the composition is greater than 50.

[68] A pharmaceutical composition comprising (i) a FVIII and (ii) a polypeptide as defined in any one of the items [1] to [66] for use in the treatment of a blood coagulation disorder, said treatment comprising administering to a subject having endogenous VWF the polypeptide and the FVIII, wherein the molar ratio of the polypeptide administered to the endogenous VWF is greater than 0.5.

[69] A pharmaceutical kit comprising (i) a FVIII and (ii) a polypeptide as defined in any one of items [1] to [66] for simultaneous, separate or sequential use in the treatment of a blood coagulation disorder, said treatment comprising administering to a subject having endogenous VWF the polypeptide and the FVIII, wherein the molar ratio of the polypeptide administered to the endogenous VWF is greater than 0.5.

[70] A pharmaceutical kit comprising (i) a FVIII and (ii) a polypeptide as defined in any one of items [1] to [66] for simultaneous, separate or sequential use in the treatment of a blood coagulation disorder, wherein the molar ratio of the polypeptide to be administered to the FVIII to be administered is greater than 50.

[71] The use of a polypeptide as defined in any one of items [1] to [66] for improving the plasma half-life of Factor VIII, and/or for reducing the frequency of administration of Factor VIII.

[72] A method of treating a blood coagulation disorder, comprising administering to a patient having endogenous VWF an effective amount of a polypeptide as defined in any one of items [1] to [66] and a FVIII, wherein the molar ratio of the polypeptide administered to the endogenous VWF immediately after administration of the polypeptide is greater than 0.5. [73] A method of treating a blood coagulation disorder, comprising administering to a patient having endogenous VWF an effective amount of a polypeptide as defined in any one of items [1] to [66] and a FVIII, wherein the molar ratio of the polypeptide to be administered to the Factor VIII to be administered is greater than 50.

Abbreviation: rVIII-SC: rVIII-SingleChain

Figure 2A:
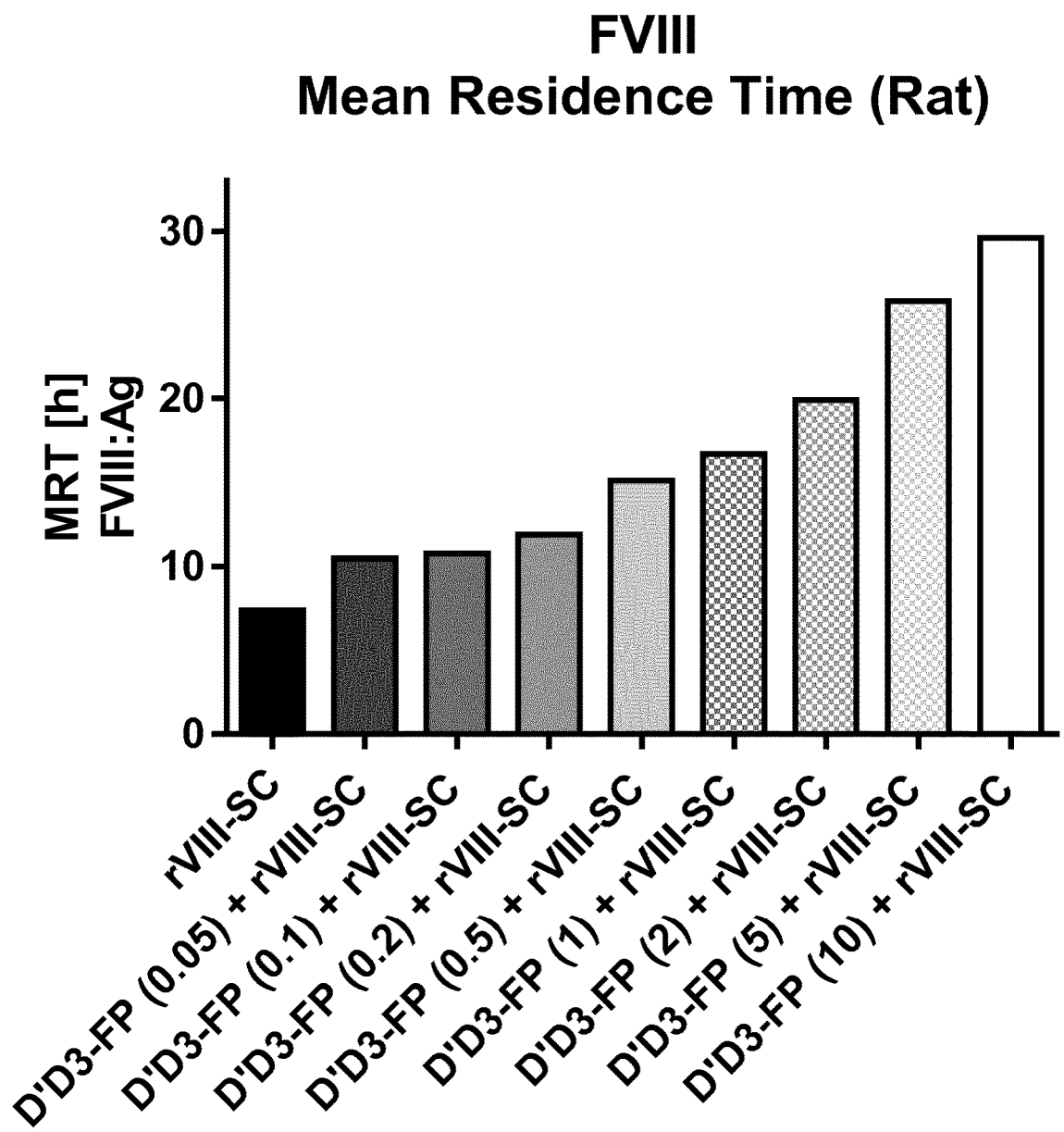
Figure 2B:
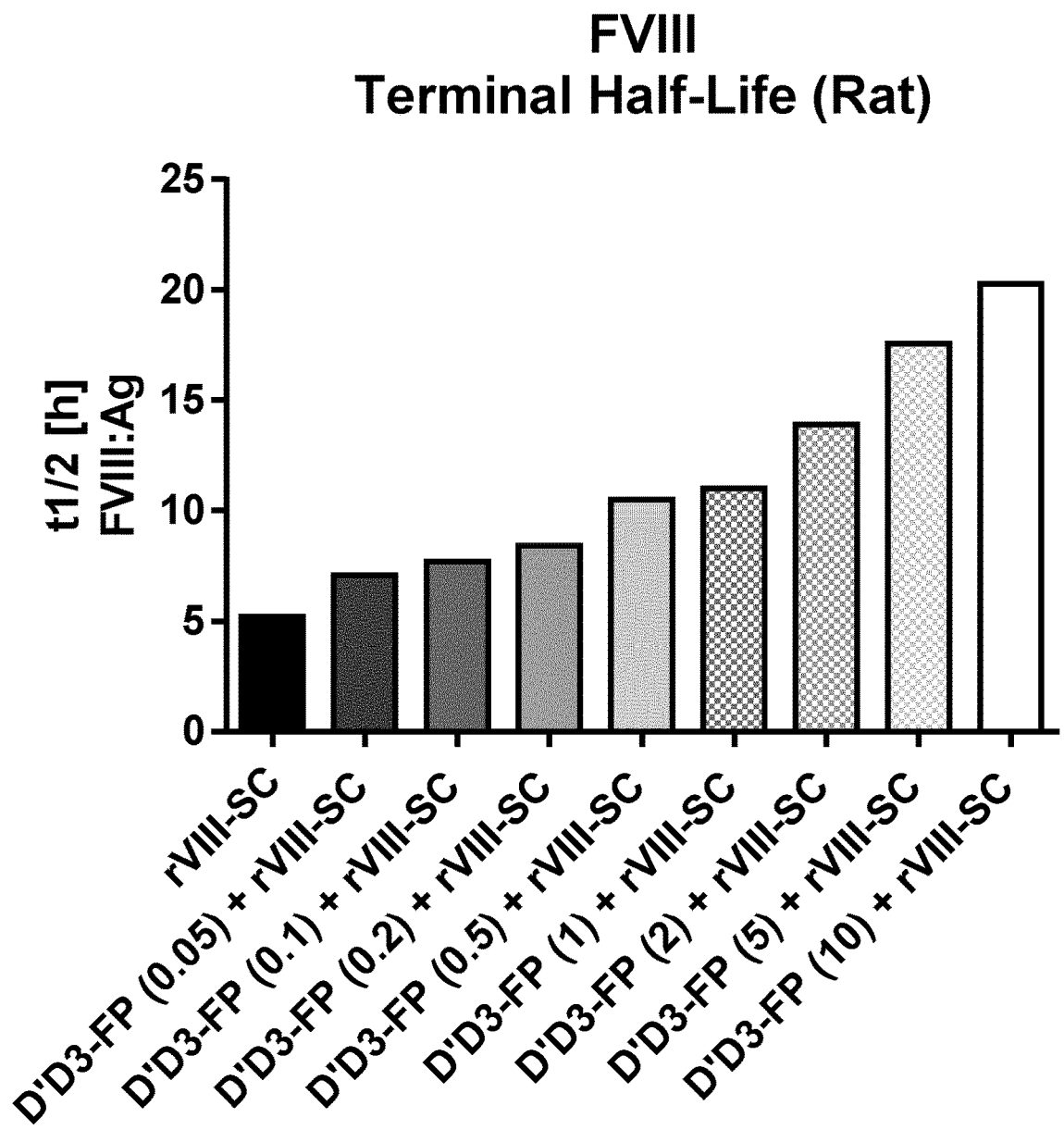
Figure 2C:
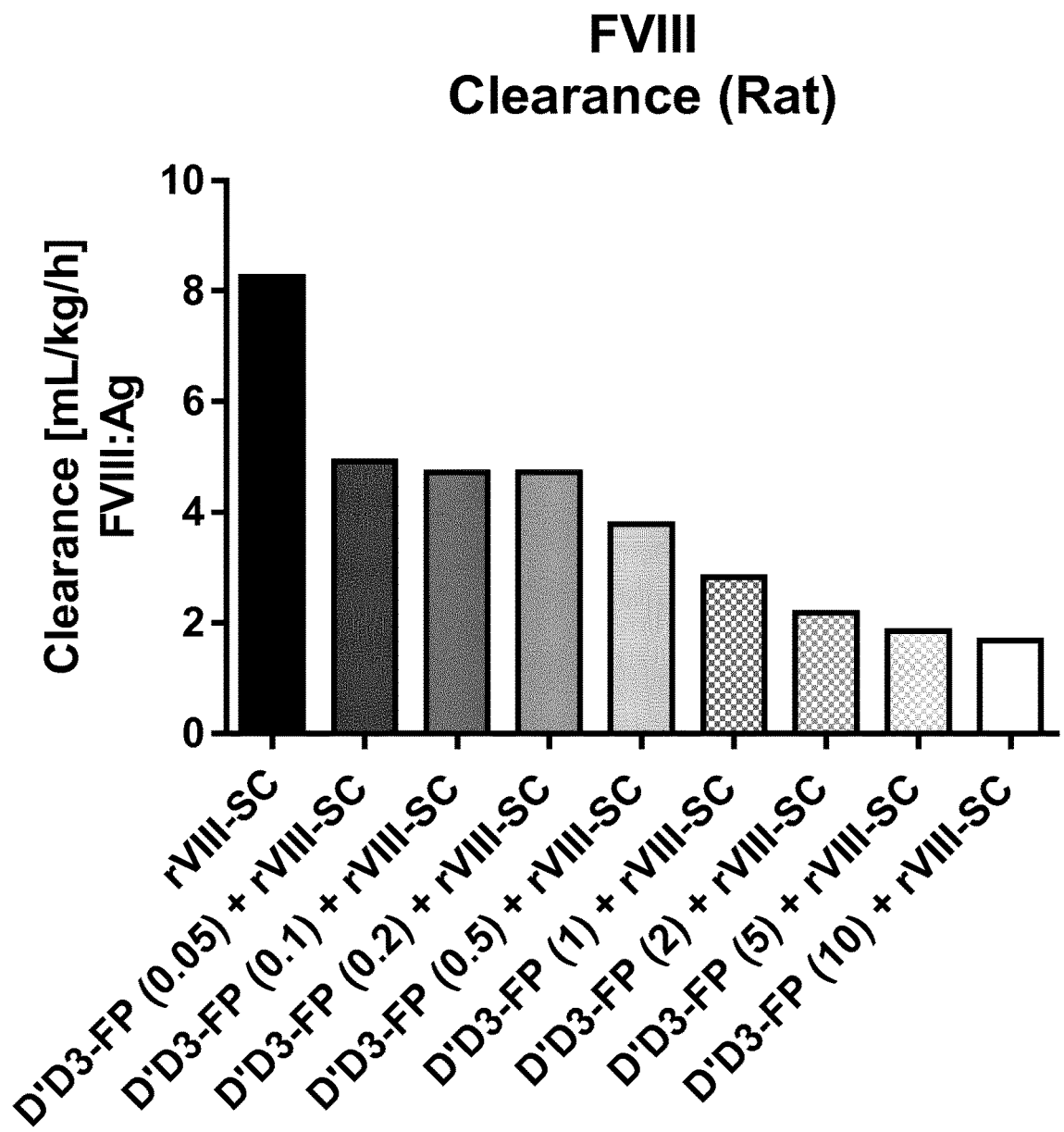

FIG. 2: Mean residence time, terminal half-life and clearance (mean) of rVIII-SingleChain quantified by determining FVIII antigen in rats (Example 1).

Abbreviation: rVIII-SC: rVIII-SingleChain

Figure 3A:
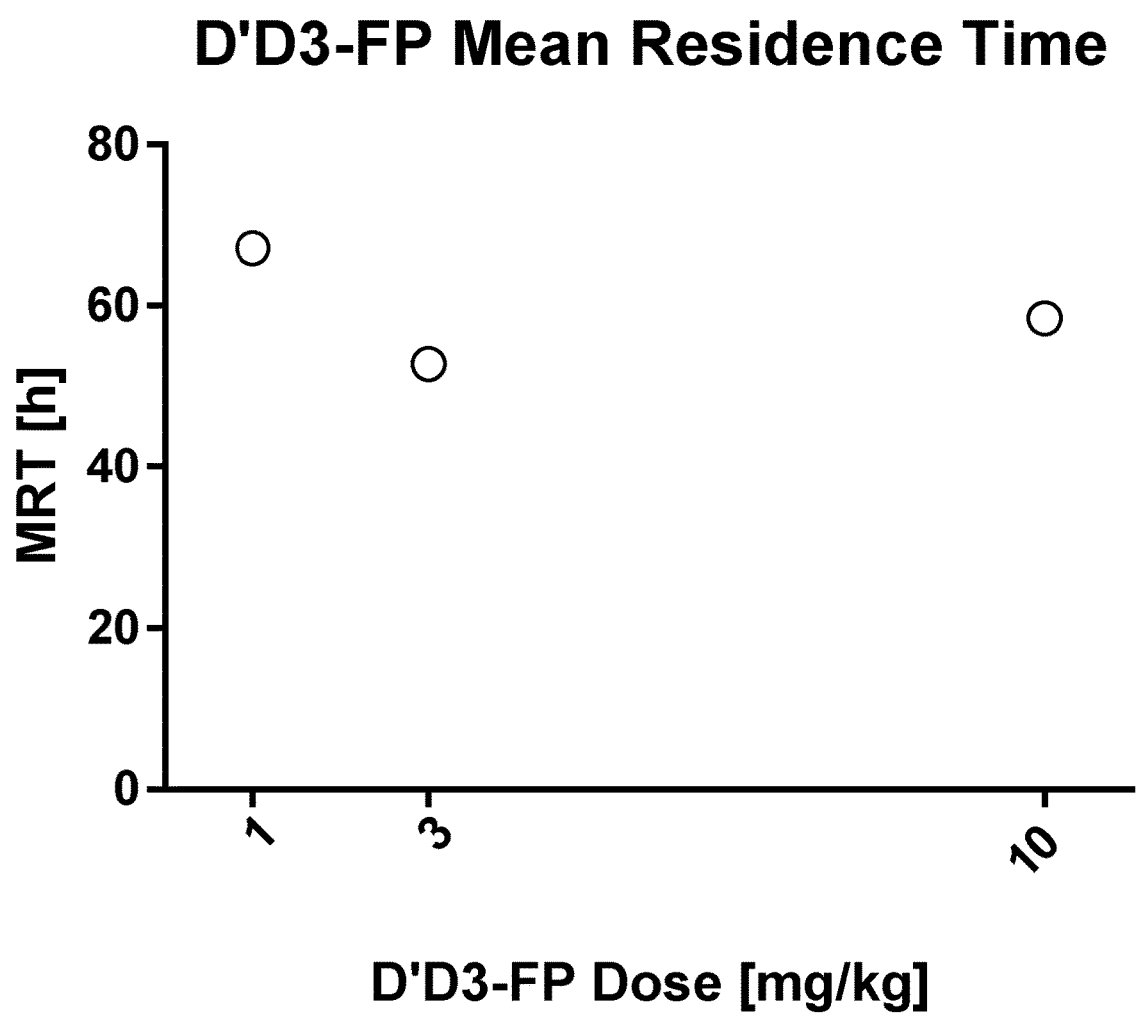
Figure 3B:
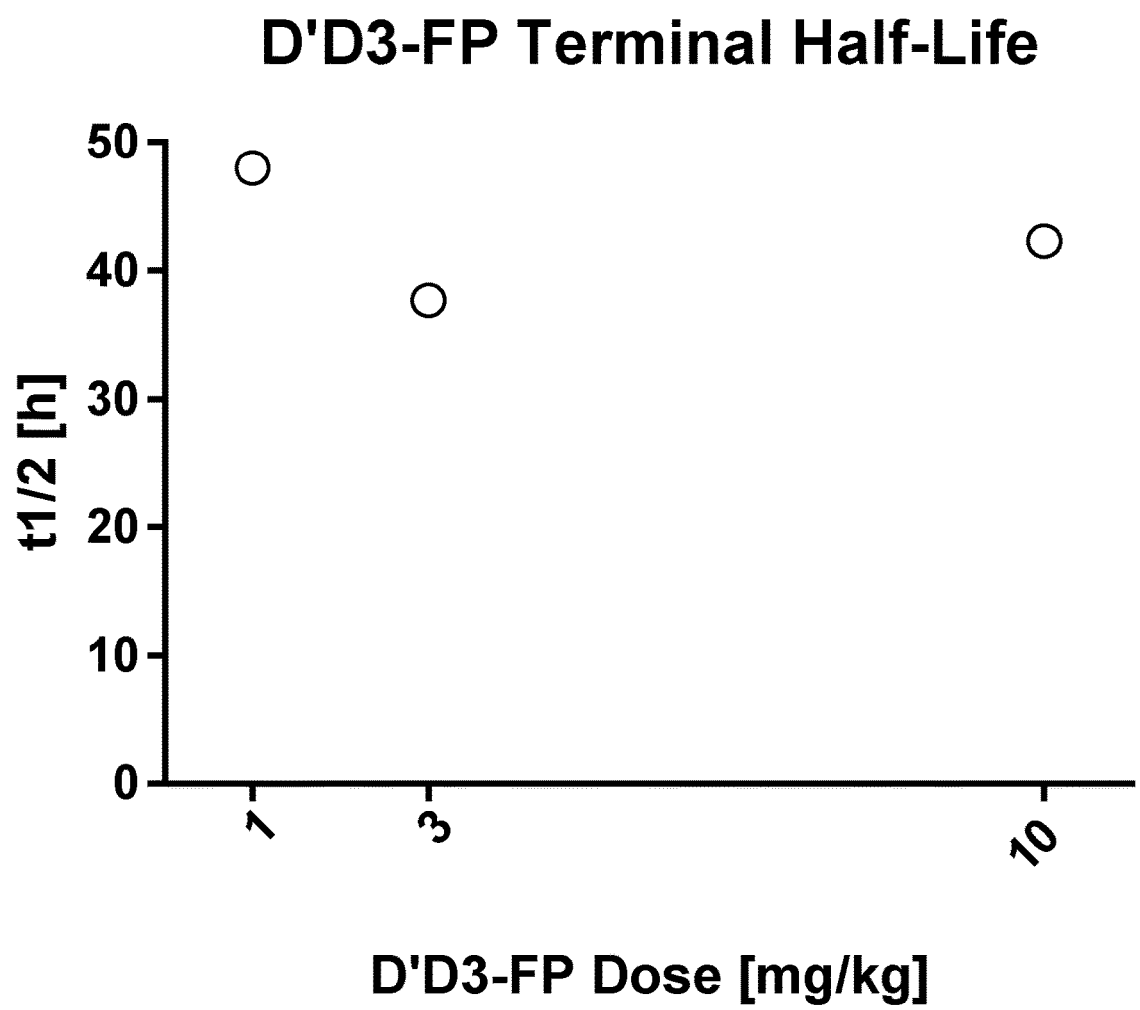
Figure 3C:
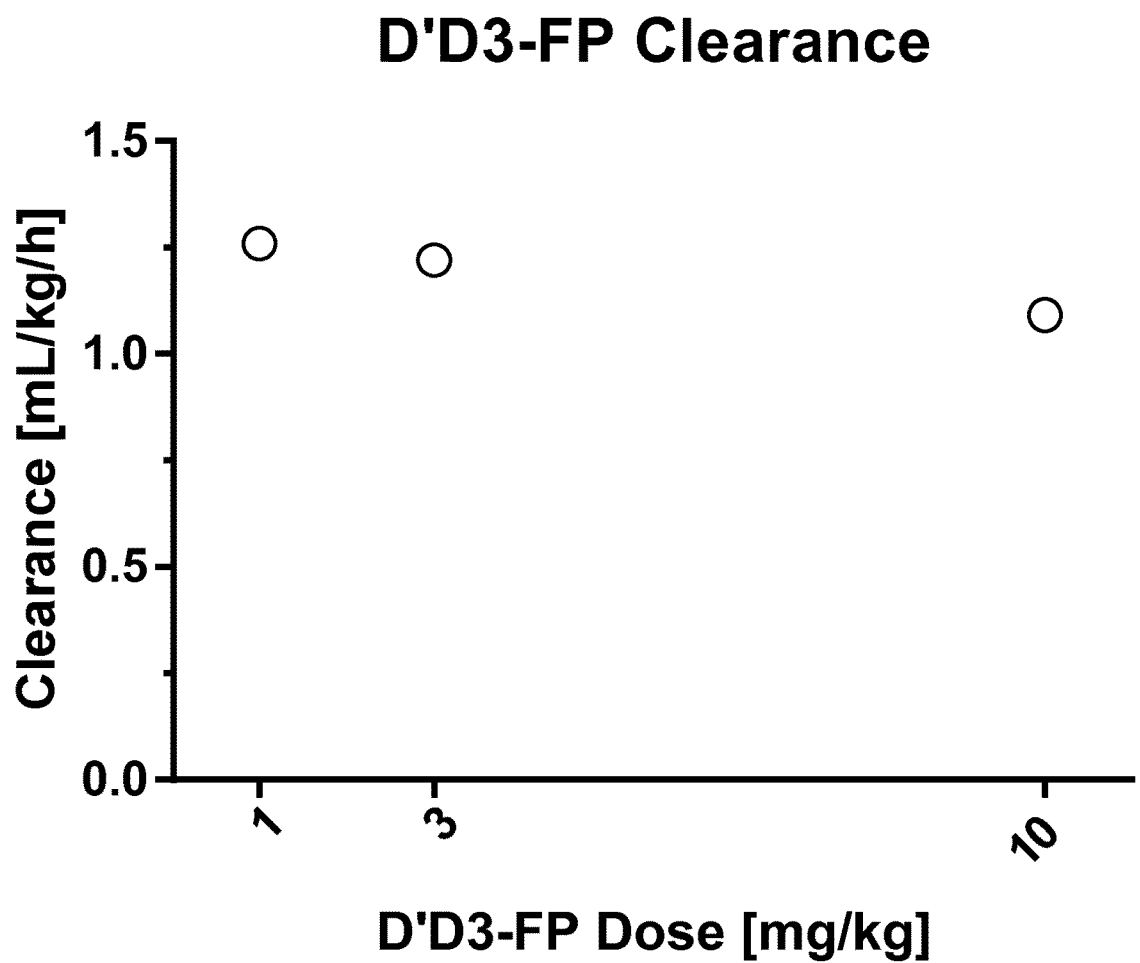

FIG. 3: Mean residence time, terminal half-life and clearance (mean) of D'D3-FP quantified by determining the albumin moiety in rats (Example 2).

Abbreviation: rVIII-SC: rVIII-SingleChain

Figure 4A:
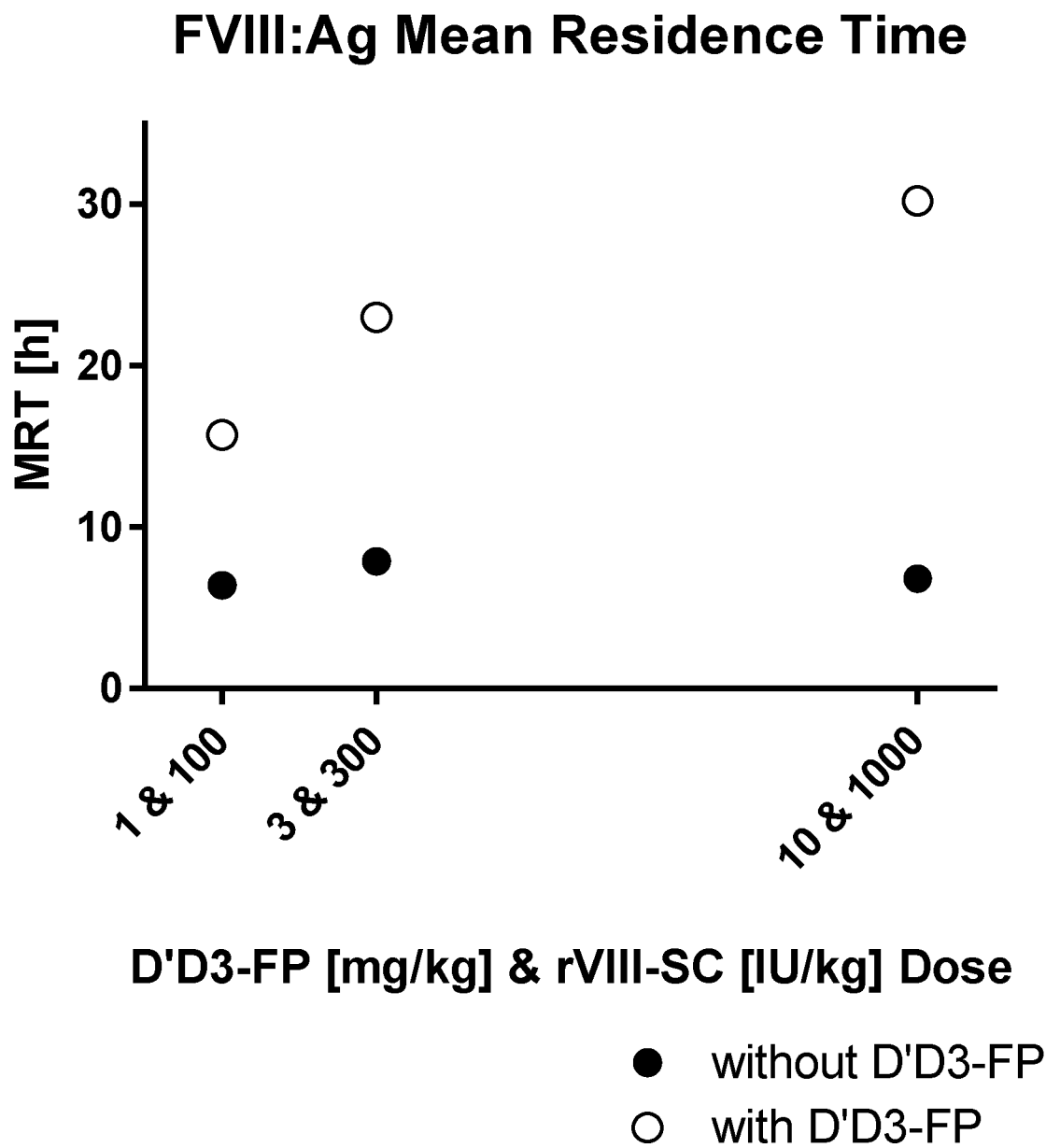
Figure 4B:
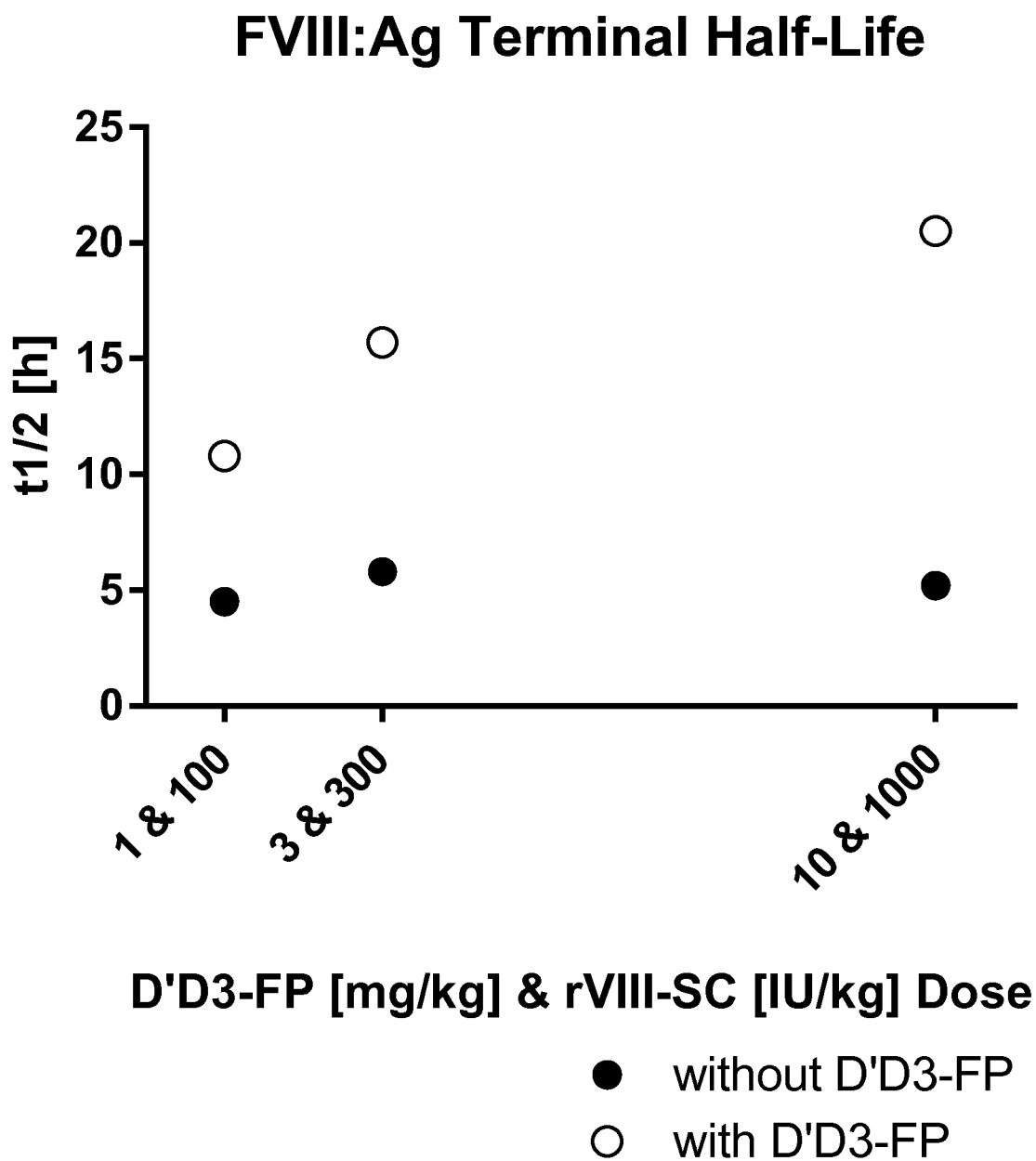
Figure 4C:
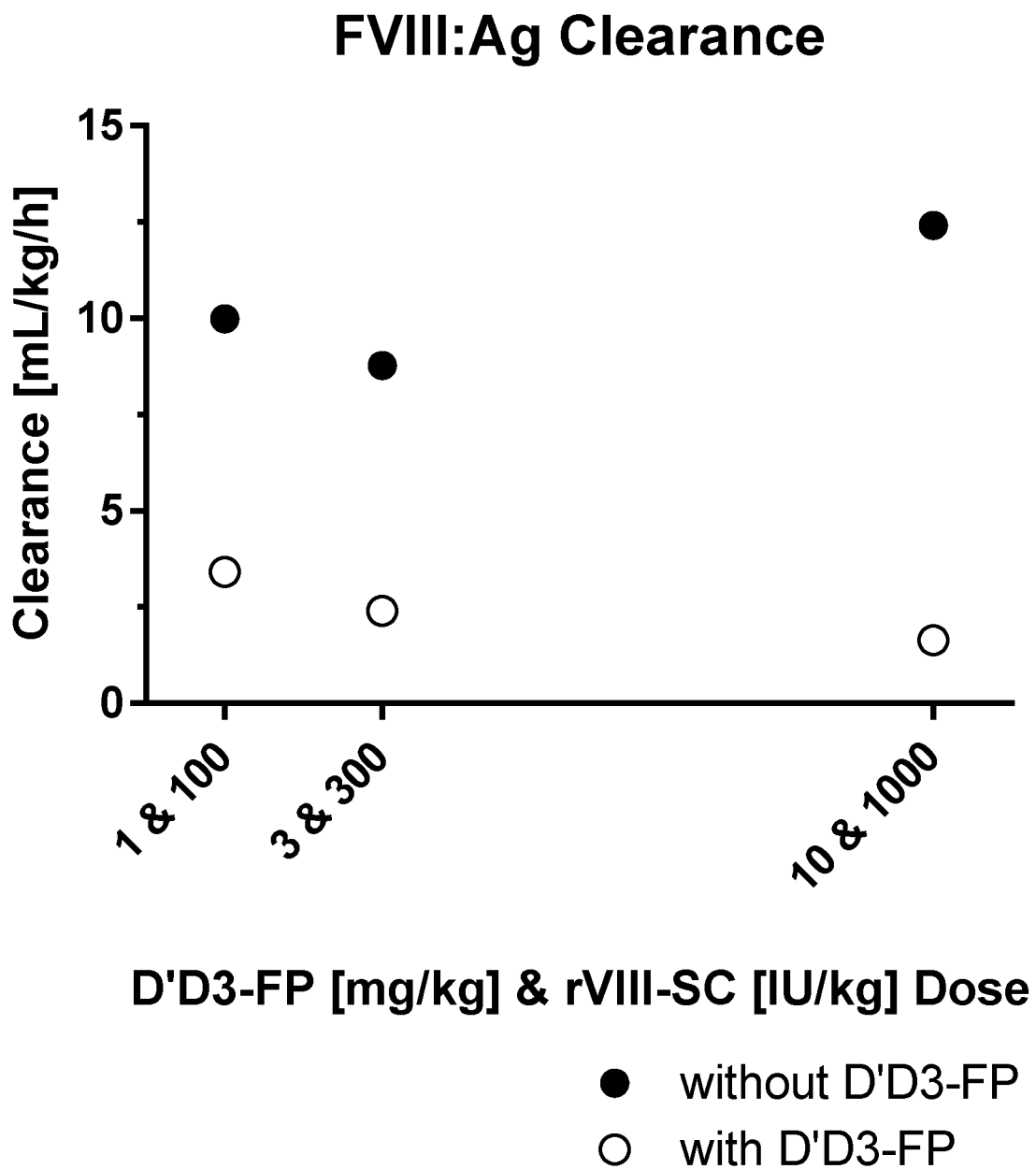

FIG. 4: Mean residence time, terminal half-life and clearance (mean) of rVIII-SingleChain quantified by determining FVIII antigen in rat (Example 2).

Abbreviation: rVIII-SC: rVIII-SingleChain

Figure 5A:
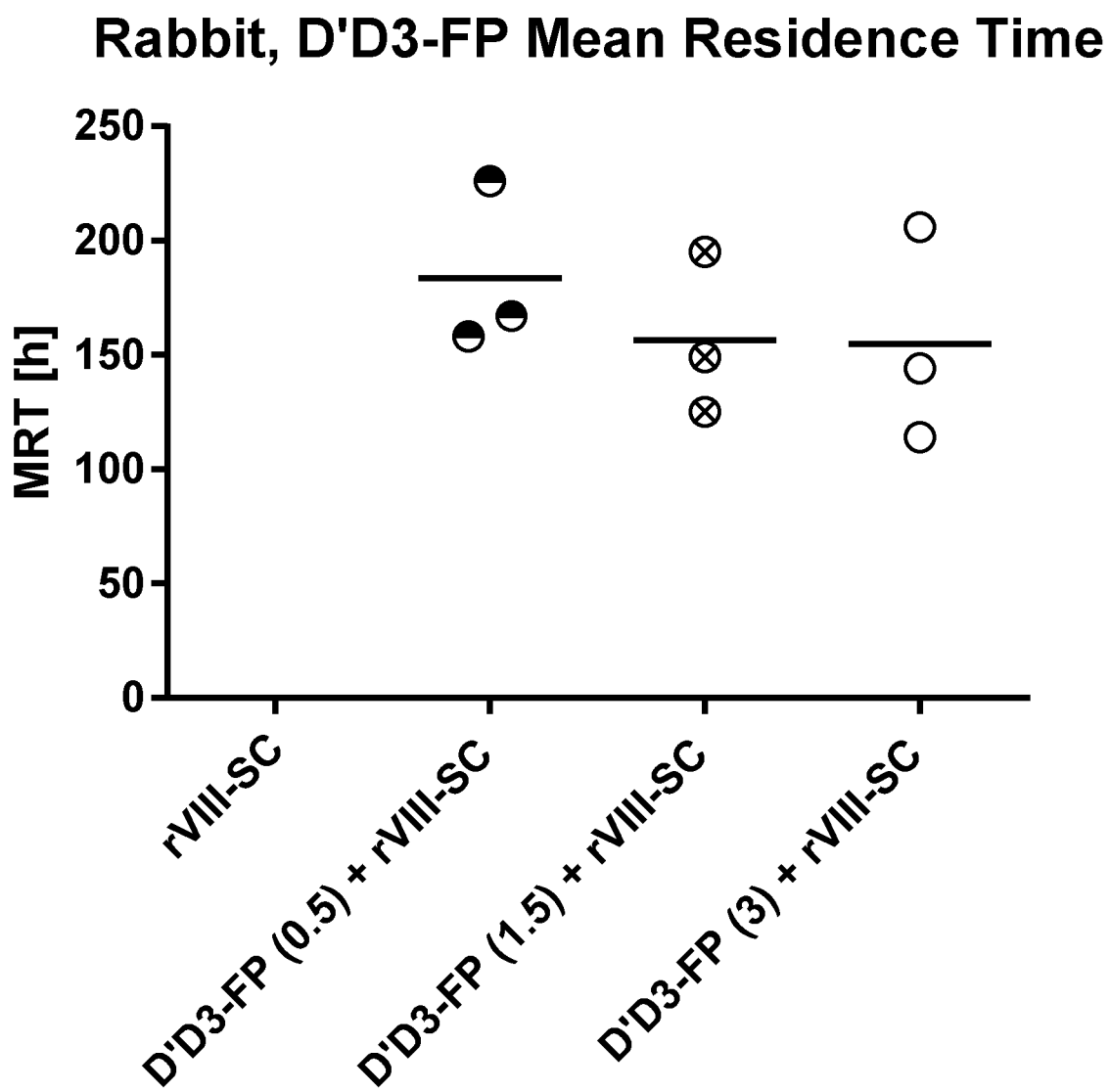
Figure 5B:
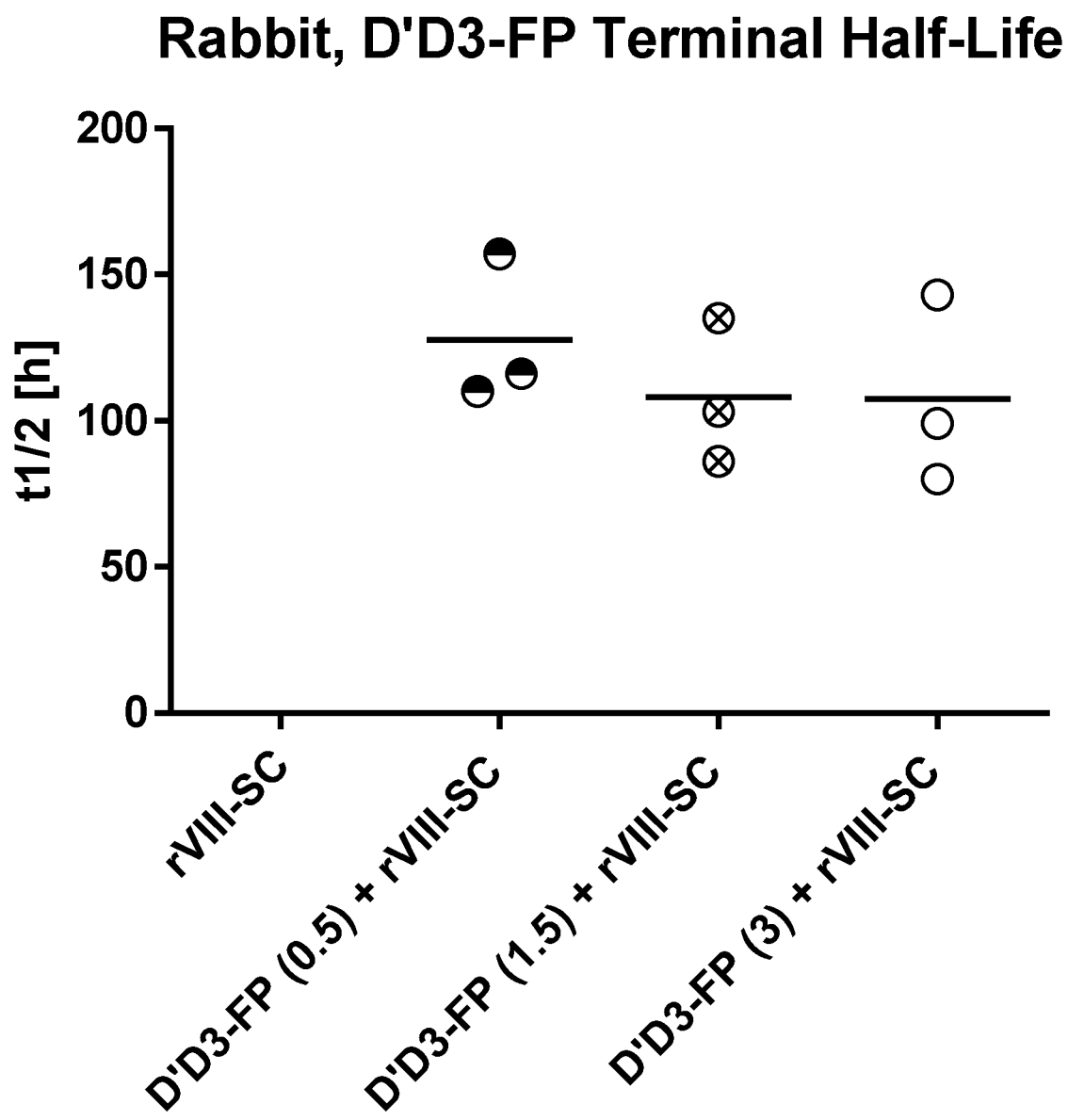
Figure 5C:
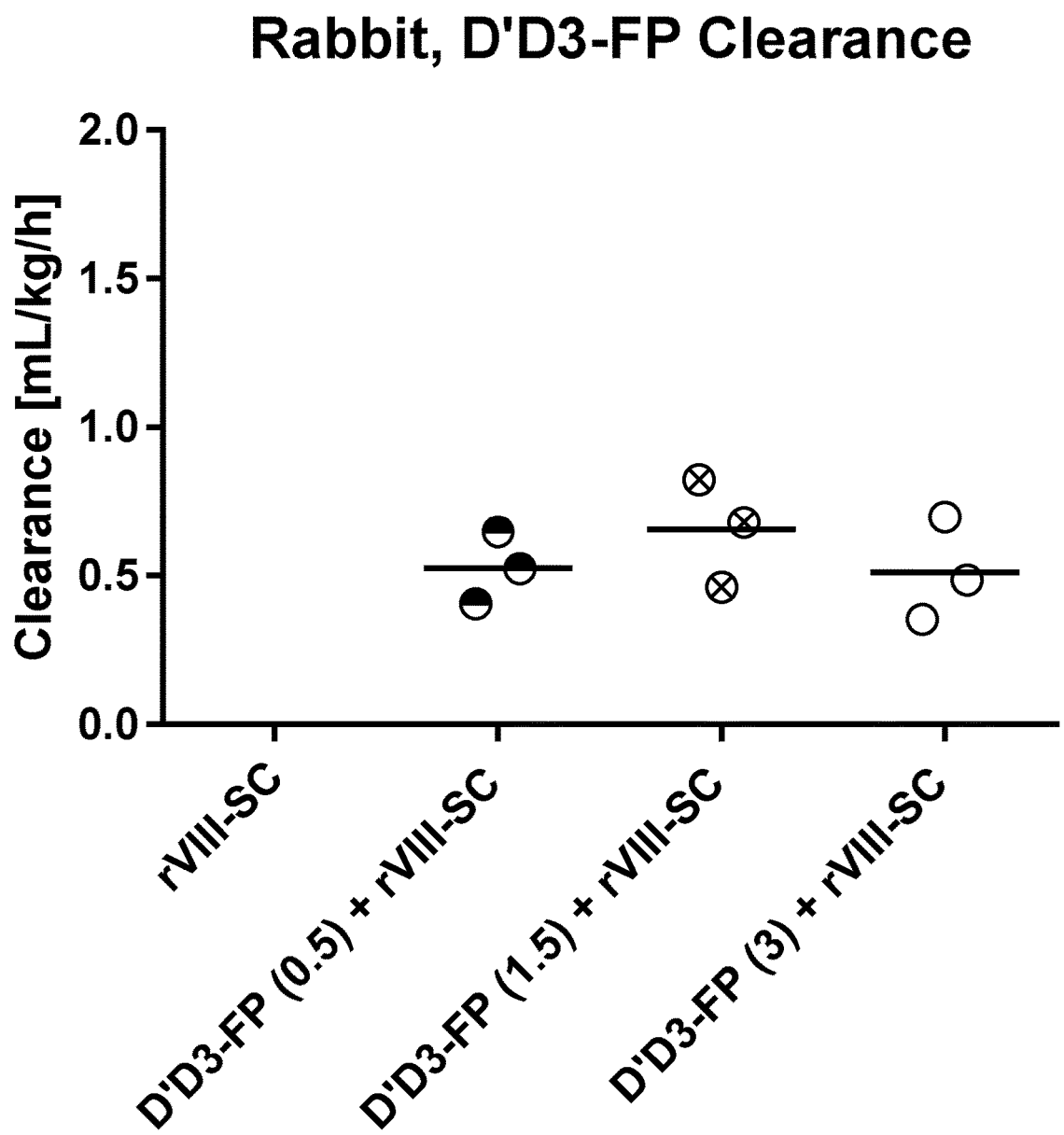

FIG. 5: Mean residence time, terminal half-life and clearance (individual animal data and mean) of D'D3-FP quantified by determining the albumin moiety in rabbits (Example 3).

Abbreviation: rVIII-SC: rVIII-SingleChain

Figure 6A:
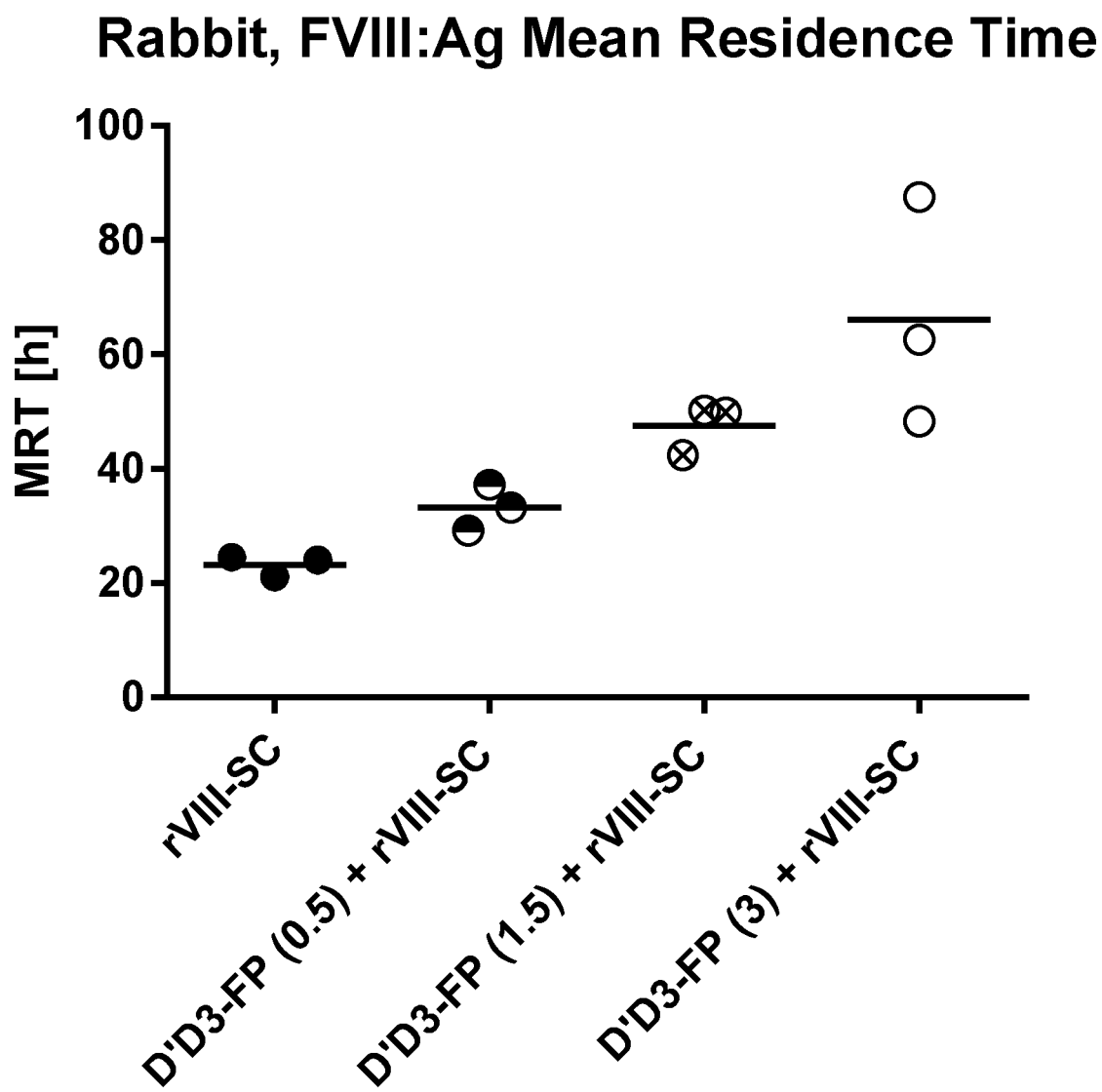
Figure 6B:
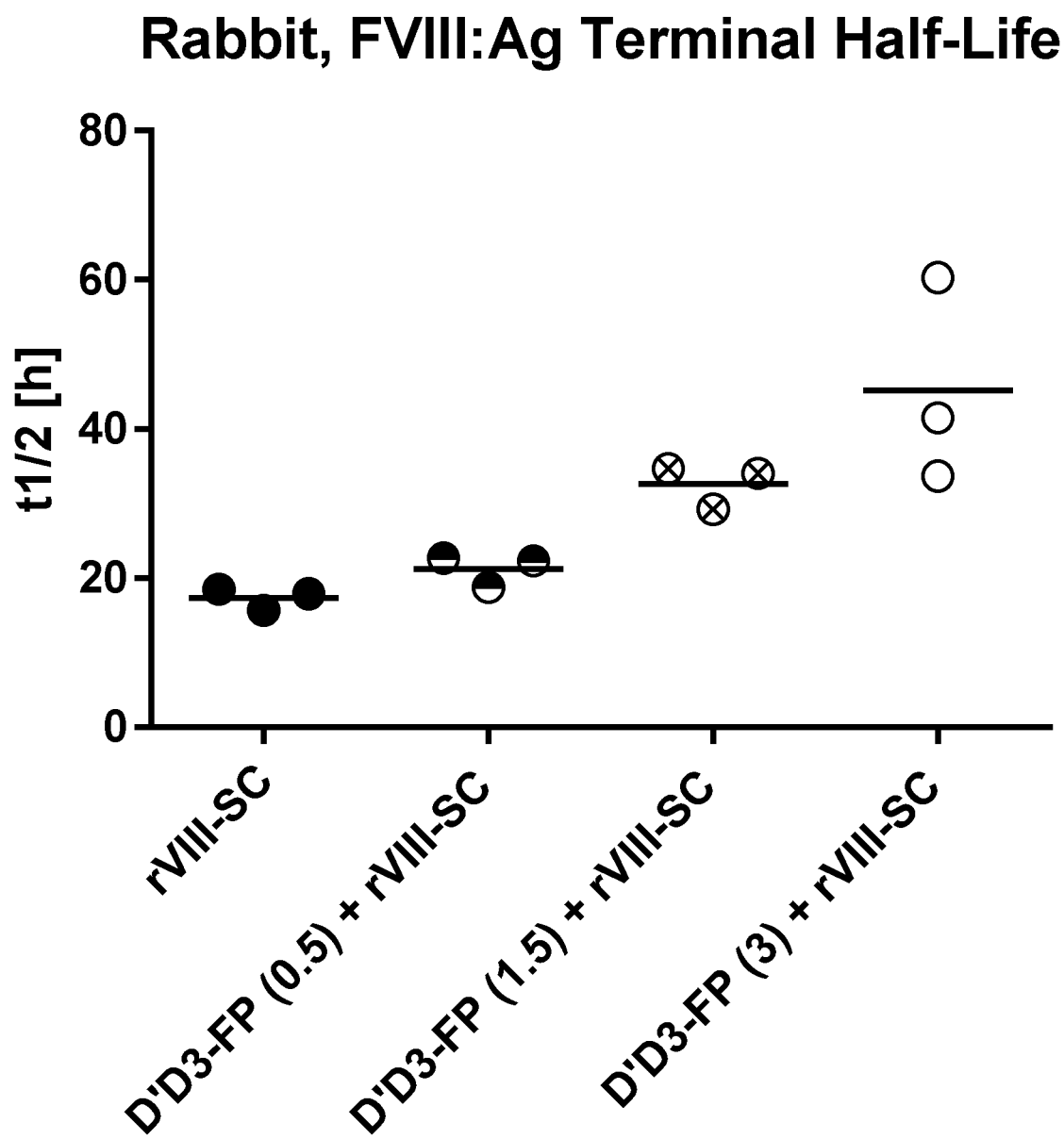
Figure 6C:
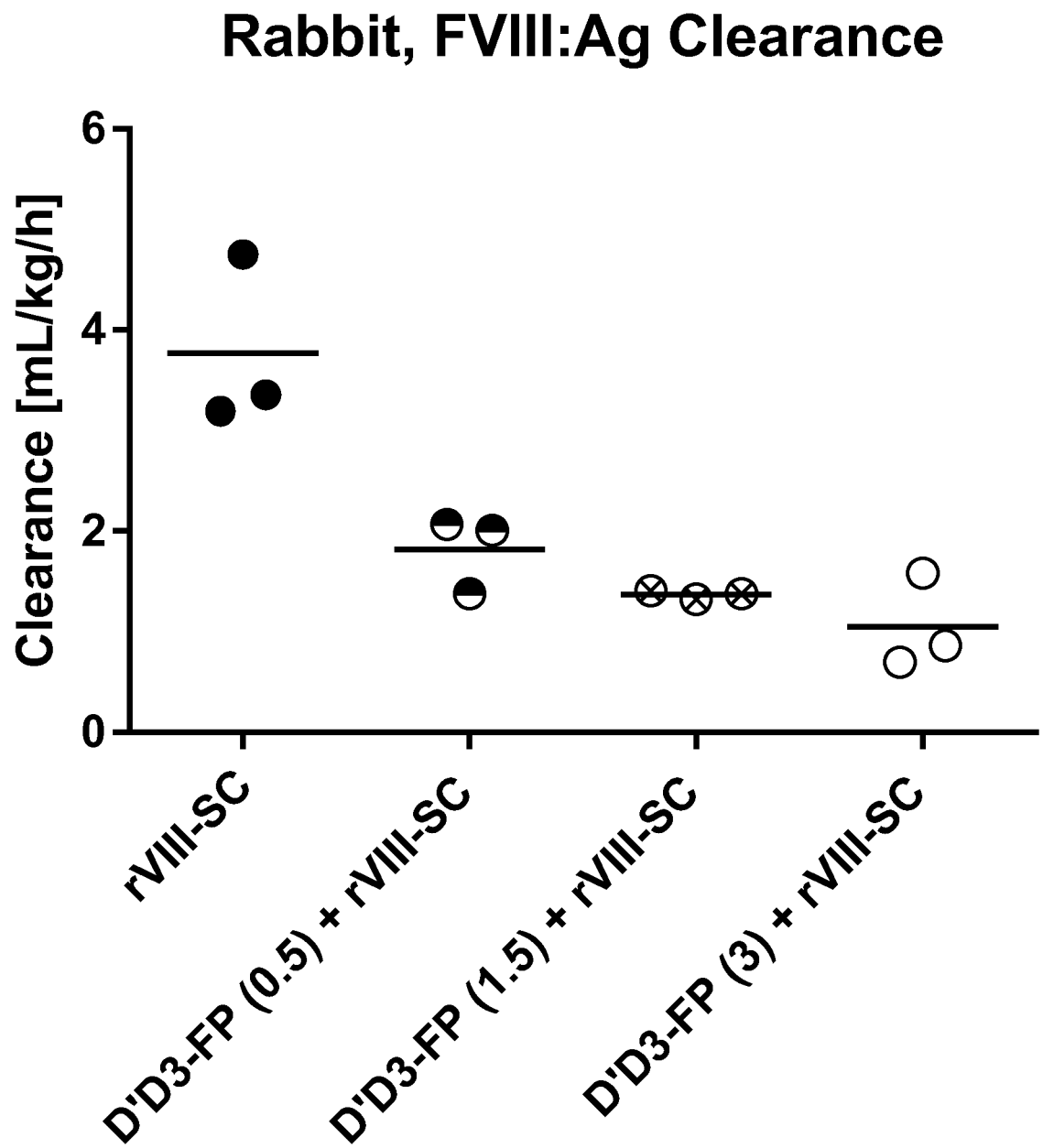

FIG. 6: Mean residence time, terminal half-life and clearance (individual animal data and mean) of rVIII-SingleChain quantified by determining FVIII antigen in rabbits (Example 3).

Abbreviation: rVIII-SC: rVIII-SingleChain

Figure 7A:
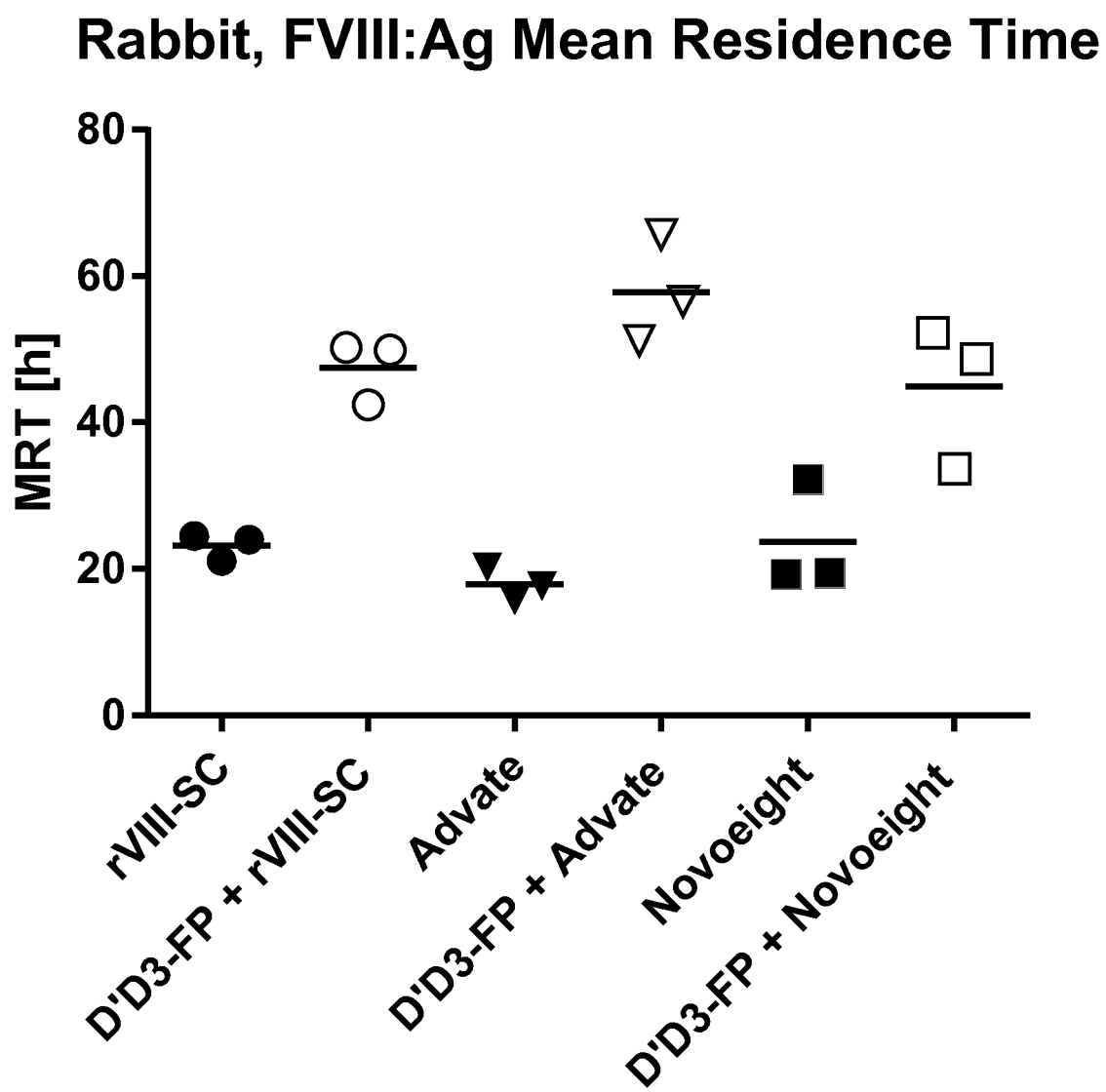
Figure 7B:
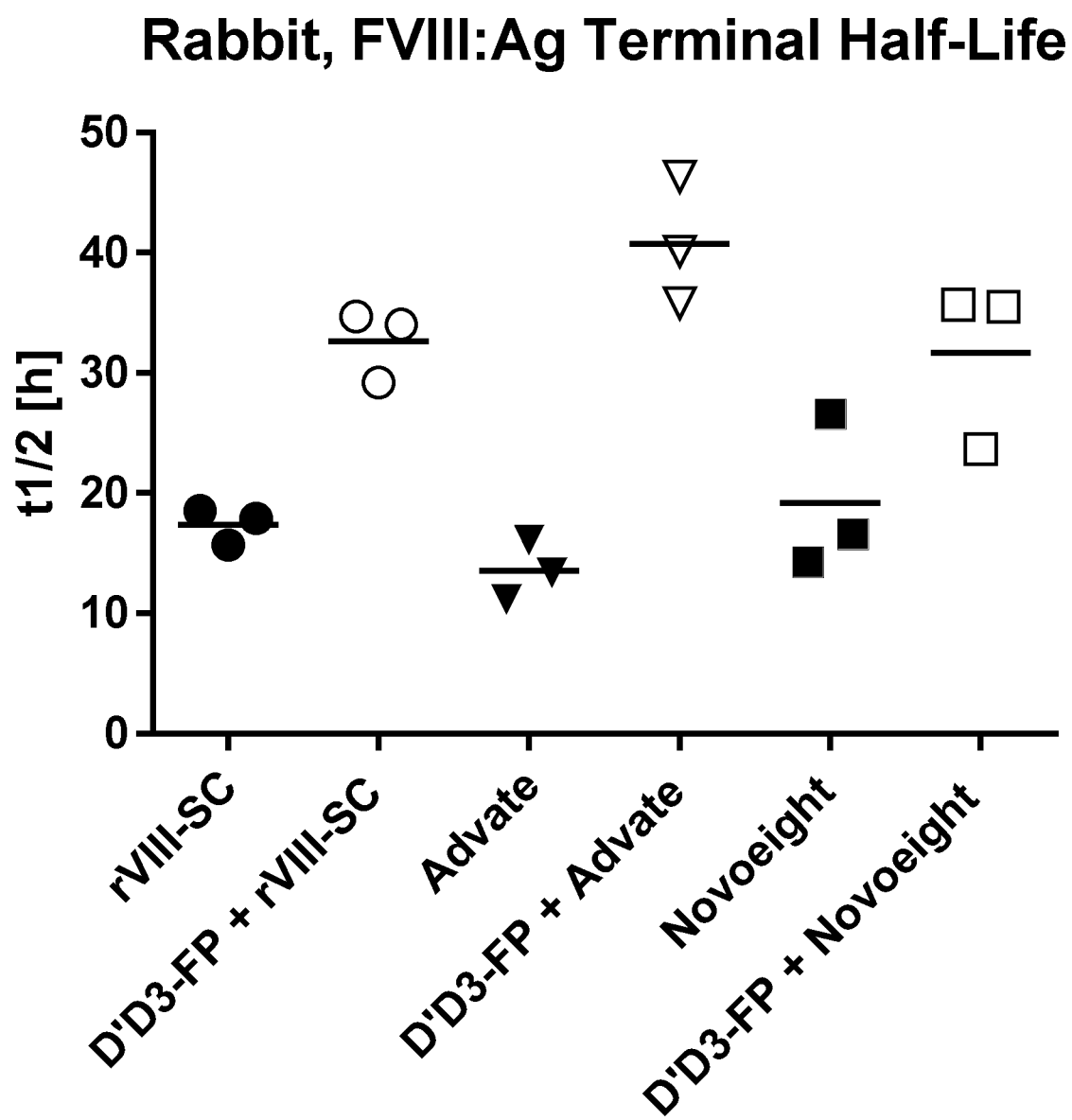
Figure 7C:
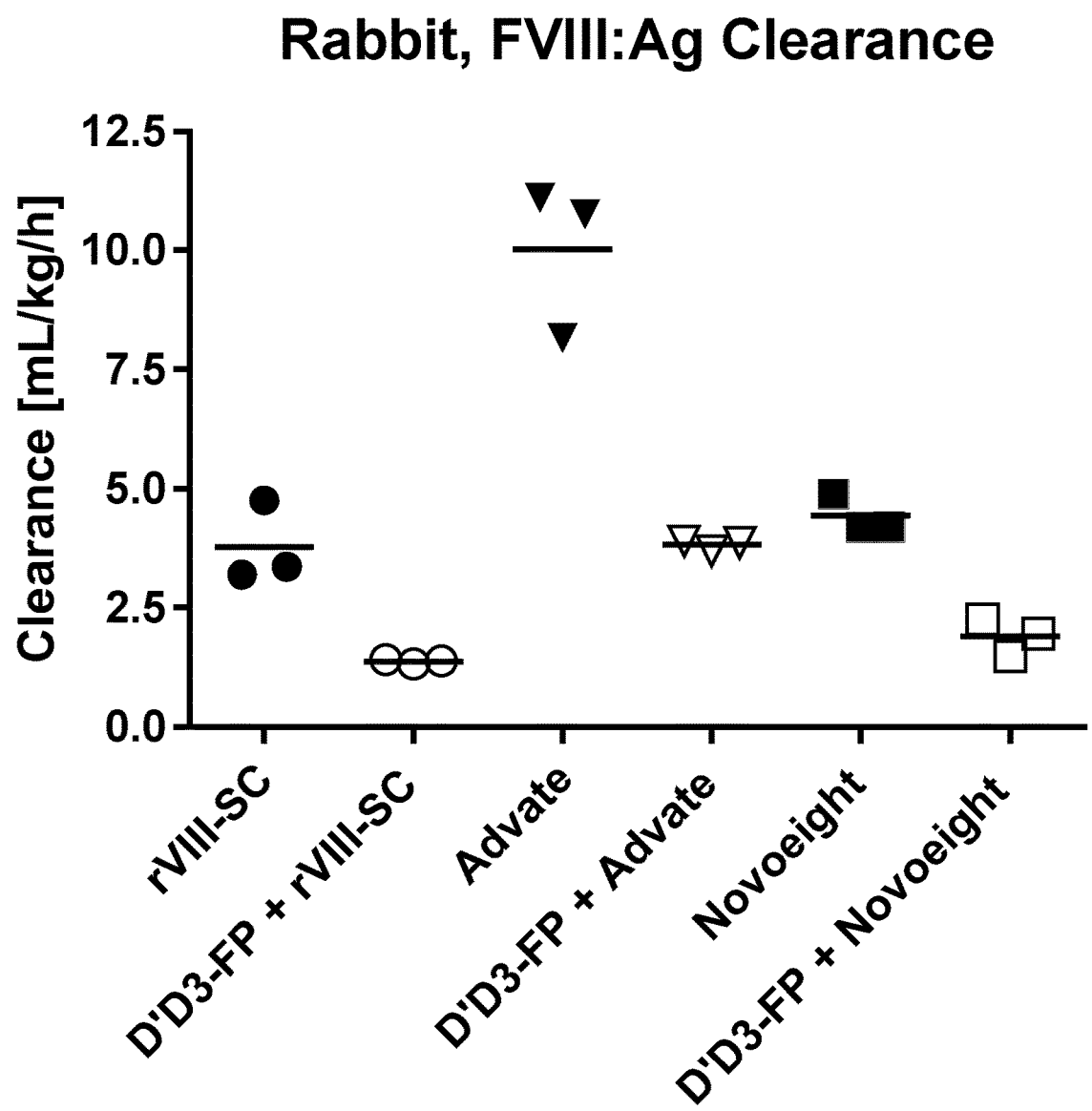

FIG. 7: Mean residence time, terminal half-life and clearance (individual animal data and mean) of different recombinant FVIII products quantified by determining FVIII antigen in rabbits (Example 4).

Abbreviation: rVIII-SC: rVIII-SingleChain

Figure 8A:
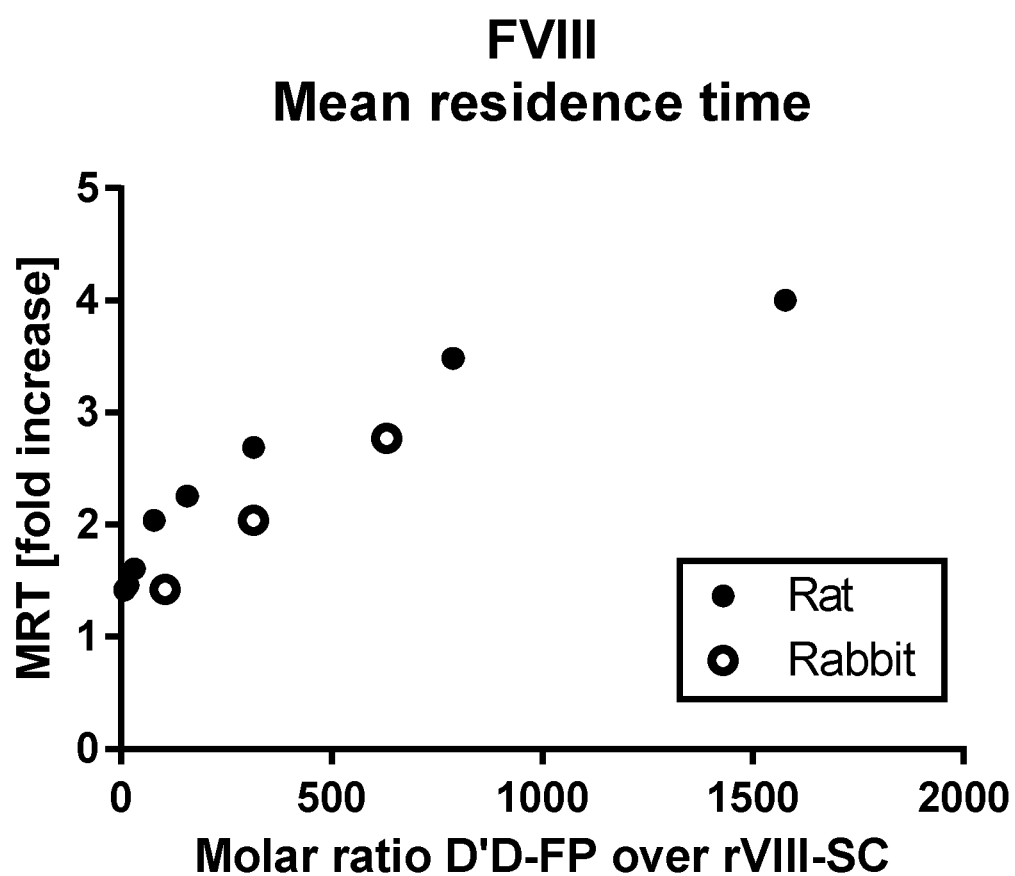
Figure 8B:
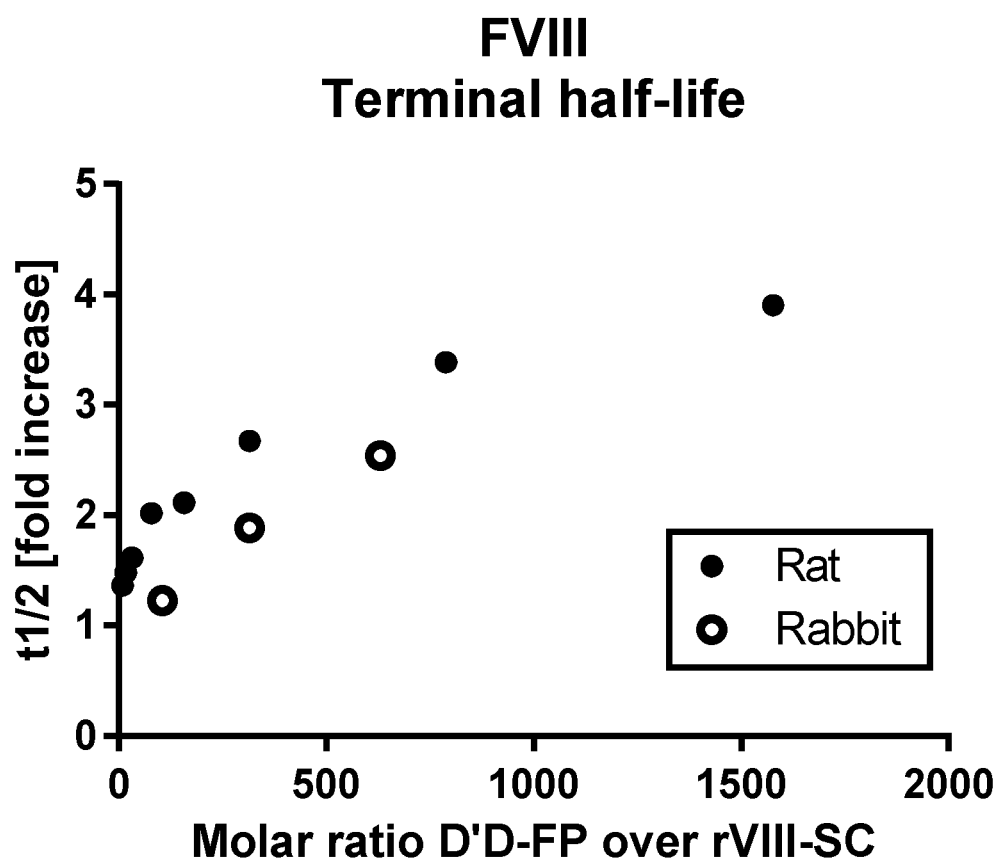
Figure 8C:
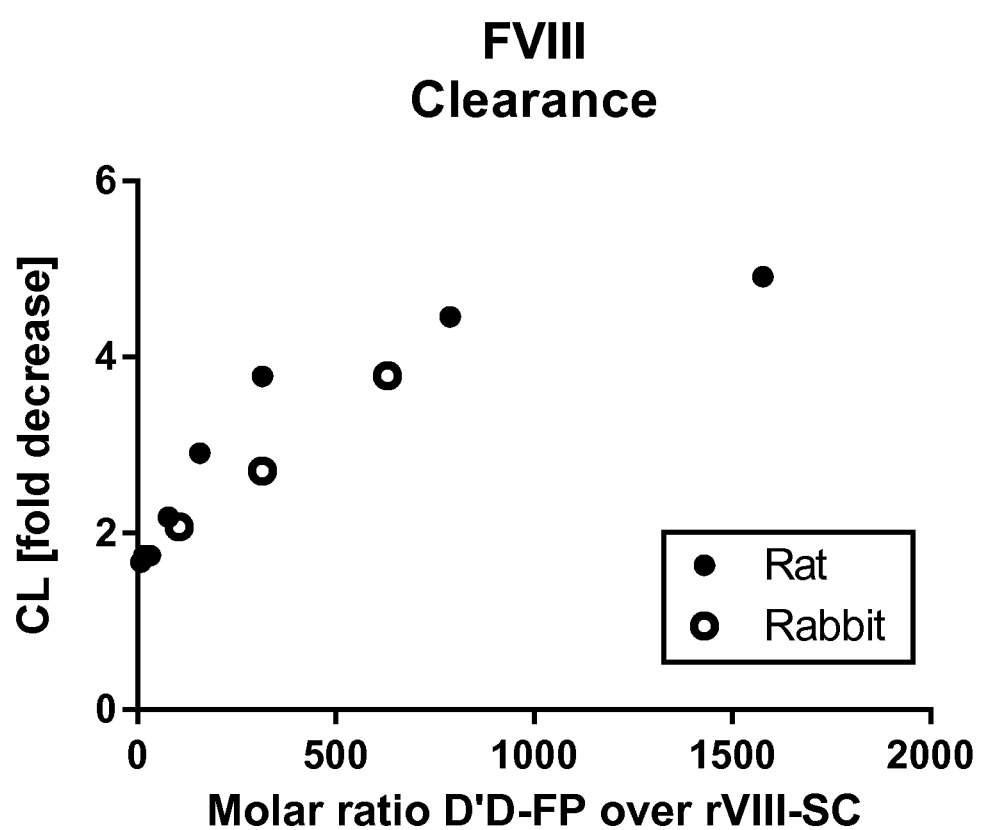

FIG. 8: Changes of mean residence time, terminal half-life and clearance of FVIII in dependence of the molar ratio of D'D3-FP over rVIII-SingleChain (rVIII-SC given alone is defined as 1-fold change) in rats and rabbits.

Abbreviation: rVIII-SC: rVIII-SingleChain

Figure 9A:
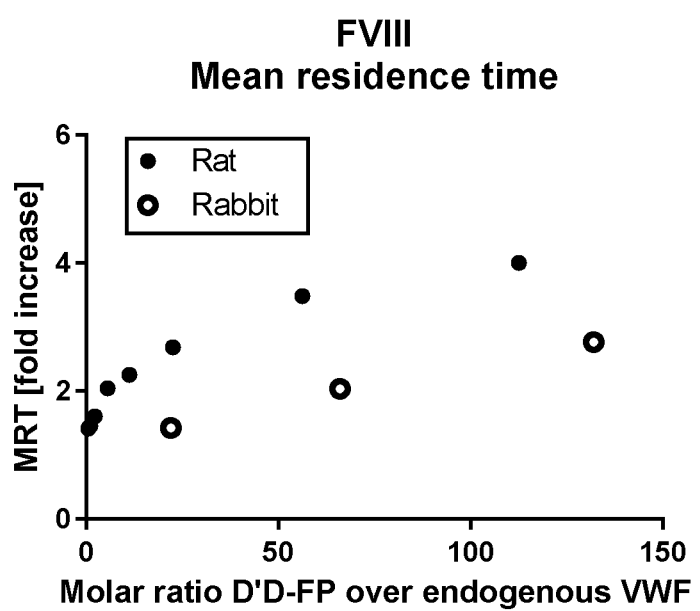
Figure 9B:
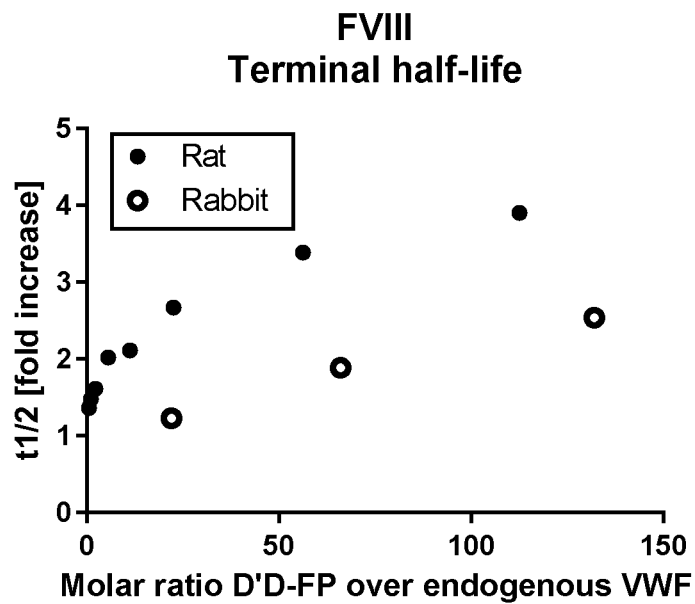
Figure 9C:
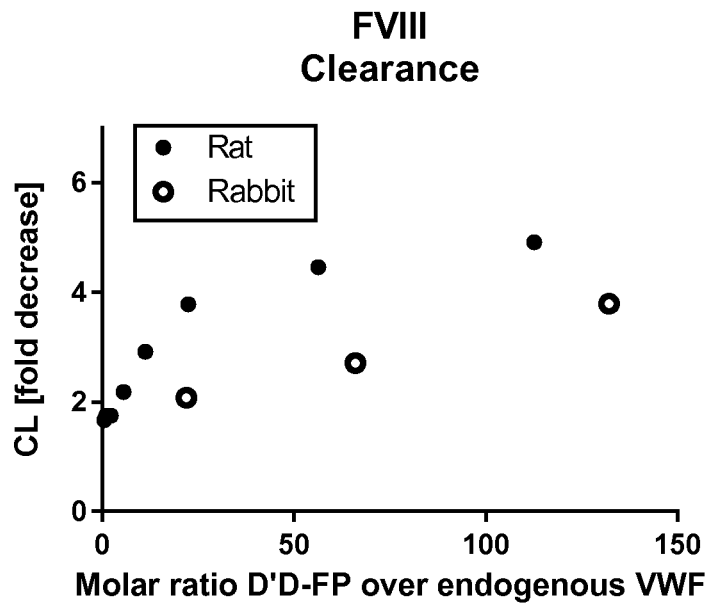

FIG. 9: Changes of mean residence time, terminal half-life and clearance of FVIII in dependence of the molar ratio of D'D3-FP over endogenous VWF (rVIII-SC given alone is defined as 1-fold change) in rats and rabbits.

DETAILED DESCRIPTION

In a first aspect, the present invention relates to a polypeptide comprising a truncated von Willebrand Factor (VWF) for use in the treatment of a blood coagulation disorder, said treatment comprising administering to a subject having endogenous VWF the polypeptide and a Factor VIII (FVIII), wherein the polypeptide is capable of binding to said FVIII, and wherein the molar ratio of the polypeptide to be administered to the FVIII to be administered is greater than 50. In preferred embodiments the polypeptide comprises a half-life extending moiety.

In a second aspect, the present invention pertains to a polypeptide comprising a polypeptide comprising a truncated von Willebrand Factor (VWF), for use in the treatment of a blood coagulation disorder, said treatment comprising administering to a subject having endogenous VWF the polypeptide and a Factor VIII (FVIII), wherein the polypeptide is capable of binding to said FVIII, and wherein the molar ratio of the polypeptide administered to the endogenous VWF is greater than 0.5. In preferred embodiments the polypeptide comprises a half-life extending moiety.

The polypeptide comprising a truncated von Willebrand Factor (VWF) will be referred to herein as "polypeptide of the invention". The polypeptide of the invention preferably comprises a half-life extending moiety.

Ratios

As described in more detail below, the polypeptide of the invention may be a monomer, a dimer, or a mixture thereof. Any molar ratios according to the invention refer to a ratio of the molar concentration of the monomeric subunit of the polypeptide of the invention, whether actually present as monomer or dimer. Ratios are formed either over the molar concentration of the co-administered FVIII or over the molar concentration of the endogenous VWF monomeric subunits. Any ratios of polypeptide of the invention over FVIII in this application refer to the amount of polypeptide of the invention to be administered (in mole) divided by the amount of FVIII to be administered (in mole), unless indicated otherwise. The endogenous VWF is the VWF which is naturally present in the plasma of the animal or human being to be dosed with the polypeptide of the invention and with the co-administered FVIII. It usually consists of a range of different oligomers of approximately 2 to 40 monomeric subunits of VWF. Unless indicated otherwise, any ratios of polypeptide of the invention over endogenous VWF in this application refer to the molar plasma concentration of polypeptide of the invention immediately after administration of the polypeptide of the invention, divided by the molar plasma concentration of endogeneous VWF monomeric subunits (endogeneous VWF) The molar plasma concentration of the polypeptide of the invention immediately after administration of the polypeptide of the invention is calculated assuming a dilution of the polypeptide of the invention administered directly after administration in a plasma volume of 40 mL/kg. The amount of the polypeptide of the invention immediately after administration when administered intravenously is assumed for the purposes of the invention to be identical to the amount administered.

According to one aspect of the invention the molar ratio of the polypeptide of the invention to the endogenous VWF is greater than 0.5. The concentration of endogenous VWF in the plasma of the subject to be treated can be determined by an ELISA or and activity assay, e.g. as described in the Examples. Typically, the concentration measured will be given in U/mL. This value can be converted into a molarity as described in the following.

Normal human plasma (NHP) contains VWF in a concentration of 1 U/mL or 100% by definition. This corresponds to a protein concentration of approximately 10 µg/mL (Haberichter S. L. and Montgomery R. R., Structure and function of von Willebrand factor; in: Hemostasis and Thrombosis, eds. Marder, Aird, Bennett, Schulman and White, Lippincott Williams & Wilkins 2013, pp 197-207). Based on this VWF concentration in NHP and a molecular weight of the mature VWF monomer of approximately 267,500 Da including 18-19% of glycosylation a molar plasma concentration of the VWF monomer unit of approximately $37 \times 10^{-9}$ Mol/L can be calculated for NHP.

For calculation of the molar concentrations of rat or rabbit VWF subunits in normal rat or rabbit plasma, respectively, a molecular weight of the monomeric subunit comparable to human VWF was used (267,500 Da) together with an assumed comparable specific activity (100 U/mg) and the measured endogenous VWF activities in rat or rabbit plasma (refer also to examples).

The concentration of VWF in the human population varies from about 60% to about 200% of VWF concentration in NHP. In certain embodiments of the invention the concentration of endogenous VWF is defined as the concentration in NHP. In other embodiments the concentration of endogenous VWF is determined in the subject to be treated, and the dose of the polypeptide is based on this individual value.

The molar ratio of the polypeptide of the invention administered to the endogenous VWF is preferably at least 2, or at least 3, or at least 4, or at least 5, or at least 6, or at least 7, or at least 8, or at least 9, or at least 10, more preferably at least 15, or at least 20, or at least 25, or at least 30, most preferably at least 40, or at least 50, or at least 75.

The molar ratio of the polypeptide of the invention to be administered to the endogenous VWF may range from 0.5 to 1,000, or from 1 to 500, or from 2 to 400, or from 3 to 300, or from 4 to 250, or from 5 to 200, or from 6 to 150, or from 7 to 140, or from 8 to 130, or from 9 to 120, or from 10 to 110. Preferably, the molar ratio of the polypeptide of the invention administered to endogenous VWF ranges from 3 to 100, or from 4 to 90, or from 5 to 80, or from 6 to 75, or from 10 to 60.

The molar ratio of the polypeptide of the invention to be administered to FVIII to be administered is preferably at least 2, or at least 5, or at least 10, or at least 20, or at least 30, or at least 40, or at least 50, more preferably the ratio is greater than 50, or at least 75, at least 100, or greater than 100, or at least 200, most preferably at least 300, or at least 400, or at least 500, or at least 600, or at least 700, or at least 800, or at least 900, or at least 1,000, or at least 1,100, or at least 1,200, or at least 1,300, or at least 1,400, or at least 1,500, or at least 1,600, or at least 1,700, or at least 1,800, or at least 1,900, or at least 2,000, or at least 2,500, or at least 3,000 or at least 5,000, or at least 8,000 or up to 10,000.

The molar ratio of the polypeptide of the invention to be administered to FVIII to be administered may range from 2 to 10,000, or from 5 to 5,000, or from 10 to 4,000, or from 20 to 3,000, or from 30 to 2,000, or from 40 to 1,000. Preferably, the molar ratio of the polypeptide of the invention to be administered to FVIII to be administered ranges from 60 to 2,500, or from 110 to 2,000, or from 150 to 1,500, or from 200 to 1,000.

Table 1 summarizes various embodiments of the treatment in accordance with this invention. In a given embodiment, both requirements of column 2 and 3, respectively, must be fulfilled.

TABLE 1

| Embodiment # | Molar ratio polypeptide of the invention:endogenous VWF | Molar ratio polypeptide of the invention:FVIII administered |
|---|---|---|
| 1 | at least 1 | at least 2 |
| 2 | at least 1 | at least 5 |
| 3 | at least 1 | at least 10 |
| 4 | at least 1 | at least 40 |
| 5 | at least 1 | at least 50 |
| 6 | at least 1 | at least 80 |
| 7 | at least 1 | at least 100 |
| 6 | at least 1 | at least 150 |
| 7 | at least 1 | at least 250 |
| 8 | at least 1 | at least 400 |
| 9 | at least 1 | at least 800 |
| 10 | at least 1 | at least 1,000 |
| 11 | at least 3 | at least 2 |
| 12 | at least 3 | at least 5 |
| 13 | at least 3 | at least 10 |
| 14 | at least 3 | at least 40 |
| 15 | at least 3 | at least 50 |
| 16 | at least 3 | at least 80 |
| 17 | at least 3 | at least 100 |
| 18 | at least 3 | at least 150 |
| 19 | at least 3 | at least 250 |
| 20 | at least 3 | at least 400 |
| 21 | at least 3 | at least 800 |
| 22 | at least 3 | at least 1,000 |
| 23 | at least 5 | at least 2 |
| 24 | at least 5 | at least 5 |
| 25 | at least 5 | at least 10 |
| 26 | at least 5 | at least 40 |
| 27 | at least 5 | at least 50 |
| 28 | at least 5 | at least 80 |
| 29 | at least 5 | at least 100 |
| 30 | at least 5 | at least 150 |
| 31 | at least 5 | at least 250 |
| 32 | at least 5 | at least 400 |
| 33 | at least 5 | at least 800 |
| 34 | at least 5 | at least 1,000 |
| 35 | at least 10 | at least 2 |
| 36 | at least 10 | at least 5 |
| 37 | at least 10 | at least 10 |
| 38 | at least 10 | at least 40 |
| 39 | at least 10 | at least 50 |
| 40 | at least 10 | at least 80 |
| 41 | at least 10 | at least 100 |
| 42 | at least 10 | at least 150 |
| 43 | at least 10 | at least 250 |
| 44 | at least 10 | at least 400 |
| 45 | at least 10 | at least 800 |
| 46 | at least 10 | at least 1,000 |
| 47 | at least 20 | at least 2 |
| 48 | at least 20 | at least 5 |
| 49 | at least 20 | at least 10 |
| 50 | at least 20 | at least 40 |
| 51 | at least 20 | at least 50 |
| 52 | at least 20 | at least 80 |
| 53 | at least 20 | at least 100 |
| 54 | at least 20 | at least 150 |
| 55 | at least 20 | at least 250 |
| 56 | at least 20 | at least 400 |
| 57 | at least 20 | at least 800 |
| 58 | at least 20 | at least 1,000 |
| 59 | at least 50 | at least 2 |
| 60 | at least 50 | at least 5 |
| 61 | at least 50 | at least 10 |
| 62 | at least 50 | at least 40 |
| 63 | at least 50 | at least 50 |
| 64 | at least 50 | at least 80 |
| 65 | at least 50 | at least 100 |
| 66 | at least 50 | at least 150 |
| 67 | at least 50 | at least 250 |
| 68 | at least 50 | at least 400 |
| 69 | at least 50 | at least 800 |
| 70 | at least 50 | at least 1,000 |
| 71 | at least 50 | at least 2,000 |
| 72 | at least 50 | at least 4,000 |

Embodiments 1 to 72 shown in Table 1 can be combined with any other embodiment and aspect of the invention described herein. Further details of the treatment in accordance with the invention are described further below.

The Truncated VWF

The term "von Willebrand Factor" (VWF) as used herein includes naturally occurring (native) VWF, but also variants thereof retaining at least the FVIII binding activity of naturally occurring VWF, e.g. sequence variants where one or more residues have been inserted, deleted or substituted. The FVIII binding activity is determined by a FVIII-VWF binding assay as described in Example 6.

The preferred VWF in accordance with this invention is human VWF represented by the amino acid sequence shown in SEQ ID NO:4. The cDNA encoding SEQ ID NO:4 is shown in SEQ ID NO:3.

The gene encoding human native VWF is transcribed into a 9 kb mRNA which is translated into a pre-propolypeptide of 2813 amino acids with an estimated molecular weight of 310,000 Da. The pre-propolypeptide contains an N-terminal 22 amino acids signal peptide, followed by a 741 amino acid pro-polypeptide (amino acids 23-763 of SEQ ID NO:4) and the mature subunit (amino acids 764-2813 of SEQ ID NO:4). Cleavage of the 741 amino acids propolypeptide from the N-terminus results in mature VWF consisting of 2050 amino acids. The amino acid sequence of the human native VWF pre-propolypeptide is shown in SEQ ID NO:4. Unless indicated otherwise, the amino acid numbering of VWF residues in this application refers to SEQ ID NO:4, even if the VWF molecule does not comprise all residues of SEQ ID NO:4.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application:

D1-D2-D'-D3-A1-A2-A3-D4-C1-C2-C3-C4-C5-C6-CK

With reference to SEQ ID NO:4, the D' domain consists of amino acids 764-865; and the D3 domain consists of amino acids 866-1242.

The feature "truncated" means that the polypeptide does not comprise the entire amino acid sequence of mature VWF (amino acids 764-2813 of SEQ ID NO:4). Typically, the truncated VWF does not comprise all amino acids 764-2813 of SEQ ID NO:4 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. In another embodiment, the truncated VWF is capable of binding to the single-chain Factor VIII consisting of the amino acid sequence SEQ ID NO:5. Binding of the truncated VWF to Factor VIII can be determined by a FVIII-VWF binding assay as described in Example 6.

The truncated VWF of the present invention preferably comprises or consists of an amino acid sequence having a sequence identity of at least 90% to amino acids 776 to 805 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 776 to 805 of SEQ ID NO:4 and is capable of binding to FVIII. Most preferably, the truncated VWF comprises or consists of amino acids 776 to 805 of SEQ ID NO:4. Unless indicated otherwise herein, sequence identities are determined over the entire length of the reference sequence (e.g. amino acids 776 to 805 of SEQ ID NO:4).

The truncated VWF of the present invention preferably comprises or consists of an amino acid sequence having a sequence identity of at least 90% to amino acids 766 to 864 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 766 to 864 of SEQ ID NO:4 and is capable of binding to FVIII. Most preferably, the truncated VWF comprises or consists of amino acids 766 to 864 of SEQ ID NO:4.

In another preferred embodiment, the truncated VWF consists of (a) an amino acid sequence having a sequence identity of at least 90% to amino acids 764 to 1242 of SEQ ID NO:4, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:4, or (b) a fragment thereof, provided that the truncated VWF is still capable of binding to FVIII. Most preferably, the truncated VWF consists of (a) amino acids 764 to 1242 of SEQ ID NO:4, or (b) a fragment thereof, provided that the truncated VWF is still capable of binding to FVIII.

As described in more detail below, the polypeptide may be prepared by a method which uses cells comprising a nucleic acid encoding the polypeptide comprising the truncated VWF. The nucleic acid is introduced into suitable host cells by techniques that are known per se.

In a preferred embodiment, the nucleic acid in the host cell encodes (a) an amino acid sequence having a sequence identity of at least 90% to amino acids 1 to 1242 of SEQ ID NO:4, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:4, or (b) a fragment thereof, provided that the truncated VWF is still capable of binding to FVIII. Most preferably, the nucleic acid encodes (a) amino acids 1 to 1242 of SEQ ID NO:4, or (b) a fragment thereof, provided that the truncated VWF is still capable of binding to FVIII. Especially if the polypeptide in accordance with this invention is a dimer, the nucleic acid will comprise a sequence encoding amino acids 1 to 763 of VWF (e.g. SEQ ID NO:4), even if the truncated VWF in the polypeptide does not comprise amino acids 1 to 763 of VWF (e.g. SEQ ID NO:4).

In other embodiments the truncated VWF comprises or consists of one of the following amino acid sequences, each referring to SEQ ID NO:4:

776-805; 766-805; 764-805; 776-810; 766-810; 764-810; 776-815; 766-815; 764-815;
776-820; 766-820; 764-820; 776-825; 766-825; 764-825; 776-830; 766-830; 764-830;
776-835; 766-835; 764-835; 776-840; 766-840; 764-840; 776-845; 766-845; 764-845;
776-850; 766-850; 764-850; 776-855; 766-855; 764-855; 776-860; 766-860; 764-860;
776-864; 766-864; 764-864; 776-865; 766-865; 764-865; 776-870; 766-870; 764-870;
776-875; 766-875; 764-875; 776-880; 766-880; 764-880; 776-885; 766-885; 764-885;
776-890; 766-890; 764-890; 776-895; 766-895; 764-895; 776-900; 766-900; 764-900;
776-905; 766-905; 764-905; 776-910; 766-910; 764-910; 776-915; 766-915; 764-915;
776-920; 766-920; 764-920; 776-925; 766-925; 764-925; 776-930; 766-930; 764-930;
776-935; 766-935; 764-935; 776-940; 766-940; 764-940; 776-945; 766-945; 764-945;
776-950; 766-950; 764-950; 776-955; 766-955; 764-955; 776-960; 766-960; 764-960;
776-965; 766-965; 764-965; 776-970; 766-970; 764-970; 776-975; 766-975; 764-975;
776-980; 766-980; 764-980; 776-985; 766-985; 764-985; 776-990; 766-990; 764-990;
776-995; 766-995; 764-995; 776-1000; 766-1000; 764-1000; 776-1005; 766-1005; 764-1005;
776-1010; 766-1010; 764-1010; 776-1015; 766-1015; 764-1015; 776-1020; 766-1020; 764-1020;
776-1025; 766-1025; 764-1025; 776-1030; 766-1030; 764-1030; 776-1035; 766-1035; 764-1035;
776-1040; 766-1040; 764-1040; 776-1045; 766-1045; 764-1045; 776-1050; 766-1050; 764-1050;
776-1055; 766-1055; 764-1055; 776-1060; 766-1060; 764-1060; 776-1065; 766-1065; 764-1065;
776-1070; 766-1070; 764-1070; 776-1075; 766-1075; 764-1075; 776-1080; 766-1080; 764-1080;
776-1085; 766-1085; 764-1085; 776-1090; 766-1090; 764-1090; 776-1095; 766-1095; 764-1095;
776-1100; 766-1100; 764-1100; 776-1105; 766-1105; 764-1105; 776-1110; 766-1110; 764-1110;
776-1115; 766-1115; 764-1115; 776-1120; 766-1120; 764-1120; 776-1125; 766-1125; 764-1125;
776-1130; 766-1130; 764-1130; 776-1135; 766-1135; 764-1135; 776-1140; 766-1140; 764-1140;
776-1145; 766-1145; 764-1145; 776-1150; 766-1150; 764-1150; 776-1155; 766-1155; 764-1155;
776-1160; 766-1160; 764-1160; 776-1165; 766-1165; 764-1165; 776-1170; 766-1170; 764-1170;
776-1175; 766-1175; 764-1175; 776-1180; 766-1180; 764-1180; 776-1185; 766-1185; 764-1185;
776-1190; 766-1190; 764-1190; 776-1195; 766-1195; 764-1195; 776-1200; 766-1200; 764-1200;
776-1205; 766-1205; 764-1205; 776-1210; 766-1210; 764-1210; 776-1215; 766-1215; 764-1215;
776-1220; 766-1220; 764-1220; 776-1225; 766-1225; 764-1225; 776-1230; 766-1230; 764-1230;
776-1235; 766-1235; 764-1235; 776-1240; 766-1240; 764-1240; 776-1242; 766-1242; 764-1242;
764-1464; 764-1250; 764-1041; 764-828; 764-865; 764-1045; 764-1035; 764-1128; 764-1198;
764-1268; 764-1261; 764-1264; 764-1459; 764-1463; 764-1464; 764-1683; 764-1873; 764-1482;
764-1479; 764-1672; and 764-1874.

In certain embodiments the truncated VWF has an internal deletion relative to mature wild type VWF. For example, the A1, A2, A3, D4, C1, C2, C3, C4, C5, C6 domains or combinations thereof may be deleted, and the D' domain, the D3 domain and the CK domain is retained. In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A polypeptide of the invention is termed a "dimer" in the present invention if two monomers of polypeptide of the invention are linked covalently. Preferably the two monomeric subunits are covalently linked via at least one disulfide bridge, e.g. by one, two, three or four disulfide bridges. The cysteine residues forming the at least one disulfide bridge are preferably located within the truncated VWF portion of the polypeptide of the invention. In one embodiment, these cysteine residues are Cys-1099, Cys-1142, Cys-1222, Cys-1225, or Cys-1227 or combinations thereof.

If the polypeptide of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, or amino acids 764 to 1227 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:4 and is capable of binding to FVIII. Most preferably, the truncated VWF comprises or consists of amino acids 764 to 1099, amino acids 764 to 1142, amino acids 764 to 1222, amino acids 764 to 1225, or amino acids 764 to 1227 of SEQ ID NO:4.

The truncated VWF may be any one of the VWF fragments disclosed in WO 2013/106787 A1, WO 2014/198699 A2, WO 2011/060242 A2 or WO 2013/093760 A2, the disclosure of which is incorporated herein by reference.

The term "endogenous VWF" as used herein refers to monomeric subunits of VWF, independent of its degree of di- or oligomerization. For example in the determination of ratios according to the present invention a ratio formed by a certain number of molecules of a polypeptide of the invention divided by 1,000 molecules of decameric multimers of VWF would be the same as a ratio formed by the same number of molecules of polypeptides of the invention divided by 2,000 pentameric multimers of VWF.

Half-Life Extending Moiety

In addition to the truncated VWF, the polypeptide of the invention may in certain preferred embodiments further comprise a half-life extending moiety. The half-life-extending moiety may be a heterologous amino acid sequence fused to the truncated VWF. Alternatively, the half-life-extending moiety may be chemically conjugated to the polypeptide comprising the truncated VWF by a covalent bond different from a peptide bond.

In certain embodiments of the invention, the half-life of the polypeptide of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the polypeptide of the invention is conjugated to a HLEP such as albumin via a chemical linker. The principle of this conjugation technology has been described in an exemplary manner by Conjuchem LLC (see, e.g., U.S. Pat. No. 7,256,253).

In other embodiments, the half-life-extending moiety is a half-life enhancing protein (HLEP). Preferably, the HLEP is an albumin or a fragment thereof. The N-terminus of the albumin may be fused to the C-terminus of the truncated VWF. Alternatively, the C-terminus of the albumin may be fused to the N-terminus of the truncated VWF. One or more HLEPs may be fused to the N- or C-terminal part of VWF provided that they do not to interfere with or abolish the binding capability of the truncated VWF to FVIII.

In one embodiment the polypeptide has the following structure:

$$tVWF\text{-}L1\text{-}H, \qquad [\text{formula 1}]$$

Wherein tVWF is the truncated VWF, L1 is a chemical bond or a linker sequence, and H is a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other. Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" or to the exact "C-terminal amino acid" of the respective HLEP, or fusions to the "N-terminal part" or "C-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

Half-Life Enhancing Polypeptides (HLEPs)

Preferably, the half-life extending moiety is a half-life extending polypeptide (HLEP), more preferably HLEP is selected from albumin or fragments thereof, immunoglobulin constant region and portions thereof, e.g. the Fc fragment, solvated random chains with large hydrodynamic volume (e.g. XTEN (Schellenberger et al. 2009; Nature Biotechnol. 27:1186-1190), homo-amino acid repeats (HAP) or proline-alanine-serine repeats (PAS), afamin, alpha-fetoprotein, Vitamin D binding protein, transferrin or variants thereof, carboxyl-terminal peptide (CTP) of human chorionic gonadotropin-R subunit, polypeptides or lipids capable of binding under physiological conditions to albumin or immunoglobulin constant region.

A "half-life enhancing polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the polypeptide of the invention may be a variant of a wild type HLEP. The term "variants" includes insertions, deletions and substitutions, either conservative or non-conservative, where such changes do not substantially alter the FVIII-binding activity of the truncated VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:6 herein or albumin from other vertebrates or fragments thereof, or analogs or variants of these molecules or fragments thereof.

In particular, the proposed polypeptides of the invention may include naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants used as a HLEP of the polypeptide of the invention with enhanced binding to the FcRn receptor. Such albumin variants may lead to a longer plasma half-life of a truncated VWF albumin variant fusion protein as compared to a truncated VWF fusion with a wild-type albumin.

The albumin portion of the polypeptides of the invention may comprise at least one subdomain or domain of HA or conservative modifications thereof.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Various HLEPs which can be used in accordance with this invention are described in detail in WO 2013/120939 A1.

N-Glycans and Sialylation of the Polypeptide of the Invention

The polypeptide of the invention preferably comprises N-glycans, and at least 75%, preferably at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors found that polypeptides comprising highly sialylated VWF fragments not only have a prolonged half-life themselves, but are also capable to extend the half-life of co-administered FVIII. In other words, administration of the polypeptide of the invention leads to an extended half-life and/or to a reduced clearance of co-administered FVIII.

The polypeptide of the invention preferably comprises N-glycans, and at least 50% of the sialyl groups of the N-glycans of the glycoproteins are α-2,6-linked sialyl groups. In general, terminal sialyl groups can be attached to the galactose groups via a α-2,3- or via a α-2,6-linkage. Typically, N-glycans of the polypeptide of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2,6-sialyltransferase in mammalian cells.

In one embodiment, at least 85%, at least 90%, at least 95%, at least 96%, at least 97%, at least 98%, or at least 99%, of the N-glycans of the polypeptide of the invention comprise at least one sialic acid group. In another embodiment, at least 90%, at least 95%, at least 96%, at least 97%, at least 98%, or at least 99%, of the N-glycans of the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they do not have a sialic acid group.

Other embodiments of the invention comprise a truncated von Willebrand Factor (VWF), wherein said truncated VWF is capable of binding to a Factor VIII (FVIII), and wherein said glycoprotein comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

Still other embodiments of the invention comprise a truncated von Willebrand Factor (VWF), wherein said truncated VWF is capable of binding to a Factor VIII (FVIII), and wherein said truncated VWF comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

Dimers

It has further been found that the polypeptides of this invention have a high proportion of dimers. The polypeptide of the invention is therefore preferably present as dimer. In one embodiment, at least 50%, or at least 60%, or at least 70%, or at least 80%, or at least 90%, or at least 95% or about 100% of the polypeptides are present as dimers. In another embodiment, the ratio dimer:monomer of the polypeptide of the invention is at least 1.5, preferably at least 2, more preferably at least 2.5 or at least 3. Most preferably all polypeptides of the invention are present as dimers. The use of dimers is favorable, as the dimer has an improved affinity to Factor VIII as compared to the monomer. The dimer content, and the ratio of dimer to monomer of the polypeptide of the invention can be determined as described in Example 1.

In one embodiment, the affinity of the polypeptide of the invention to Factor VIII is greater than that of human native VWF to the same Factor VIII molecule. The factor VIII affinity may refer to human native Factor VIII, or to the Factor VIII molecule characterized by SEQ ID NO:5.

It has been found that preparations of the polypeptide of this invention with a high proportion of dimers do have an increased affinity to Factor VIII. Such increased affinity to Factor VIII does lead to an enhanced stabilization of Factor VIII by the polypeptides of the present invention. Alternatively to or in combination with an increased dimer proportion also polypeptides in accordance with the invention with mutations within the Factor VIII binding domain which do increase the affinity to Factor VIII are preferred embodiments of the invention. Suitable mutations are disclosed, e.g., in WO 2013/120939 A1.

Preparation of the Polypeptide

The nucleic acid encoding the polypeptide of the invention can be prepared according to methods known in the art. Based on the cDNA sequence of VWF (SEQ ID NO:3), recombinant DNA encoding the above-mentioned truncated VWF constructs or polypeptides of the invention can be designed and generated.

Even if the polypeptide which is secreted by the host cells does not comprise amino acids 1 to 763 of VWF, it is preferred that the nucleic acid (e.g. the DNA) encoding the intracellular precursor of the polypeptide comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:4. Most preferably, the nucleic acid (e.g. the DNA) encoding the intracellular precursor of the polypeptide comprises a nucleotide sequence encoding amino acids 23 to 763 of SEQ ID NO:4, or amino acids 1 to 763 of SEQ ID NO:4.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide of the invention into mammalian host cells.

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals N.Y. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

The cells are cultured under conditions that allow expression of the polypeptide. The polypeptide can be recovered and purified using methods that are known to the skilled artisan.

Terminal Half-Life, MRT and Clearance

Another aspect of the invention is the use of a polypeptide as defined hereinabove for increasing the terminal half-life or mean residence time (MRT) or reducing the clearance of Factor VIII. For evaluation of the pharmacokinetic data a linear pharmacokinetics model (compound elimination via the central compartment) was applied. Accordingly, any pharmacokinetic parameters used herein are based on a linear pharmacokinetics model (compound elimination via the central compartment), unless indicated otherwise.

The "half-life" $T\frac{1}{2}(t)$ at a certain time t is the time it takes to halve the plasma concentration $C(t)$ that is present at time t, i.e. $C[t+T\frac{1}{2}(t)]=C(t)/2$. The "terminal half-life" is the limit of $T\frac{1}{2}(t)$ when t tends to infinity.

The terminal half-life of administered FVIII is increased by at least 25%, preferably by at least 50%, more preferably by at least 75%, more preferably by at least 100%, most preferably by at least 150%, if an effective amount of the polypeptide of the present invention is co-administered, relative to administration of the FVIII alone. Another aspect of the invention is the use of a polypeptide as defined hereinabove for increasing the terminal half-life of Factor VIII.

The term "MRT", as used herein, means the average time a drug molecule (e.g. the polypeptide of the invention or a FVIII) resides in the body. In a linear pharmacokinetic system with constant clearance MRT can be calculated as the area under the first moment curve (AUMC) divided by the area under the plasma concentration-time curve (AUC). The first moment curve is time multiplied by plasma concentration at that time.

The MRT of administered FVIII is increased by at least 25%, preferably by at least 50%, more preferably by at least 75%, more preferably by at least 100%, most preferably by at least 150%, if an effective amount of the polypeptide of the present invention is co-administered, relative to administration of the FVIII alone. Another aspect of the invention is the use of a polypeptide as defined hereinabove for increasing the terminal half-life or mean residence time (MRT) or reducing the clearance of Factor VIII.

The term "clearance", as used herein, refers to the rate at which plasma is cleared of drug. Specifically, it is the current elimination rate of a drug divided by its current plasma concentration. In a linear pharmacokinetic system after a single intravenous administration the clearance can be calculated as the ratio of dose over the area under the plasma concentration-time curve (AUC), provided the clearance is constant. The lower the clearance the longer it takes until the plasma is cleared of the drug.

The clearance of administered FVIII is reduced by at least 10%, preferably by at least 25%, more preferably by at least 50%, more preferably by at least 60%, most preferably by at least 70%, if an effective amount of the polypeptide of the present invention is co-administered, relative to administration of the FVIII alone.

The invention further relates to a method of increasing the MRT or half-life, or to a method of reducing the clearance of Factor VIII in vivo, comprising administering to a subject an effective amount of a polypeptide as defined hereinabove.

The term "in vivo recovery of FVIII", as used herein, is defined as the percentage of FVIII, which is in the circulation extrapolated to t=0 in relation to the total amount of FVIII administered. As a basis for calculation of the expected FVIII concentration in the circulation a plasma volume of 40 mL per kg is assumed in general.

The invention further relates to the use of a polypeptide as defined hereinabove, e.g. but not limited to embodiments [01] to [72] detailed in Table 1 above, for increasing the in vivo recovery of FVIII. The in vivo recovery of FVIII is increased by at least 5%, preferably by at least 10%, more preferably by at least 15%, 18%, 20%, 25%, even more preferably by at least 26%, 27%, 28%, 29%, or 30%, most preferably by more than 35% or even more than 40% relative to the FVIII recovery without administration of the polypeptide.

A further aspect of this invention is a method of treating a blood coagulation disorder, comprising administering to a patient in need thereof an effective amount of a polypeptide as defined hereinabove.

A further aspect is the use of a polypeptide as defined hereinabove, e.g. by any of but not limited to embodiments [01] to [72] in Table 1 above, for reducing the frequency of administration of FVIII in a treatment of hemophilia A. The frequency of intravenous or subcutaneous administration of FVIII may be reduced to twice per week. Alternatively, the frequency of intravenous or subcutaneous administration of FVIII may be reduced to once per week, or even lower, e.g. to once per 10 days or once per 14 days. The FVIII may be administered twice weekly, every 5 days, once weekly, every 10 days, every two weeks, every three weeks, every four weeks or once a month, or in any range between any two of the foregoing values, for example from every four days to every month, from every 10 days to every two weeks, or from two to three times a week, etc.

Another aspect is the use of a polypeptide as defined hereinabove for reducing the dose of FVIII to be administered in a treatment of hemophilia A.

Treatment of Coagulation Disorder

The polypeptides of the invention are useful for treating coagulation disorders including hemophilia A. The term "hemophilia A" refers to a deficiency in functional coagulation FVIII, which is usually inherited.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a polypeptide of the invention is administered preferably is a human. In certain aspects, the human is a pediatric patient. In other aspects, the human is an adult patient.

Compositions comprising a polypeptide of the invention and, optionally FVIII, are described herein. The compositions typically are supplied as part of a sterile, pharmaceutical composition that includes a pharmaceutically acceptable carrier. This composition can be in any suitable form (depending upon the desired method of administering it to a patient).

The term "Factor VIII" and "FVIII" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 and other FVIII variants with mutations outside the B-domain but having the biological activity of FVIII.

The polypeptide of the invention can be administered to a patient by a variety of routes such as orally, transdermally, subcutaneously, intranasally, intravenously, intraperitoneally, intramuscularly, topically or locally. The most suitable route for administration in any given case will depend on the particular polypeptide, the subject, and the nature and severity of the disease and the physical condition of the subject. Typically, a polypeptide of the invention will be administered intravenously.

The polypeptide and the FVIII are preferably administered intravenously or subcutaneously.

In a first embodiment, both the polypeptide and the FVIII are administered intravenously. In a second embodiment, both the polypeptide and the FVIII are administered subcutaneously.

In another embodiment, the FVIII is administered intravenously, and the polypeptide is administered via a different route. In further embodiments, the polypeptide is administered subcutaneously, and the FVIII is administered via a different route. For example, the polypeptide may be administered subcutaneously, and the FVIII may be administered intravenously.

In further embodiments, the FVIII is administered subcutaneously, and the polypeptide is administered via a different route. In further embodiments, the polypeptide is administered intravenously, and the FVIII is administered via a different route. For example, the polypeptide may be administered intravenously, and the FVIII may be administered subcutaneously.

Determination of the total number of doses, and length of treatment with a polypeptide of the invention is well within the capabilities of those skilled in the art. The dosage of the polypeptide of the invention to be administered depends on the concentrations of the FVIII to be administered, the concentration of endogenous VWF in the patient to be treated, or both. An effective dosage based on the ratios defined by the inventors of this application can be determined by the skilled person, taking into account the molecular weight of the polypeptide of the invention. Typical dosages for FVIII may range from about 20 U/kg body weight to about 100 U/kg body weight.

In accordance with this invention, the patient being treated with the polypeptide of the invention is also treated with blood coagulation Factor VIII. The polypeptide of the invention and the Factor VIII may be administered simultaneously or in a sequential fashion both modes of administration being encompassed by the term "combination therapy" and "co-administration". The polypeptide of the invention and the Factor VIII may be administered as a mixture, i.e. within the same composition, or separately, i.e. as separate compositions.

The concentration of Factor VIII in the composition used is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL, provided the requirements regarding the ratio with respect to the VWF polypeptide of the invention as defined herein are fulfilled.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of Ca2+, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

Pharmaceutical Compositions

Therapeutic formulations of the polypeptide of the invention suitable in the methods described herein can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethyl-benzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a polypeptide of the invention. Examples of suitable second therapeutic agents are provided below.

The dosing schedule can vary from once a month to daily depending on a number of clinical factors, including the type of disease, severity of disease, and the patient's sensitivity to the polypeptide of the invention. In specific embodiments, a polypeptide of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, or from two to three times a week, etc.

The dosage of a polypeptide of the invention to be administered will vary according to the particular polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

The nucleotide and amino acid sequences shown in the sequence listing are summarized in the Table 2.

TABLE 2

| SEQ ID NO: | Remarks |
|---|---|
| 1 | DNA sequence encoding a polypeptide comprising amino acids 1 to 1242 of human VWF, a glycine/serine linker and human albumin; nucleotide positions (nt): <br> nt 1-6: EcoRI restriction enzyme cleavage site <br> nt 32-3757: coding sequence for VWF amino acids 1 to 1242 <br> nt 3758-3850: coding sequence for glycine/serine linker <br> nt 3851-5608: coding sequence for human albumin <br> nt 5609-5616: NotI restriction enzyme cleavage site |
| 2 | Amino acid sequence encoded by SEQ ID NO: 1 (mature form): amino acid positions (aa): <br> aa 1-479: VWF D'D3 region (VWF amino acids 764-1242) <br> aa 480-510: glycine/serine linker <br> aa 511-1195: human albumin |
| 3 | DNA sequence encoding the pre-pro form of human native VWF |
| 4 | Amino acid sequence encoded by SEQ ID NO: 3 |
| 5 | Amino acid sequence of a single chain Factor VIII molecule |
| 6 | Amino acid sequence of mature human serum albumin |
| 7 | Amino acid sequence of D'D3-His8 <br> aa 1-479: VWF D'D3 region (VWF amino acids 764-1242) <br> aa 480-511: glycine/serine linker <br> aa 512-519: polyhistidine tag |
| 8 | Amino acid sequence of D'D3-CTP <br> aa 1-479: VWF D'D3 region (VWF amino acids 764-1242) <br> aa 480-511: glycine/serine linker <br> aa 512-576: C-terminal peptide of human chorionic gonadotropin-ß subunit <br> aa 577-584: polyhistidine tag |

The following Examples illustrate the invention but should not be construed as limiting the present invention to the specific embodiments described herein below.

EXAMPLES

Aim

We aimed at investigating the impact of the ratio of a polypeptide comprising a truncated VWF and a half-life-extending moiety ("polypeptide of the invention") to FVIII and endogenous VWF, respectively, on pharmacokinetics (PK) of the fragment and FVIII.

An overview of the experiments is given in the following table.

TABLE 3

| Ex. #. | Animal | polypeptide of the invention dose | FVIII dose | Dose ratio polypeptide of the invention:FVIII | Dose ratio polypeptide of the invention:endogenous VWF |
|---|---|---|---|---|---|
| 1 | rat | Increasing (D'D3-FP) | constant | increasing | increasing |
| 2 | rat | Increasing (D'D3-FP) | increasing | constant | increasing |
| 3 | rabbit | Increasing (D'D3-FP) | constant | increasing | increasing |
| 4 | rabbit | Single dose with different recombinant FVIII products | | | |
| 5 | rat | D'D3 without half-life extending moiety and D'D3-CTP at a fixed ratio | | | |

In the pharmacokinetic examples, different molar ratios were calculated. Therefore, the following assumptions were made:

The drugs are diluted in 40 mL plasma per kg body weight after their administration Molecular weight of the polypeptide of the invention used: D'D3-FP molecular weight of monomeric subunit (including glycosylation): 127,000 Da (HLEM=human albumin)

Molecular weight of FVIII used: rVIII-SingleChain molecular weight (with glycosylation): 180,000 Da and specific activity: 11,000 IU/mg Molecular weight of albumin as part of the D'D3-FP: 66,000 Da Same molar FVIII activity of the recombinant FVIII products was used (rVIII-SingleChain, Advate®, NovoEight®), calculating for identical molar ratios when administered at same activity doses Endogenous human, rat or rabbit VWF monomer molecular weight (with 18-19% glycosylation): 267,500 Da Endogenous rat or rabbit VWF is assumed to have the same specific activity as human VWF, i.e. one U/mL (or 100% of the norm) is assumed to be 10 µg/mL (published human concentration relating to one U/mL or 100% of the norm)

Endogenous VWF activity in rat plasma measured as $0.946 \pm 0.181$ U/mL and calculated to $35.36 \times 10^{-9}$ mol/L from 12 CD rats using the INNOVANCE® VWF Ac kit (Siemens Healthcare Diagnostics GmbH, Eschborn, Germany) calibrated against standard human plasma (calibrated against the respective WHO standard, Siemens Healthcare Diagnostics GmbH)

Endogenous VWF activity in rabbit plasma measured as $0.242 \pm 0.056$ U/mL and calculated to $9.05 \times 10^{-9}$ mol/L from 5 rabbits from example 3 using the INNOVANCE® VWF Ac kit (Siemens Healthcare Diagnostics GmbH, Eschborn, Germany) calibrated against standard human plasma (calibrated against the respective WHO standard, Siemens Healthcare Diagnostics GmbH).

Example 1: Prolongation of Pharmacokinetics of FVIII by Co-Administration of rVIII-SingleChain (Constant Dose) and Increasing D'D3-FP Doses in the Rat Material and Methods Generation of D'D3 Albumin Fusion Protein (D'D3-FP):

The expression cassette for D'D3-FP consisting of cDNA encoding VWF amino acids 1 to 1242, a glycine/serine linker and the cDNA of human albumin was prepared by custom gene synthesis (Eurofins Genomics, Ebersberg, Germany). Through flanking restriction sites (EcoRI, NotI) the expression cassette was excised from the cloning vector supplied and inserted into a pIRESneo3 vector (BD Biosciences, Franklin Lakes, N.J., USA) linearized with EcoRI and NotI. The resulting expression plasmid contained nucleotide sequences encoding the VWF propeptide, D' and D3 (VWF amino acids 1 to 1242 of SEQ ID NO:4) fused to the albumin coding sequence through a short linker coding sequence under CMV promoter control. The nucleotide sequence of the coding sequence is displayed as SEQ ID NO:1, the amino acid sequence of the mature D'ID3-FP is shown as SEQ ID NO:2.

A similar approach was used to generate an expression plasmid for a His-tagged D'ID3 protein (D'D3 and His8 linked by a glycine/serine linker) and a D'D3 fusion protein to the C-terminal peptide of human chorionic gonadotropin-β subunit, also linked via a glycine/serine linker and tagged by 8 histidines at the C-terminus of the fusion protein. The amino acid sequence of the mature D'ID3-His8 is shown as SEQ ID NO: 7 and the amino acid sequence of the mature D'ID3-CTP is shown as SEQ ID NO: 8.

The expression plasmids as described above were grown up in XL10 Gold (Agilent Technologies) and purified using standard protocols (Qiagen, Hilden, Germany).

CHO K1 cells were transfected using the Lipofectamine 2000 reagent (Invitrogen) and grown up in serum-free medium (CD-CHO, Invitrogen) in the presence of 500-1000 µg/ml Geneticin. An expression plasmid encoding PACE/furin (pFu-797) as described in WO2007/144173 was cotransfected to maximize propeptide cleavage efficacy. Single cell derived clones were grown up and selected according to their D'D3-FP expression yield as quantified by an albumin specific enzyme immunoassay (see below). The cell line finally selected for D'D3-FP fermentation was called T2050-CL3.

Production of D'D3-FP was carried out in bioreactors applying a fermentation process in perfusion mode. The fermentation process for the production of D'D3-containing polypeptides started with the thaw of cell line T2050-CL3 followed by cell expansion in shake flasks and finally a fermentation process in perfusion mode using the Sartorius BioStat B-DCU 5 L bioreactor and the BioStat STR 50 L single-use bioreactors. The BioSeps 10 L or 200 L (Applikon), respectively, were used as cell retention devices. Cell culture media were either PowerCHO3 (Lonza BESP1204) with 8 mM L-glutamine and 1 µM $CuSO_4$ or ProCHO5 (Lonza BESP1072) with 10 mM L-glutamine and 1 µM $CuSO_4$.

The seed trains in shake flasks were performed at 37° C., 7.5% $CO_2$ at a shaker speed of 160 rpm.

The 5 L bioreactor was inoculated with a target VCD of $2.5 \times 10^5$ cells/mL. The cells were cultivated in PowerCHO3 with 8 mM L-glutamine and 1 µM $CuSO_4$ at a temperature of +37.0° C., a pH of 7.00, and at 30% oxygen saturation. A temperature shift to +34.0° C. (evaluated range +31° C. to +35° C.) was performed after initial harvests from the bioreactor run at +37° C. had been taken. The pH was controlled using $CO_2$ sparged as acid and $NaHCO_3$ as base. The overlay air flow rate was set to 0.5 L/min. A ring sparger was used as a sparging unit. The agitation rate was 150 rpm with a 2 fold pitch blade impeller in down pull mode.

The 50 L bioreactor was inoculated with a target VCD of $3.0 \times 10^5$ cells/mL. The cells were cultivated in ProCHO5 medium with 10 mM L-glutamine and 1 µM $CuSO_4$ at a temperature of +37.0° C., a pH of 6.90, and at 30% oxygen saturation. A temperature shift to +34.0° C. was performed after the initial one or two harvests. PH control as above, the overlay air flow rate was set to 2 L/min. A micro sparger was used as a sparging unit. The agitation rate was 90 rpm with a 2 fold pitch blade impeller in down pull mode.

The perfusion was initiated when the VCD in the bioreactor was ≥$1.0 \times 10^6$ cells/mL. The perfusion rate was set to 1.0 volume/volume/day. The BioSep was operated in back flush mode with 5 (10) minutes runtime and 10 seconds back flush at a power input of 7 (30) W (numbers in brackets refer to the 50 L bioreactor). The perfusate and the bleed were filtered inline and collected in bags over 48 hours at +2 to +8° C. The VCD was controlled by active bleeding using a turbidity probe using glucose consumption as parameter with a target of 2 g/L glucose. Harvest and bleed were filtered inline, the harvest system consisting of a disposable filter and disposable bag was changed every second day.

To prepare material for the PK analyses described below D'D3 albumin fusion protein harvests were purified by affinity and size exclusion chromatography. Briefly, the cell-free harvest from the bioreactor was concentrated 30-fold using a TFF system (e.g. Pall Centramate 500 S) with a 30 kD membrane (e.g Pall Centramate OS030T12). That concentrate was spiked with NaCl and EDTA to a final concentration of 0.75 M NaCl and 5 mM EDTA and loaded overnight on a CaptureSelect Human Albumin column (Life Technologies) which was pre-equilibrated with 20 mM Tris buffer pH 7.4. After washing the column with equilibration buffer D'D3-FP was eluted with elution buffer (20 mM Tris, 2 M $MgCl_2$, pH 7.4). The eluate was then 10-fold concentrated and dialyzed against 50 mM Tris, 150 mM NaCl, pH 7.4 using Ultra Centrifugal Filters with a 30 kD cut-off (e.g. Amicon. UFC903024). To separate the D'D3-FP dimer from the monomer portion that material was loaded on a Superdex 200 µg column (GE Healthcare Code: 17-1069-01) pre-equilibrated with 50 mM Tris, 150 mM NaCl, pH 7.4 and the peak fractions containing the D'D3-FP dimer were pooled. The area under the curve for the dimer and monomer peak fractions were used to calculate dimer to monomer ratio. Dimer preparations of D'D3-FP were used for the pharmacokinetic experiments in Examples 1-4.

His-tagged D'D3 proteins were purified by Ni-chelate affinity and size exclusion chromatography. Briefly, TFF concentrated cell-free bioreactor harvest (see above for details) was loaded on a preequilibrated (20 mM sodium phosphate/500 mM NaCl, pH 7.4) Ni-Sepharose column (HisTrap™, GE Healthcare) over night. After washing the column with 20 mM sodium phosphate/500 mM NaCl/30 mM Imidazol, pH 7.4 the protein was eluted with 20 mM sodium phosphate+500 mM NaCl+500 mM Imidazol, pH 7.4. The eluate was then concentrated and dialysed (TBS, pH7.4) using an Amicon Ultra Centrifugal Filter (see above). The final product was then loaded onto a SEC column (see above), the peak fractions containing the dimer were pooled and concentrated to about 7 mg/mL $OD_{280-320}$.

Animals:

Female Crl:CD (Sprague Dawley) rats in a weight range of 240-300 g were bred at Charles River Laboratories (Sulzfeld, Germany). In house, the animals were kept at standard housing conditions, i.e. at 21-22° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations. The group size was n=6, divided in 2 cohorts. Thus, n=3 animals per time-point were used.

Laboratory Evaluations:

The test articles were administered i.v. by a single injection into the lateral tail vein at a total volume of 3 mL/kg. D'D3-FP preparations were applied at dose levels from 50 to 10,000 μg/kg based on human albumin values, and co-administered with 200 IU/kg rVIII-SingleChain (rVIII-SingleChain, chromogenic activity) after incubating for approximately 30 minutes at +37° C. Animals receiving only rVIII-SingleChain served as control (Table 4). This led to administered molar ratios of D'D3-FP (calculated as monomer) over rVIII-SingleChain ranging from 7.5 to 1500 as well as a molar ratio of D'D3-FP over endogenous rat VWF (both as monomers to adjust for FVIII binding sites) from 0.54 to 107.1.

Blood samples were taken retroorbitally under short term anaesthesia at 5 min, 3, 8, 24, 32, 48, 56 and 72 h after intravenous bolus injection using an alternating sampling scheme. The PK profile was taken from two cohorts of rats per group. Blood samples were anticoagulated using sodium citrate (2 parts sodium citrate 3.13%+8 parts blood), processed to plasma and stored at −20° C. for the determination of FVIII antigen and/or albumin.

D'D3-FP exposure was determined by measurement of the albumin part of the construct using a human albumin ELISA. Accordingly, any amount or dose of D'D3-FP is indicated as the amount or dose of albumin. Other D'D3-containing polypeptides were detected with a D'D3 specific Elisa. FVIII:Ag plasma levels were detected with the FVIII Asserachrom ELISA testkit from Stago, S.A.S., France.

D'D3-albumin fusions were measured in plasma samples in an Elisa with a commercial polyclonal antibody preparation. For capture and detection the same antibodies were used, except that the detection antibodies were POD labelled. Briefly, each well of a 96-well plate (Nunc Immuno-Plate Maxisorp, product number 449824) was coated with 100 μL of coating solution (goat anti-human Albumin-IgG, Cat. No. A80-129A, Bethyl Laboratories, diluted to 2 μg/mL in 50 mM coating buffer (Carbonate-Bicarbonate Capsules, Sigma product No.: C-3041)) and incubated at +21° C. for 2-20 hours. The coating procedure was followed by 3 wash steps using wash buffer (phosphate buffered saline with tween 20, Sigma product No.: P3563). Subsequent blocking was performed for 1.5 h at +21° C., with blocking solution (Candor Biosience, Cat. No. 110500) followed by another 3 wash steps. Subsequently 100 μl of each sample were applied to the plate and incubated for 1 h at +37° C. As standards the respective injection solutions of the substances tested were diluted with sample buffer (Low Cross Buffer, Candor Biosience, Cat. No. 100500) to concentrations from 50 ng/mL to 0.78 ng/mL in 2 step decrements. The citrated plasma samples, taken from the animals were also diluted with sample buffer at least 1:30, sample buffer was also applied as blank. After another four washing steps, 100 μL of detection solution (POD labelled anti human albumin-IgG, Cat. No. A80-129P, Bethyl Laboratories, diluted 1:40000 in blocking solution solution) was applied to each well for 45 min at +37° C. After another four washing steps, 100 μL per well of chromogenic substrate (TMB, Siemens Healthcare product OUVF, OUVG) was applied for 20 min, followed by addition of another 100 μl stop solution (OSFA, Siemens Healthcare) per well. The plates were measured in a plate reader at 450/650 nm.

D'D3-containing polypeptides without albumin were measured in plasma samples with an anti-D'D3 sandwich ELISA with proprietary anti-D'D3 antibodies. Briefly, each well of a 96-well plate (Nunc Immuno-Plate Maxisorp, product number 449824) was coated with 100 μL of coating solution (D'D3 capture antibody diluted to 1 μg/mL in 50 mM coating buffer (Carbonate-Bicarbonate Capsules, Sigma product No.: C-3041)) and incubated at +21° C. for 16 hours. The coating procedure was followed by 3 wash steps using wash buffer (Tris buffer saline with tween 20, Sigma product No.: T9039). Blocking was performed for 1.5 h at +21° C., with blocking solution (Candor Biosience, Cat. No. 110500), followed by another 3 wash steps. Subsequently 100 μl each of each sample were applied to the plate and incubated for 1.5 h at +21° C. As standards the respective injection solutions of the substances tested were diluted with sample buffer (Tris buffer saline with tween 20, Sigma product No.: T9039) to concentrations from 70 ng/mL to 1.1 ng/mL in 2 step decrements. The citrated plasma samples were also diluted with sample buffer at least 1:30, sample buffer was also applied as blank. After another three washing steps, 100 μL of detection solution (POD labelled anti D'D3 detection antibody (proprietary research grade preparation), diluted to 0.2 μg/mL in sample buffer) was applied to each well and incubated for 1 h at +21° C. After another three washing steps, 100 μL per well of chromogenic substrate (TMB, Siemens Healthcare product No.: OUVF, OUVG) was applied for 30 min, followed by another 100 μl stop solution (OSFA, Siemens Healthcare) per well. The plates were measured in a plate reader at 450/650 nm.

Estimation of mean residence time (MRT), clearance (CL) and terminal half-life (t½) was done by non-compartmental methods.

TABLE 4

| | | Treatment groups | | | |
|---|---|---|---|---|---|
| No. | Treatment | D'D3-FP dose [mg albumin/kg] | FVIII dose [IU FVIII:C/kg] | Molar ratio D'D3-FP*:rVIII-SC | Molar ratio D'D3-FP* over rat VWF** |
| 1 | rVIII-SC | — | 200 | — | — |
| 3 | D'D3-FP & rVIII-SC | 0.05 | 200 | 7.5 | 0.54 |

TABLE 4-continued

| No. | Treatment | D'D3-FP dose [mg albumin/kg] | FVIII dose [IU FVIII:C/kg] | Molar ratio D'D3-FP*:rVIII-SC | Molar ratio D'D3-FP* over rat VWF** |
|---|---|---|---|---|---|
| 4 | D'D3-FP & rVIII-SC | 0.10 | 200 | 15 | 1.07 |
| 5 | D'D3-FP & rVIII-SC | 0.20 | 200 | 30 | 2.14 |
| 6 | D'D3-FP & rVIII-SC | 0.50 | 200 | 75 | 5.36 |
| 7 | D'D3-FP & rVIII-SC | 1.00 | 200 | 150 | 10.7 |
| 8 | D'D3-FP & rVIII-SC | 2.00 | 200 | 300 | 21.4 |
| 9 | D'D3-FP & rVIII-SC | 5.00 | 200 | 750 | 53.6 |
| 10 | D'D3-FP & rVIII-SC | 10.00 | 200 | 1500 | 107.1 |

FVIII:C = chromogenic FVIII activity; rVIII-SC = rVIII-SingleChain
*D'D3-FP calculated as monomer
**D'D3-FP calculated as monomer over endogenous VWF monomer to compare same numbers of FVIII binding sites. For calculation of the endogenous rat VWF the same specific activity as human VWF was assumed, i.e. one U/mL (or 100% of the norm) is assumed to be 10 µg/mL (measured rat plasma concentration 0.946 U/mL)

Results

Figure 1A:
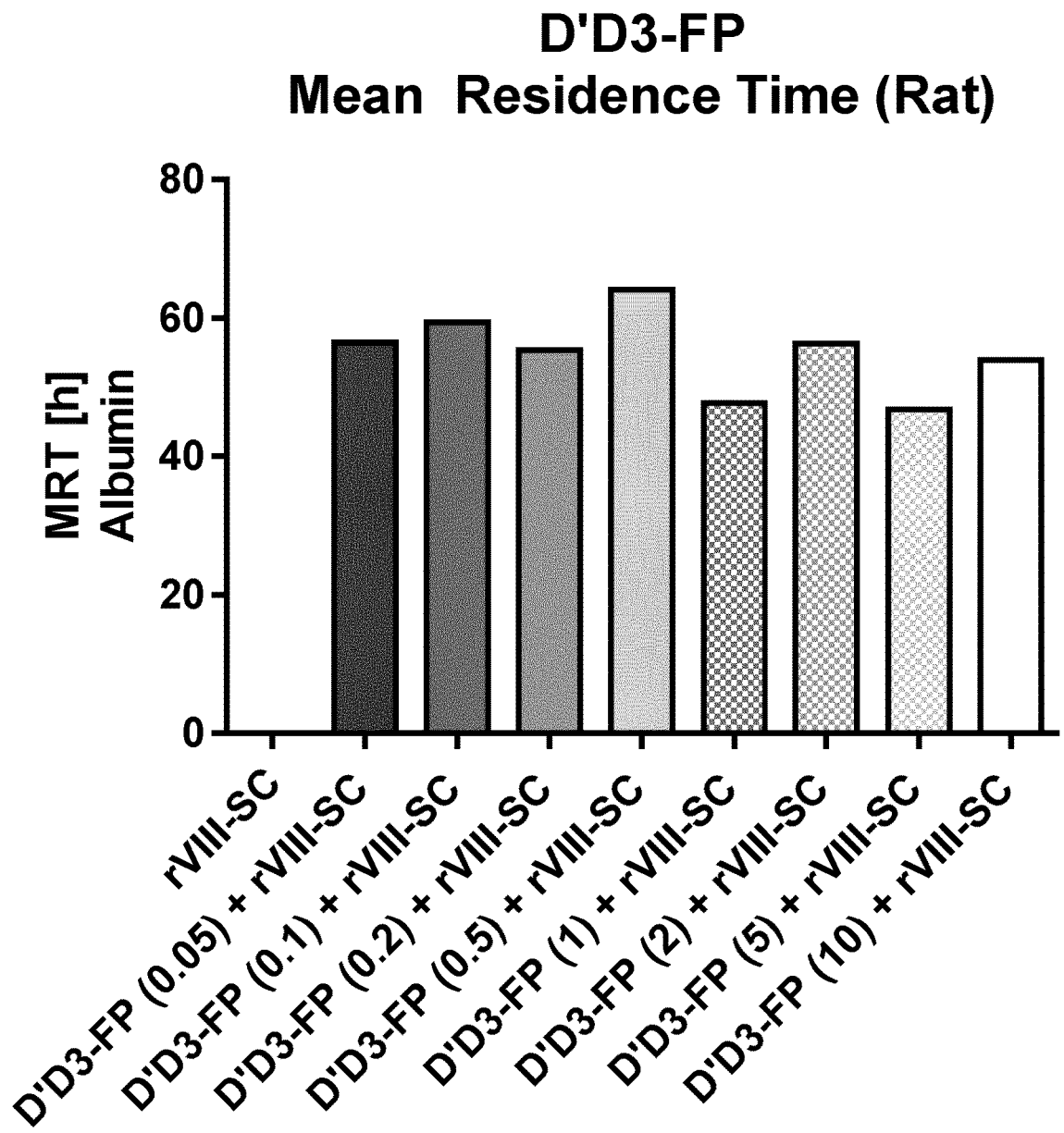
FIG. 1: Mean residence time, terminal half-life and clearance (mean) of D'D3-FP quantified by determining the albumin moiety in rats (Example 1).
Figure 1B:
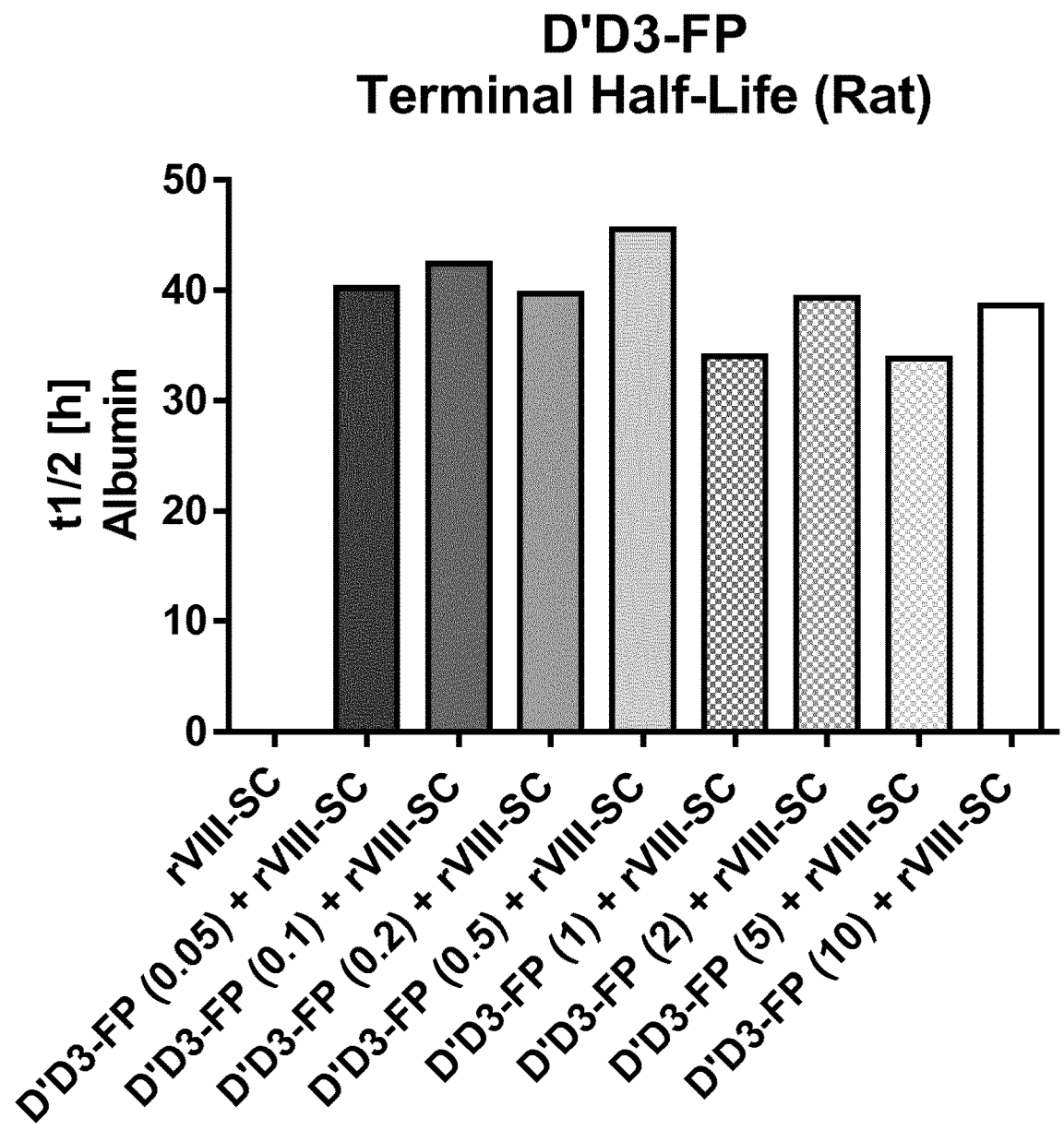
Figure 1C:
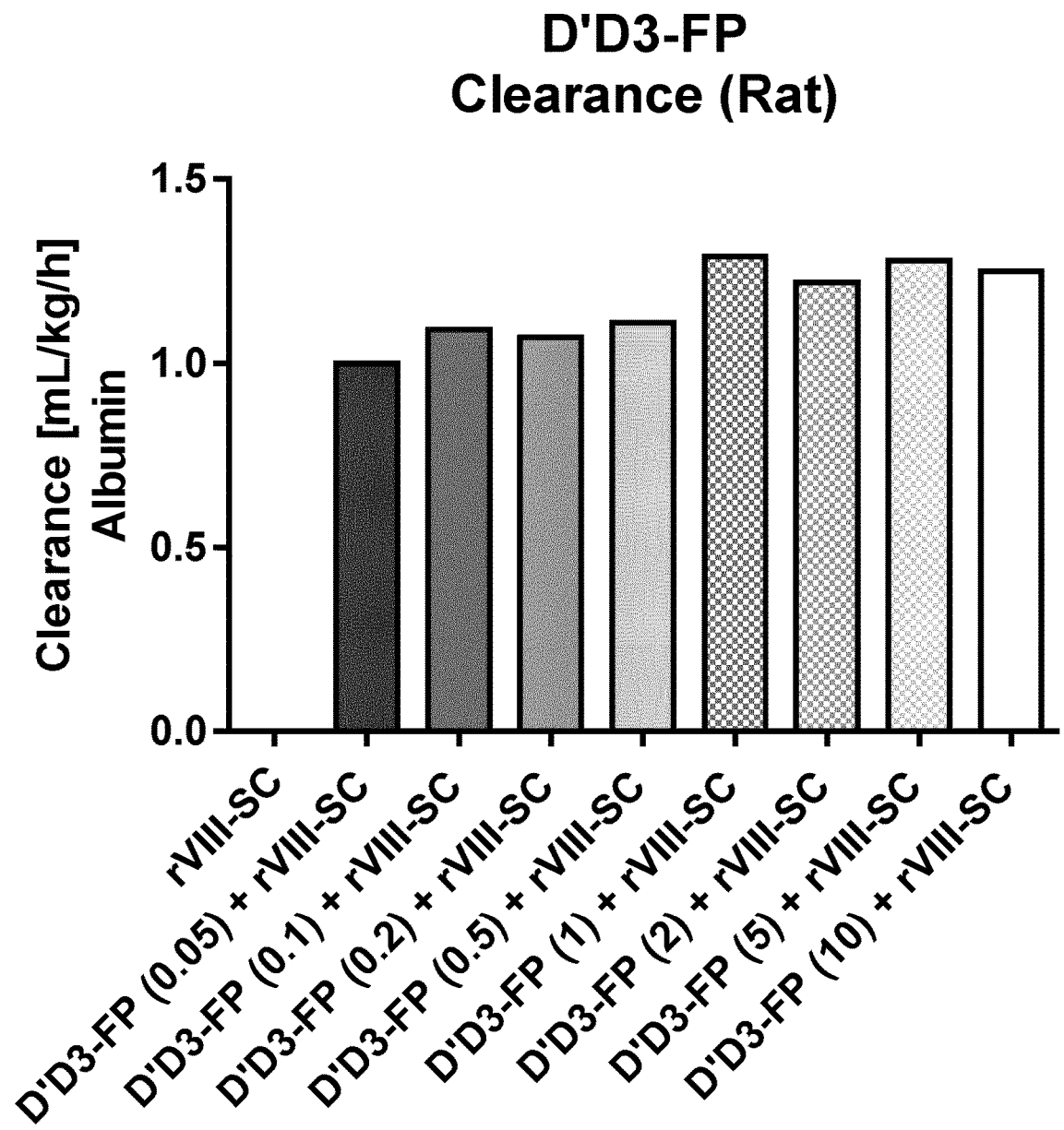

D'D3-FP was quantified by determining the albumin component, followed by calculation of the D'D3-FP concentration, and all measured data (up to 72 h p.a.) were well above the detection limit of the assay. The ELISA used specifically detected human albumin. Mean residence time (MRT) and clearance of D'D3-FP were not affected by the given dose in a range from 0.05 to 10 mg/kg i.v. (FIG. 1 and Table 5).

The exposure of the co-administered FVIII (200 IU/kg chromogenic FVIII activity), quantified as FVIII:Ag via ELISA, was prolonged in the presence of D'D3-FP (FIG. 2 and Table 5). Thus, in the rVIII-SingleChain group, FVIII:Ag reached the detection limit of 117 mIU/mL at 24-32 h p.a., while the D'D3-FP co-treated groups had dose-dependently increased plasma concentrations and did not reach the detection limit up to 72 h p.a. in the groups co-treated with 5 and 10 mg/kg.

Already the lowest dose of 0.05 mg/kg i.v. of D'D3-FP increased MRT and terminal half-life and slightly reduced clearance of rVIII-SingleChain. Up to 0.2 mg/kg only minor changes were seen on MRT, terminal half-life and clearance, and from 0.5 to 10 mg/kg a dose-dependent increase was seen for MRT and terminal half-life or decrease for clearance. It is thus concluded that in this experimental setting an about 75-fold excess of D'D3-FP (the 0.5 mg/kg dose) over rVIII-SingleChain is needed to relevantly prolong FVIII half-life.

It is assumed that at lower doses of D'D3-FP, the endogenous rat VWF competes with D'D3-FP for binding to the co-administered FVIII more relevantly than at higher doses, thereby explaining the dose-dependence of D'D3-FP dose on FVIII PK.

Calculation of increases of MRT and terminal half-life and decreases of clearance as compared to rVIII-SingleChain given alone is presented in Table 5. Co-administration of rVIII-SingleChain with 0.05-0.2 mg/kg D'D3-FP reduced clearance and prolonged MRT and terminal half-life by less than a factor of 2. Starting from 0.5 mg/kg (molar ratio D'D3-FP over rVIII-SingleChain=75; molar ratio over endogenous rat VWF=5.36), a dose-dependent reduction of clearance and increase of MRT and terminal half-life can be seen. Even at a dose of 10 mg/kg D'D3-FP (molar ratio D'D3-FP over rVIII-SingleChain=1500; molar ratio over endogenous rat VWF=107.1), a further change over the lower dose was seen, suggesting that the plateau of the effect was not yet reached.

TABLE 5

Pharmacokinetic parameters of D'D3-FP and FVIII:Ag after co-administration of rVIII-SingleChain and D'D3-FP in rats (non-compartmental analysis)
Dose D'D3-FP 0.05 to 10 mg/kg, dose rVIII-SingleChain 200 IU/kg

| No. | Treatment* | $C_{max}$, extrap. µg/mL (D'D3-FP $^c$) IU/mL (FVIII:Ag) | Clearance mL/kg/h | MRT h | Half-life, terminal h |
|---|---|---|---|---|---|
| | | D'D3-FP | | | |
| 3 | D'D3-FP (0.05) & rVIII-SC | 1.27 | 1.00 | 56.6 | 40.2 |
| 4 | D'D3-FP (0.1) & rVIII-SC | 2.33 | 1.09 | 59.5 | 42.4 |
| 5 | D'D3-FP (0.2) & rVIII-SC | 5.15 | 1.07 | 55.4 | 39.7 |
| 6 | D'D3-FP (0.5) & rVIII-SC | 9.47 | 1.11 | 64.1 | 45.5 |
| 7 | D'D3-FP (1) & rVIII-SC | 23.80 | 1.29 | 47.7 | 34.0 |
| 8 | D'D3-FP (2) & rVIII-SC | 36.24 | 1.22 | 56.4 | 39.3 |
| 9 | D'D3-FP (5) & rVIII-SC | 115.17 | 1.28 | 46.8 | 33.8 |
| 10 | D'D3-FP (10) & rVIII-SC | 221.84 | 1.25 | 54.0 | 38.6 |
| | | FVIII:Ag | | | |
| 1 | rVIII-SC | 3.36 | 8.25 | 7.4 | 5.2 |
| 3 | D'D3-FP (0.05) & rVIII-SC | 4.41 | 4.93 (1.7fold$^a$) | 10.5 (1.4fold$^b$) | 7.1 (1.4fold$^b$) |

TABLE 5-continued

Pharmacokinetic parameters of D'D3-FP and FVIII:Ag after co-administration of rVIII-SingleChain and D'D3-FP in rats (non-compartmental analysis) Dose D'D3-FP 0.05 to 10 mg/kg, dose rVIII-SingleChain 200 IU/kg

| No. | Treatment* | $C_{max}$, extrap. µg/mL (D'D3-FP [c]) IU/mL (FVIII:Ag) | Clearance mL/kg/h | MRT h | Half-life, terminal h |
|---|---|---|---|---|---|
| 4 | D'D3-FP (0.1) & rVIII-SC | 4.52 | 4.72 (1.7fold[a]) | 10.8 (1.5fold[b]) | 7.7 (1.5fold[b]) |
| 5 | D'D3-FP (0.2) & rVIII-SC | 4.35 | 4.72 (1.7fold[a]) | 11.9 (1.6fold[b]) | 8.4 (1.6fold[b]) |
| 6 | D'D3-FP (0.5) & rVIII-SC | 3.93 | 3.78 (2.2fold[a]) | 15.1 (2.0fold[b]) | 10.5 (2.0fold[b]) |
| 7 | D'D3-FP (1) & rVIII-SC | 4.28 | 2.83 (2.9fold[a]) | 16.7 (2.3fold[b]) | 11.0 (2.1fold[b]) |
| 8 | D'D3-FP (2) & rVIII-SC | 4.62 | 2.18 (3.8fold[a]) | 19.9 (2.7fold[b]) | 13.9 (2.7fold[b]) |
| 9 | D'D3-FP (5) & rVIII-SC | 4.82 | 1.85 (4.5fold[a]) | 25.8 (3.5fold[b]) | 17.6 (3.4fold[b]) |
| 10 | D'D3-FP (10) & rVIII-SC | 4.63 | 1.68 (4.9fold[a]) | 29.6 (4.0fold[b]) | 20.3 (3.9fold[b]) | rVIII-SC = rVIII-SingleChain
[a] fold decrease over data from rVIII-SingleChain given alone
[b] fold increase over data from rVIII-SingleChain given alone
[c] determination of albumin in µg/mL Example 2: Prolongation of Pharmacokinetics of FVIII by Co-Administration of rVIII-SingleChain and D'D3-FP at Different Doses (Constant in D'D3-FP: rVIII-SingleChain Ratio) in the Rat Material and Methods Animals: Female Crl:CD (Sprague Dawley) rats in a weight range of 220-270 g were bred at Charles River Laboratories (Sulzfeld, Germany). In house, the animals were kept at standard housing conditions, i.e. at 21-22° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations.

The group size was n=6, divided in 2 cohorts. Thus, n=3 animals per time-point were used.

Laboratory evaluations: The test articles were administered i.v. by a single injection into the lateral tail vein at a total volume of 4.5 mL/kg. D'D3-FP preparations were applied at dose levels from 1 to 10 mg/kg based on human albumin values, and co-administered with 100 to 1000 IU/kg rVIII-SingleChain (rVIII-SingleChain, chromogenic activity) at constant D'D3-FP to rVIII-SingleChain ratios after incubating for approximately 30 minutes at +37° C. Animals receiving only rVIII-SingleChain served as control (Table 6).

Blood samples were taken retro-orbitally under short term anaesthesia at 5 min, 3, 8, 24, 32, 48, 56 and 72 h after intravenous bolus injection using an alternating sampling scheme. The PK profile was taken from two cohorts of rats per group. Blood samples were anticoagulated using sodium citrate (2 parts sodium citrate 3.13%+8 parts blood), processed to plasma and stored at −20° C. for the determination of FVIII antigen and/or albumin.

D'D3-FP exposure was determined by measurement of the albumin part of the construct using a human albumin ELISA. Accordingly, any amount or dose of D'D3-FP is indicated as the amount or dose of albumin. FVIII:Ag plasma levels were detected with the FVIII Asserachrom ELISA testkit from Stago, S.A.S., France.

Estimation of mean residence time (MRT), clearance (CL) and terminal half-life (t½) was done by non-compartmental methods.

TABLE 6

Treatment groups

| No | Treatment | D'D3-FP dose [mg albumin/kg] | FVIII dose [IU FVIII:C/kg] | Molar ratio D'D3-FP* over rVIII-SC | Molar ratio D'D3-FP* over rat VWF ** |
|---|---|---|---|---|---|
| 1 | rVIII-SC (100) | — | 100 | — | — |
| 2 | D'D3-FP (1) & rVIII-SC (100) | 1 | 100 | 300 | 10.7 |
| 3 | rVIII-SC (300) | — | 300 | — | — |
| 4 | D'D3-FP (3) & rVIII-SC (300) | 3 | 300 | 300 | 32.1 |
| 5 | rVIII-SC (1000) | — | 1000 | — | — |

TABLE 6-continued

| No | Treatment | D'D3-FP dose [mg albumin/kg] | FVIII dose [IU FVIII:C/kg] | Molar ratio D'D3-FP* over rVIII-SC | Molar ratio D'D3-FP* over rat VWF ** |
|---|---|---|---|---|---|
| 6 | D'D3-FP (10) & rVIII-SC (1000) | 10 | 1000 | 300 | 107.1 |

FVIII:C = chromogenic FVIII activity; rVIII-SC = rVIII-SingleChain
*D'D3-FP calculated as monomer
** D'D3-FP calculated as monomer over endogenous VWF monomer to compare same numbers of FVIII binding sites. For calculation of the endogenous rat VWF the same specific activity as human VWF was assumed, i.e. one U/mL (or 100% of the norm) is assumed to be 10 µg/mL (measured rat plasma concentration 0.946 U/mL)

Results

D'D3-FP was quantified via its albumin component, and all measured data (up to 72 h p.a.) were well above the detection limit of the assay. Mean residence time (MRT) and clearance of D'D3-FP were not affected by the given dose in the range from 1 to 10 mg/kg i.v. (FIG. 3 and Table 7, compare FIG. 1 and Table 5).

The exposure of the co-administered FVIII (100 to 1000 IU/kg chromogenic FVIII activity), quantified as FVIII:Ag via ELISA, was prolonged in the presence of D'D3-FP (FIG. 4 and Table 7). With the dose-dependency of FVIII exposure, the low dose rVIII-SingleChain group reached the FVIII:Ag detection limit of 117 mIU/mL already at 24 h p.a., while higher doses reached the detection limit later, and longest profiles were observed with co-treatment with D'D3-FP, especially both high dose D'D3-FP co-treated groups did not reach the detection limit up to 72 h p.a.

Pharmacokinetic characteristics of FVIII were not affected by the FVIII dose. As stated before, D'D3-FP pharmacokinetics were also not affected by the D'D3-FP dose.

TABLE 7

Pharmacokinetic parameters of D'D3-FP and FVIII:Ag after co-administration of rVIII-SingleChain and D'D3-FP in rats (non-compartmental analysis) Dose D'D3-FP 1 to 10 mg/kg, dose rVIII-SingleChain 100 to 1000 IU/kg, constant D'D3-FP to rVIII-SingleChain ratio.

| Treatment* | $C_{max}$, extrap. µg/mL (D'D3-FP $^c$) IU/mL (FVIII:Ag) | Clearance mL/kg/h | MRT h | Half-life, terminal h |
|---|---|---|---|---|
| D'D3-FP | | | | |
| D'D3-FP (1 mg/kg) & rVIII-SC (100 IU/kg) | 18.0 | 1.26 | 67.1 | 48.0 |
| D'D3-FP (3 mg/kg) & rVIII-SC (300 IU/kg) | 67.3 | 1.22 | 52.8 | 37.7 |
| D'D3-FP (10 mg/kg) & rVIII-SC (1000 IU/kg) | 234.6 | 1.09 | 58.4 | 42.3 |
| FVIII:Ag | | | | |
| rVIII-SC (100 IU/kg) | 1.50 | 9.99 | 6.4 | 4.5 |
| D'D3-FP (1 mg/kg) & rVIII-SC (100 IU/kg) | 2.03 | 3.42 (2.9fold$^a$) | 15.7 (2.5fold$^b$) | 10.8 (2.4fold$^b$) |
| rVIII-SC (300 IU/kg) | 5.45 | 8.78 | 7.9 | 5.8 |
| D'D3-FP (3 mg/kg) & rVIII-SC (300 IU/kg) | 6.04 | 2.41 (3.6fold$^a$) | 23.0 (2.9fold$^b$) | 15.7 (2.7fold$^b$) |
| rVIII-SC (1000 IU/kg) | 19.03 | 12.42 | 6.8 | 5.2 |
| D'D3-FP (10 mg/kg) & rVIII-SC (1000 IU/kg) | 24.46 | 1.64 (7.6fold$^a$) | 30.2 (4.4fold$^b$) | 20.5 (3.9fold$^b$) | rVIII-SC = rVIII-SingleChain
$^a$fold decrease over data from rVIII-SingleChain given alone
$^b$fold increase over data from rVIII-SingleChain given alone
$^c$ determination of albumin in µg/mL Example 3: Prolongation of Pharmacokinetics of FVIII by Co-Administration of rVIII-SingleChain (Constant Dose) and Increasing D'D3-FP Doses in the Rabbit Material and Methods Animals: Female CHB rabbits in a weight range of 2.2-2.8 kg (Bauer, Neuental, Germany) were housed one per cage in wire-steel cages at standard housing conditions, i.e. at 21-23° C. and 50% relative humidity under a 12 h/12 h light-darkness cycle. The animals were provided tap water ad libitum and fed rabbit pellets (Deukanin®, Deutsche Tiernahrung Cremer GmbH & Co. KG, Dusseldorf, Germany). Animal husbandry and study procedures complied with the German Animal Welfare law and European Union regulations.

Laboratory evaluations: The test articles were administered i.v. by a single injection into the lateral ear vein, with a group size of n=3 animals per group. D'D3-FP preparations were applied at a dose level of 0.5 to 3 mg/kg based on human albumin values, and co-administered with 150 IU/kg rVIII-SingleChain (rVIII-SingleChain, chromogenic activity) after incubating for approximately 30 minutes at +37° C. Animals receiving only rVIII-SingleChain served as control (Table 8).

Blood samples were taken from the ear artery at pre-dose, 5 and 30 min, 1, 2, 4, 6, 8, 24, 32, 48, 72 and 96 h (rVIII-SingleChain) or pre-dose, 5 min, 1, 4, 8, 24, 32, 48, 72, 96, 120, 144 and 168 h (rVIII-SingleChain co-treated with D'D3-FP) after intravenous bolus injection.

Blood samples were anticoagulated using sodium citrate (2 parts sodium citrate 3.13%+8 parts blood), processed to plasma and stored at −20° C. for the determination of FVIII antigen and/or D'D3-FP. D'D3-FP exposure was determined by measurement of the albumin part of the construct using a human albumin-specific ELISA. Accordingly, any amount or dose of D'D3-FP is indicated as the amount or dose of albumin. FVIII:Ag plasma levels were detected by ELISA (Asserachrom Stago, S.A.S., France).

Estimation of mean residence time (MRT), clearance (CL) and terminal half-life (t½) was done by non-compartmental methods.

TABLE 8

Treatment groups

| Treatment* | D'D3-FP dose [mg albumin/kg] | FVIII dose [IU FVIII:C/kg] | Volume [mL/kg] | Molar ratio D'D3-FP* over rVIII-SC | Molar ratio D'D3-FP* over rabbit VWF** |
|---|---|---|---|---|---|
| rVIII-SC | — | 150 | 0.434 | — | — |
| D'D3-FP & rVIII-SC | 0.5 | 150 | 0.519 | 100 | 20.9 |
| D'D3-FP & rVIII-SC | 1.5 | 150 | 0.688 | 300 | 62.8 |
| D'D3-FP & rVIII-SC | 3.0 | 150 | 0.943 | 600 | 125.6 |

FVIII:C = chromogenic FVIII activity; rVIII-SC = rVIII-SingleChain
*D'D3-FP calculated as monomer
**D'D3-FP calculated as monomer over endogenous VWF monomer to compare same numbers of FVIII binding sites. For calculation of the endogenous rabbit VWF the same specific activity as human VWF was assumed, i.e. one U/mL (or 100% of the norm) is assumed to be 10 µg/mL (measured rabbit plasma concentration 0.242 U/mL)

Results

In general, results in rats and rabbits are very comparable. The following observations were made in detail:

D'D3-FP was quantified via its albumin component; and measurements were well above the detection limit of the assay up to the measured 168 h p.a. The increase in dose in the range from 0.5 to 3 mg/kg did not affect MRT and clearance (FIG. 5) or terminal half-life (Table 9).

The exposure of the co-administered FVIII (150 IU/kg chromogenic FVIII activity), quantified as FVIII:Ag via ELISA, was relevantly prolonged in the presence of D'D3-FP (FIG. 6). In the rabbit, plasma levels of FVIII:Ag could be measured maximally up to 48 h p.a. when rVIII-SingleChain was given alone (detection limit of 117 mIU/mL), and maximally up to the last time-point of 168 h p.a. after co-treatment with 3 mg/kg D'D3-FP. Like in the rat, this prolongation of PK was dose-dependent.

TABLE 9

Pharmacokinetic parameters of D'D3-FP and FVIII:Ag after co-administration of rVIII-SingleChain and D'D3-FP in rabbits (non-compartmental analysis)
Dose D'D3-FP 0.5-3 mg/kg, dose rVIII-SingleChain 150 IU/kg

| Treatment* | Cmax, extrap. µg/mL (D'D3-FP $^c$) IU/mL (FVIII:Ag) | Clearance mL/kg/h | MRT h | Half-life, terminal h |
|---|---|---|---|---|
| D'D3-FP | | | | |
| D'D3-FP (0.5 mg/kg) & rVIII-SC | 7.0 | 0.516 | 181 | 126 |
| D'D3-FP (1.5 mg/kg) & rVIII-SC | 22.0 | 0.638 | 154 | 107 |

TABLE 9-continued

Pharmacokinetic parameters of D'D3-FP and FVIII:Ag after co-administration
of rVIII-SingleChain and D'D3-FP in rabbits (non-compartmental analysis)
Dose D'D3-FP 0.5-3 mg/kg, dose rVIII-SingleChain 150 IU/kg

| Treatment* | Cmax, extrap. µg/mL (D'D3-FP [c]) IU/mL (FVIII:Ag) | Clearance mL/kg/h | MRT h | Half-life, terminal h |
|---|---|---|---|---|
| D'D3-FP (3 mg/kg) & rVIII-SC | 48.2 | 0.493 | 150 | 104 |
| FVIII:Ag | | | | |
| rVIII-SC | 2.51 | 3.71 | 23.2 | 17.3 |
| D'D3-FP (0.5 mg/kg) & rVIII-SC | 2.59 | 1.79 (2.1fold[a]) | 33.0 (1.4fold[b]) | 21.2 (1.2fold[b]) |
| D'D3-FP (1.5 mg/kg) & rVIII-SC | 2.84 | 1.37 (2.7fold[a]) | 47.3 (2.0fold[b]) | 32.6 (1.9fold[b]) |
| D'D3-FP (3 mg/kg) & rVIII-SC | 2.38 | 0.98 (3.8fold[a]) | 64.2 (2.8fold[b]) | 43.9 (2.5fold[b]) | rVIII-SC = rVIII-SingleChain
[a] fold decrease over data from rVIII-SingleChain given alone
[b] fold increase over data from rVIII-SingleChain given alone
[c] determination of albumin in µg/mL Calculation of increases of clearance, MRT and terminal half-life of FVIII:Ag is presented in Table 9. The lowest co-administered dose of 0.5 mg/kg (molar ratio D'D3-FP over rVIII-SingleChain=100) already relevantly prolong FVIII:Ag exposure. The increase in D'D3-FP dose to 3 mg/kg (molar ratio D'D3-FP over rVIII-SingleChain=600) led to an at least 2.5 fold prolongation of FVIII:Ag MRT and terminal half-life and a 2.5 fold reduction of clearance of FVIII:Ag.

Example 4: Prolongation of Pharmacokinetics of FVIII by Co-Administration of Different Recombinant FVIII Products with D'D3-FP in the Rabbit Material and Methods Animals: Female CHB rabbits in a weight range of 2.2-2.8 kg (Bauer, Neuental, Germany) were housed one per cage in wire-steel cages at standard housing conditions, i.e. at 21-23° C. and 50% relative humidity under a 12 h/12 h light-darkness cycle. The animals were provided tap water ad libitum and fed rabbit pellets (Deukanin®, Deutsche Tiernahrung Cremer GmbH & Co. KG, Dusseldorf, Germany). Animal husbandry and study procedures complied with the German Animal Welfare law and European Union regulations.

Laboratory evaluations: The test articles were administered i.v. by a single injection into the lateral ear vein, with a group size of n=3 animals per group. D'D3-FP preparations were applied at a dose level of 1.5 mg/kg based on human albumin values, and co-administered with 150 IU/kg rVIII-SingleChain (rVIII-SingleChain, dosed according to measured chromogenic activity), 150 IU/kg Advate® (recombinant full length FVIII, dosed according to label) or 150 IU/kg NovoEight® (recombinant B-domain-deleted FVIII, dosed according to label) after incubating for approximately 30 minutes at +37° C. Animals receiving only 150 IU/kg rVIII-SingleChain, Advate® or NovoEight® served as control (Table 10).

Blood samples were taken from the ear artery at pre-dose, 5 and 30 min, 1, 2, 4, 6, 8, 24, 32, 48, 72 and 96 h (recombinant FVIII products alone) or pre-dose, 5 min, 1, 4, 8, 24, 32, 48, 72, 96, 120, 144 and 168 h (recombinant FVIII products co-treated with D'D3-FP) after intravenous bolus injection. Blood samples were anticoagulated using sodium citrate (2 parts sodium citrate 3.13%+8 parts blood), processed to plasma and stored at −20° C. for the determination of FVIII antigen and/or D'D3-FP. D'D3-FP exposure was determined by measurement of the albumin part of the construct using a human albumin ELISA. Accordingly, any amount or dose of D'D3-FP is indicated as the amount or dose of albumin. FVIII:Ag plasma levels were detected by ELISA (Asserachrom Stago, S.A.S., France).

Estimation of mean residence time (MRT), clearance (CL) and terminal half-life (t½) was done by non-compartmental methods.

TABLE 10

| | Treatment groups | | | | |
|---|---|---|---|---|---|
| Treatment* | D'D3-FP dose [mg albumin/kg] | FVIII dose [IU/kg] | Volume [mL/kg] | Molar ratio D'D3-FP* over rFVIII | Molar ratio D'D3-FP* over rabbit VWF** |
| rVIII-SC | — | 150 | 0.434 | — | — |
| Advate ® | — | 150 | 1.920 | — | — |
| NovoEight ® | — | 150 | 1.536 | — | — |
| D'D3-FP & rVIII-SC | 1.5 | 150 | 0.688 | 300 | 62.8 |

TABLE 10-continued

| Treatment* | D'D3-FP dose [mg albumin/kg] | FVIII dose [IU/kg] | Volume [mL/kg] | Molar ratio D'D3-FP* over rFVIII | Molar ratio D'D3-FP* over rabbit VWF** |
|---|---|---|---|---|---|
| D'D3-FP & Advate ® | 1.5 | 150 | 2.174 | 300 | 62.8 |
| D'D3-FP & NovoEight ® | 1.5 | 150 | 1.790 | 300 | 62.8 | rFVIII = recombinant factor VIII; rVIII-SC = rVIII-SingleChain
*D'D3-FP calculated as monomer
**D'D3-FP calculated as monomer over endogenous VWF monomer to compare same numbers of FVIII binding sites. For calculation of the endogenous rabbit VWF the same specific activity as human VWF was assumed, i.e. one U/mL (or 100% of the norm) is assumed to be 10 μg/mL (measured rabbit plasma concentration 0.242 U/mL)
Assumption: same specific activity of all products, thus calculating for identical molar ratios Results In general, results between the different recombinant FVIII products are very comparable. The following observations regarding the prolongation of FVIII in plasma due to co-administration of D'D3-FP were made in detail:

The exposure of the co-administered FVIII (150 IU/kg chromogenic FVIII activity), quantified as FVIII:Ag via ELISA, was relevantly prolonged in the presence of D'D3-FP (FIG. 7). Plasma levels of FVIII:Ag could be measured maximally up to 32 h p.a. (Advate®) or 48 h p.a. (rVIII-SingleChain and NovoEight®) when the recombinant FVIII products were given alone (detection limit of 117 mIU/mL), and maximally up to the last time-point of 96 h p.a. (Advate®) or 120 h p.a. (rVIII-SingleChain and NovoEight®) after co-treatment with D'D3-FP.

cokinetics when given alone to 1.7-2.0 fold for rVIII-SingleChain and NovoEight®, which showed roughly comparable pharmacokinetics when given alone. Taken together and with major sight on relative decreases in clearance, the prolongation of pharmacokinetics of the three recombinant FVIII products was very comparable.

Example 5: Prolongation of Pharmacokinetics of FVIII by Co-Administration of rVIII-SingleChain with D'D3-His8 as Well as D'D3-CTP Fusion Protein in the Rat Material and Methods Animals: Female Crl:CD (Sprague Dawley) rats in a weight range of about 230-300 g were bred at Charles River

TABLE 11

Pharmacokinetic parameters of D'D3-FP and FVIII:Ag after co-administration of different rFVIII products and D'D3-FP in rabbits (non-compartmental analysis) Dose D'D3-FP 1.5 mg/kg, dose rFVIII 150 IU/kg

| Treatment* | Cmax, extrap. μg/ml (D'D3-FP $^c$) IU/mL (FVIII:Ag) | Clearance mL/kg/h | MRT h | Half-life, terminal h |
|---|---|---|---|---|
| D'D3-FP | | | | |
| D'D3-FP & rVIII-SC | 22.0 | 0.638 | 154 | 107 |
| D'D3-FP & Advate ® | 22.2 | 0.615 | 126 | 86 |
| D'D3-FP & NovoEight ® | 20.2 | 0.643 | 137 | 94 |
| FVIII:Ag | | | | |
| rVIII-SC | 2.51 | 3.71 | 23.2 | 17.3 |
| Advate ® | 1.52 | 9.93 | 17.8 | 13.4 |
| NovoEight ® | 2.48 | 4.42 | 23.0 | 18.5 |
| D'D3-FP & rVIII-SC | 2.84 | 1.37 (2.7fold$^a$) | 47.3 (2.0fold$^b$) | 32.6 (1.9fold$^b$) |
| D'D3-FP & Advate ® | 1.34 | 3.82 (2.6fold$^a$) | 57.5 (3.2fold$^b$) | 40.5 (3.0fold$^b$) |
| D'D3-FP & NovoEight ® | 2.22 | 1.88 (2.4fold$^a$) | 44.1 (1.9fold$^b$) | 31.1 (1.7fold$^b$) | rVIII-SC = rVIII-SingleChain
$^a$fold decrease over data from each rFVIII product given alone
$^b$fold increase over data from each rFVIII product given alone
$^c$ determination of albumin in μg/mL Calculation of decreases of clearance, as well as increases in MRT and terminal half-life of FVIII:Ag is presented in Table 11. Decreases in clearance were very comparable for all three products, i.e. between 2.4 fold to 2.7 fold changes. Based on the difference in t½ and MRT of the three recombinant FVIII products alone, the relative increase in MRT and t½ showed higher variability and ranged from 3.0-3.2 fold for Advate®, which has the shortest pharma- Laboratories (Sulzfeld, Germany). In house, the animals were kept at standard housing conditions, i.e. at 21-22° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations.

The group size was n=6, divided in 2 cohorts. Thus, n=3 animals per time-point were used.

Laboratory evaluations: The test articles were administered i.v. by a single injection into the lateral tail vein at a total volume of 3.0 mL/kg. D'D3 comprising proteins were applied at a dose level of 1 mg/kg based on OD values and co-administered with 200 IU/kg rVIII-SingleChain (rVIII-SingleChain, chromogenic activity) after incubating for approximately 30 minutes at +37° C. This leads to the D'D3 comprising protein ratios over rVIII-SingleChain of 78 and over endogenous VWF of 5.6 (Table 12); animals receiving only rVIII-SingleChain served as control.

Blood samples were taken retro-orbitally under short term anaesthesia at 5 min, 3, 8, 24, 32, 48, 56 and 72 h after intravenous bolus injection using an alternating sampling scheme. The PK profile was taken from two cohorts of rats per group. Blood samples were anticoagulated using sodium citrate (2 parts sodium citrate 3.13%+8 parts blood), processed to plasma and stored at −20° C. for the determination of FVIII antigen and/or D'D3 fusion protein.

D'D3-His8 and D'D3-CTP fusion protein exposure was determined by an ELISA method using D'D3-FP as a standard (see above). FVIII:Ag plasma levels were detected with the FVIII Asserachrom ELISA testkit from Stago, S.A.S., France.

Estimation of mean residence time (MRT), clearance (CL) and terminal half-life (t½) was done by one-compartmental methods.

TABLE 12

| | | | Treatment groups | |
|---|---|---|---|---|
| No Treatment | D'D3-His8 and D'D3-CTP protein dose [mg/kg]* | FVIII dose [IU FVIII:C/kg] | Molar ratio D'D3-His8 and D'D3-CTP protein** over rVIII-SC | Molar ratio D'D3-His8 and D'D3-CTP protein** over rat VWF *** |
| 1 rVIII-SC | — | 200 | — | — |
| 2 D'D3-His8 & rVIII-SC | 1 | 200 | 78 | 5.6 |
| 4 D'D3-CTP & rVIII-SC | 1 | 200 | 78 | 5.6 |

FVIII:C = chromogenic FVIII activity; rVIII-SC = rVIII-SingleChain
*D'D3-His8 and D'D3-CTP protein dose based on OD
**D'D3-His8 and D'D3-CTP protein dose corrected by molecular weight
*** D'D3-His8 and D'D3-CTP calculated as monomer over endogenous VWF monomer to compare same numbers of FVIII binding sites. For calculation of the endogenous rat VWF the same specific activity as human VWF was assumed, i.e. one U/mL (or 100% of the norm) is assumed to be 10 µg/mL (measured rat plasma concentration 0.946 U/mL)

Results

All measured data (up to 72 h p.a.) were well above the detection limit of the assay. MRT, t½ and clearance suggest that D'D3-CTP had a longer half-life and mean residence time as well as reduced clearance compared to D'D3-8His but even D'D3-8His showed slightly longer MRT and half-life as well as reduced clearance (Table 13).

The pharmacokinetic parameters of the co-administered FVIII (200 IU/kg chromogenic FVIII activity), quantified as FVIII:Ag via ELISA, were improved in the presence of both D'D3 proteins (Table 13). The difference in exposure of the D'D3 comprising proteins translates to the difference in FVIII:Ag exposure, i.e., D'D3-CTP led to a longer FVIII:Ag exposure than D'D3-8His.

TABLE 13

Pharmacokinetic parameters of D'D3 comprising proteins and FVIII:Ag after co-administration of rVIII-SingleChain and D'D3 proteins in rats (non-compartmental analysis). Dose D'D3 comprising protein 1 mg/kg, dose rVIII-SingleChain 200 IU/kg.

| Treatment* | $C_{max}$, extrap. µg/mL (D'D3 fusion protein [c]) IU/mL (FVIII:Ag) | Clearance mL/kg/h | MRT h | Half-life, terminal h |
|---|---|---|---|---|
| | D'D3 fusion protein | | | |
| D'D3-His8 & rVIII-SC | 31.6 | 6.80 | 10.3 | 7.2 |
| D'D3-CTP & rVIII-SC | 19.7 | 2.43 | 34.9 | 26.9 |
| | FVIII:Ag | | | |
| rVIII-SC | 3.02 | 6.45 | 10.3 | 7.1 |
| D'D3-His8 & rVIII-SC | 3.84 | 4.61 | 11.3 | 7.8 |
| | (1.4fold[a]) | (1.1fold[b]) | (1.1fold[b]) | |

TABLE 13-continued

Pharmacokinetic parameters of D'D3 comprising proteins and FVIII:Ag after co-administration of rVIII-SingleChain and D'D3 proteins in rats (non-compartmental analysis). Dose D'D3 comprising protein 1 mg/kg, dose rVIII-SingleChain 200 IU/kg.

| Treatment* | $C_{max}$, extrap. µg/mL (D'D3 fusion protein [c]) IU/mL (FVIII:Ag) | Clearance mL/kg/h | MRT h | Half-life, terminal h |
|---|---|---|---|---|
| D'D3-CTP & rVIII-SC | 3.35 | 3.58 (1.8fold[a]) | 16.7 (1.6fold[b]) | 11.6 (1.6fold[b]) | rVIII-SC = rVIII-SingleChain
[a] fold decrease over data from rVIII-SingleChain given alone
[b] fold increase over data from rVIII-SingleChain given alone
[c] determination based on OD Conclusion from PK Study Results These studies demonstrated that co-administration of D'D3-FP with FVIII products prolonged FVIII:Ag plasma MRT and half-life and decreased FVIII:Ag clearance independent of whether the FVIII molecule does contain the B domain is B-domain deleted or is present as a single- or two-chain product. This prolongation solely was dependent on the ratio of D'D3-FP over co-administered FVIII as well as over endogenous VWF.

Effects in the rat tend to be stronger than in the rabbit, when the increase in terminal half-life and MRT or reduction of clearance is depicted over the molar ratio of D'D3-FP over administered rVIII-Single-Chain (FIG. 8) as well as over endogenous VWF (FIG. 9). Regarding the molar ratio over rVIII-SingleChain, in the rat ≤30-fold ratios lead to smaller than twofold changes, while more favourable effects can be achieved at >50 fold ratios, and equal to or more than 2.7 fold improvement can be achieved starting at about 300 fold ratios. Even higher ratios above 750 or preferably 1000 or more preferably 1250 or even more preferably 1500 lead to a still higher improvement of terminal half-life and MRT or reduction of clearance.

Regarding ratios over endogenous VWF, species-specific differences are larger, suggesting that a 2 fold improvement may-be achieved in the rat (and in humans assuming similar endogenous VWF levels as in rats) at about ratios ≥5 and in the rabbit at about >60. 3 fold improvements were achieved in the rat at ratios of about >50.

Surprisingly it could be shown that D'D3-His8 having no half-life extending moiety also prolonged FVIII pharmacokinetic parameters slightly when administered at a ratio of 78 over co-administered FVIII and/or a ratio of 5.6 over endogenous VWF. Even better prolongation of FVIII half-life and mean residence time and reduced clearance was obtained at these ratios with a D'D3-CTP fusion protein which comprises the C-terminal peptide of human chorionic gonadotropin-ß subunit as a half-life extending moiety instead of the albumin comprised in D'D3-FP.

Since in the rat and the rabbit (in contrast to human haemophilia A patients) human administered and endogenous FVIII compete with D'D3-FP and VWF binding sites, it may be expected that the effect on FVIII in the human haemophilia A patient is even stronger.

Example 6: Determination of FVIII Affinity to VWF Fragment Dimer and Monomer

A VWF fragment (1-1242) albumin fusion (D'D3-FP) was expressed in a bioreactor; after purification as described above and isolation of monomer and dimer, the affinity of FVIII to these preparations was assessed through surface plasmon resonance via a Biacore instrument (T200, GE Healthcare).

An anti-albumin antibody (MA1-20124, Thermo Scientific) was covalently coupled via its N-terminus to an activated CM 3 chip by NHS (N-Hydroxysuccinimide) and EDC (Ethanolamine hydrochloride), both contained in the amine coupling kit (BR1000-50) from GE Healthcare. For immobilization 3 µg/mL of the antibody were diluted in sodium acetate buffer (10 mM, pH 5.0) and the antibody solution was flown over the chip for 7 min. at a flow rate of 10 µL/min. After the immobilization procedure non-coupled dextran filaments were saturated by flowing ethanolamine solution (1 M, pH 8.3) over the chip for 5 min (at a flow rate of 10 µL/min). The aim of saturating the flow cell was to minimize unspecific binding of the analytes to the chip. A reference flow cell was set up by saturating an empty flow cell with ethanolamine by using the same procedure as above.

Dimeric and monomeric D'D3-FP proteins, respectively, were immobilized to the covalently coupled anti-albumin antibody by a flow of the D'D3-FP proteins (5 µg/mL) over the chip for 3 min (flow rate of 10 µL/min). The captured mass of dimeric D'D3-FP was 335 RU and for monomeric D'D3-FP 147 RU, assuming one binding site both on the monomer and on the dimer D'D3-FP for FVIII.

To create binding curves for FVIII, each D'D3-FP protein preparation was diluted in running buffer (HBS-P+: 0.1 M HEPES, 1.5 M NaCl and 0.5% v/v Surfactant P20, pH 7.4; product code BR100671, GE Healthcare) to concentrations of 0.25 nM, 0.5 nM, 1 nM, 3 nM and 4 nM. By performing a single cycle kinetic, samples with ascending concentrations of each dilution were flown over the chip for 2 min (flow rate 30 µL/min.), followed by a dissociation time of 10 min. with running buffer HBS-P+. All measurements were performed twice. The temperature for the measuring procedure was adjusted to +25° C.

Binding parameters were calculated using BiaEvaluation Software. The curve fitting methods were based on Langmuir equations. The input data for calculations were the molar mass of the analyte FVIII (rVIII-SingleChain), other parameters like max. RU and slopes were automatically extracted out of the fitted association and dissociation curves. The outputs of BiaEvaluation Software are the association rate constants and the dissociation rate constants, from which the affinity constants were calculated. The results are shown in Table 12.

TABLE 12

FVIII affinity data for D'D3-FP dimer and monomer

| D'D3-FP preparation | ka [1/Ms] | kd [1/s] | KD [M] |
|---|---|---|---|
| D'D3-FP Dimer | 2.33E+07 | 1.37E−03 | 5.90E−11 |
| D'D3-FP Monomer | 4.41E+07 | 3.96E−03 | 8.99E−11 |

The association rate constant was slightly increased for rVIII-SingleChain to the monomeric D'D3-FP, while the dissociation rate constant of rVIII-SingleChain to D'D3-FP dimer was three times slower than to the monomer. The quotient of the dissociation rate constant and the association rate constant indicates the affinity of rVIII-SingleChain to D'D3-FP. The dimeric D'D3-FP hence shows an increased affinity to FVIII compared to the D'D3-FP monomer.

The invention claimed is:

1. A method of treating a blood coagulation disorder, comprising administering to a subject in need thereof an effective amount of (1) a polypeptide comprising a truncated von Willebrand Factor (VWF) and (2) a Factor VIII (FVIII), wherein the subject has endogenous VWF, wherein the polypeptide is capable of binding to the FVIII, and wherein
   (i) the molar ratio of the polypeptide to the FVIII is greater than about 50, and/or
   (ii) the molar ratio of the polypeptide to the endogenous VWF in the subject's plasma, immediately after administration of the polypeptide, is greater than about 0.5;
   wherein the truncated VWF comprises amino acids 764 to 1242 of SEQ ID NO:4.

2. The method according to claim 1, wherein the polypeptide comprises a half-life extending moiety.

3. The method according to claim 1, wherein the molar ratio in (ii) is the molar plasma concentration of the polypeptide divided by the molar plasma concentration of the endogenous VWF, and
   wherein the molar plasma concentration of the endogenous VWF is the concentration in normal human plasma (NHP).

4. The method according to claim 1, wherein the subject is a human.

5. The method according to claim 1, wherein the polypeptide is administered intravenously.

6. The method according to claim 1, wherein the truncated VWF lacks amino acids 1243 to 2813 of SEQ ID NO:4.

7. The method according to claim 1 wherein the truncated VWF consists of (a) amino acids 764 to 1242 of SEQ ID NO:4, (b) an amino acid sequence having at least 90% sequence identity to amino acids 764 to 1242 of SEQ ID NO:4, or (c) a fragment of (a) or (b).

8. The method according to claim 2, wherein the half-life extending moiety is a heterologous amino acid sequence fused to the truncated VWF.

9. The method according to claim 8, wherein the heterologous amino acid sequence comprises an immunoglobulin constant region or a portion thereof, transferrin or a fragment thereof, a C-terminal peptide of human chorionic gonadotropin, a solvated random amino acid chain with large hydrodynamic volume (XTEN), a homo-amino acid repeat (HAP), a proline-alanine-serine repeat (PAS), albumin, afamin, alpha-fetoprotein, a Vitamin D binding protein, a polypeptide capable of binding under physiological conditions to albumin or an immunoglobulin constant region, or a combination thereof.

10. The method according to claim 2, wherein the half-life extending moiety is conjugated to the polypeptide.

11. The method according to claim 10, wherein the half-life-extending moiety is selected from the group consisting of hydroxyethyl starch (HES), polyethylene glycol (PEG), polysialic acids (PSAs), elastin-like polypeptides, heparosan polymers, hyaluronic acid, albumin binding ligands, and combinations thereof.

12. The method according to claim 1, wherein the polypeptide is a glycoprotein comprising N-glycans, and wherein at least 75% of the N-glycans comprise, on average, at least one sialic acid moiety.

13. The method according to claim 1 wherein the polypeptide is a dimer.

14. The method according to claim 1, wherein the mean residence time (MRT) of the FVIII is increased by co-administration of the polypeptide, as compared to a reference treatment where the polypeptide and the FVIII are administered in equimolar amounts.

15. The method according to claim 1, wherein the clearance of the FVIII is decreased by co-administration of the polypeptide, as compared to a treatment with FVIII alone.

16. The method according to claim 1, wherein the plasma half-life of the polypeptide is greater than that of endogenous VWF.

17. The method according to claim 16, wherein the plasma half-life of the polypeptide is at least 25% greater than that of the endogenous VWF.

18. The method according to claim 8, wherein the heterologous amino acid sequence comprises an Fc fragment of an immunoglobulin.

19. The method according to claim 10, wherein the half-life-extending moiety comprises a fatty acid chain.

20. The method according to claim 1, wherein the polypeptide is a glycoprotein comprising N-glycans, and wherein at least 85% of the N-glycans comprise, on average, at least one sialic acid moiety.

21. The method of claim 1, wherein the FVIII and the polypeptide are administered separately.

22. The method of claim 1, wherein the FVIII and the polypeptide are administered simultaneously or sequentially.

23. The method of claim 1, wherein the administration increases the plasma half-life of FVIII and/or reduces the frequency of administration of FVIII.

* * * * *